United States Patent
Christensen et al.

(10) Patent No.: US 7,869,011 B2
(45) Date of Patent: Jan. 11, 2011

(54) APPARATUS AND METHODS FOR ANALYSIS AND SORTING OF PARTICLES SUCH AS POLYMER BEADS

(75) Inventors: Soeren Flygenring Christensen, Frederiksberg (DK); Ib Johannsen, Vaerloese (DK)

(73) Assignee: Novo Norkisk A/S, Baysvaerd (DK)

( * ) Notice: Subject to any disclaimer, the term of this patent is extended or adjusted under 35 U.S.C. 154(b) by 568 days.

(21) Appl. No.: 10/583,997

(22) PCT Filed: Dec. 22, 2004

(86) PCT No.: PCT/DK2004/000910

§ 371 (c)(1),
(2), (4) Date: Aug. 11, 2008

(87) PCT Pub. No.: WO2005/062018

PCT Pub. Date: Jul. 7, 2005

(65) Prior Publication Data

US 2009/0025489 A1    Jan. 29, 2009

Related U.S. Application Data

(60) Provisional application No. 60/535,522, filed on Jan. 12, 2004.

(30) Foreign Application Priority Data

Dec. 22, 2003  (DK) ............................... 2003 01917

(51) Int. Cl.
*G01J 3/44* (2006.01)
(52) U.S. Cl. ....................................................... 356/72
(58) Field of Classification Search ....................... None
See application file for complete search history.

(56) References Cited

U.S. PATENT DOCUMENTS 5,183,487 A * 2/1993 Lodico et al. .................. 55/289

(Continued)

FOREIGN PATENT DOCUMENTS

WO    WO 93/06121    4/1993

(Continued)

OTHER PUBLICATIONS

Ben-Eliezer, et al., "All-optical extended depth of field imaging system", *J. Opt. A: Pure Appl. Opt*, vol. 5, pp. S164-S169, 2003.

(Continued)

*Primary Examiner*—Tu T Nguyen
(74) *Attorney, Agent, or Firm*—Iver P. Cooper

(57) ABSTRACT

The present invention relates to an apparatus for analysing beads and particles, such as polymer beads used e.g. for solid phase synthesis. The apparatus comprises a) a vacuum container comprising at least one planar capture body capable of rotating around a central axis, wherein said capture body comprises a plurality of through-going inlets, and wherein the diameter of each inlet is smaller than the average diameter of the beads to be measured and/or analysed and/or sorted, b) a pressure controlling device capable of controlling the pressure in the vacuum container, c) a device for rotating the vacuum container around the axis of the capture body, and d) a device for measuring at least one property of at least one bead, the apparatus further comprising a capture body support, supporting the capture body, and a vacuum container housing.

22 Claims, 16 Drawing Sheets

U.S. PATENT DOCUMENTS

| | | | |
|---|---|---|---|
| 5,227,487 | A | 7/1993 | Haugland et al. |
| 5,274,113 | A | 12/1993 | Kang et al. |
| 5,288,514 | A | 2/1994 | Ellman |
| 5,326,692 | A | 7/1994 | Brinkley et al. |
| 5,405,975 | A | 4/1995 | Kuhn et al. |
| 5,433,896 | A | 7/1995 | Kang et al. |
| 5,439,624 | A | 8/1995 | Anderson et al. |
| 5,442,045 | A | 8/1995 | Haugland et al. |
| 5,451,663 | A | 9/1995 | Kang et al. |
| 5,453,517 | A | 9/1995 | Kuhn et al. |
| 5,459,276 | A | 10/1995 | Kuhn et al. |
| 5,516,864 | A | 5/1996 | Kuhn et al. |
| 5,549,974 | A | 8/1996 | Holmes et al. |
| 5,573,909 | A | 11/1996 | Singer et al. |
| 5,648,270 | A | 7/1997 | Kuhn et al. |
| 5,719,667 | A * | 2/1998 | Miers .......................... 356/73 |
| 5,723,218 | A | 3/1998 | Haugland et al. |
| 5,786,219 | A | 7/1998 | Zhang et al. |
| 6,083,682 | A | 7/2000 | Campbell et al. |

FOREIGN PATENT DOCUMENTS

| | | |
|---|---|---|
| WO | WO 95/25737 | 9/1995 |
| WO | WO 95/32425 | 11/1995 |
| WO | WO 96/03424 | 2/1996 |
| WO | WO 97/15390 | 5/1997 |
| WO | WO 97/22594 | 6/1997 |
| WO | WO 97/35199 | 9/1997 |
| WO | WO 97/40034 | 10/1997 |
| WO | WO 98/24549 | 6/1998 |
| WO | WO 99/24458 | 5/1999 |
| WO | WO 99/37814 | 7/1999 |
| WO | WO 99/42209 | 8/1999 |
| WO | WO 01/77391 | 10/2001 |
| WO | WO 03/047742 | 6/2003 |
| WO | WO 2004/028682 | 4/2004 |
| WO | WO 2004/052529 | 6/2004 |

OTHER PUBLICATIONS

Campian, et al., "Colored and Fluorescent Solid Supports", in Epton, ed., Innovations and Perspectives in Solid Phase Synthesis (Mayflower Worldwide Ltd: 1994), p. 469-472.

Cuche, et al., "Digital holography for quantitative phase-contrast imaging", Optics Letters, vol. 24, No. 5, Mar. 1, 1999.

Daneshvar, et al., "Detection of biomolecules in the near-infrared spectral region via a fiber-optic immunosensor", Journal of Immunological Methods, vol. 226, pp. 119-128, 1999.

Dowski, at al., "Extended depth of field through wave-front coding", Applied Optics, vol. 34, No. 11, pp. 1859-1866, Apr. 10, 1995.

Durig, et al., "Fourier Transform Raman Spectroscopy of Brightly Colored Commercially Available Dyestuffs and Pigments", Journal of Raman Spectroscopy, vol. 24, pp. 281-285, 1993.

Egner, et al., "Tagging in combinatorial chemistry: the use of coloured and fluorescent beads", Chem. Commun., pp. 735-736, 1997.

Eriksson, et al., "Lipid and water diffusion in bicontinuous cubic phases measured by NMR", Biophys. Journal, vol. 64, pp. 129-136, Jan. 1993.

Früchtel, et al., "Organic Chemistry on Solid Supports", Angew. Chem. Int. Ed. Engl., vol. 35, pp. 17-42, 1996.

Gante, Joachim, "Peptidomimetics-Tailored Enzyme Inhibitors", Angew. Chem. Int. Ed. Engl., vol. 33, pp. 1699-1720, 1994.

Guineau, Bernard, "Non-Destructive Analysis of Organic Pigments and Dyes Using Raman Microprobe, Microfluorometer or Absorption Microspectrophotometer", Studies in Conservation, vol. 34, No. 1, pp. 38-44, Feb. 1989.

Lakowicz, et al., "Time-Resolved Fluorescence Spectroscopy and Imaging of DNA Labeled with DAPI and Hoechst 33342 Using Three-Photon Excitation", Biophysical Journal, vol. 72, pp. 567-578, Feb. 1997.

Lewis, et al., "The Use of Fourier Transform Infrared (FT-IR) Spectroscopy to Study the State of Heterobifunctional Reactive Dyes", Dyes and Pigments, vol. 39, No. 2, pp. 111-123, 1998.

Needels, et al., "Generation and screening of an oligonucleotide-encoded synthetic peptide library", Proc. Natl. Acad. Sci. USA, vol. 90, pp. 10700-10704, Nov. 1993.

Patel, et al., "Applications of small-molecule combinatorial chemistry to drug discovery", DDT, vol. 1, No. 4, pp. 134-144, Apr. 1996.

Rahman, et al., "Infrared and Raman Spectra of a Single Resin Bead for Analysis of Solid-Phase Reactions and Use in Encoding Combinatorial Libraries", J. Org. Chem., vol. 63, pp. 6196-6199, 1998.

Rapaport, et al., "Visible light emission from dyes excited by simultaneous absorption of two different frequency beams of light", Applied Physics Letters, vol. 74, No. 3, pp. 329-331, Jan. 18, 1999.

Rohr, Jürgen, "Combinatorial Biosynthesis—An Approach in the Near Future?", Angew. Chem. Int. Ed. Engl., vol. 34, No. 8, pp. 881-885, 1995.

Tawa, et al., "Polarized Light-Induced Anisotropy in Polymer Films Doped with Az Dyes in the Photostationary State Studied by IR Spectroscopy", Mat. Res. Soc. Symp. Proc., vol. 488, pp. 885-890, 1998.

Tentorio, et al., "Preparation and Optical Properties of Spherical Colloidal Aluminum Hydroxide Particles Containing a Dye", Journal of Colloid and Interface Science, vol. 77, No. 2, pp. 418-426, Oct. 1980.

Van Helden, et al., "Contrast Variation in Light Scattering: Silica Spheres Dispersed in Apolar Solvent Mixtures", Journal of Colloid and Interface Science, vol. 76, No. 2, pp. 418-433, Aug. 1980.

Yamaguchi, et al., "Image formation in phase-shifting digital holography and applications to microscopy", Applied Optics, vol. 40, No. 34, pp. 6177-6186, Dec. 1, 2001.

Youvan, et al., "Fluorescence Imaging Micro-Spectrophotometer (FIMS)", Biotechnology ET Alia, vol. 1, pp. 1-16, 1997.

* cited by examiner

APPARATUS AND METHODS FOR ANALYSIS AND SORTING OF PARTICLES SUCH AS POLYMER BEADS

All patent and non-patent references cited herein are incorporated in their entirety. This application is a non-provisional of U.S. provisional application Ser. No. 60/535,522 filed 12 Jan. 2004, which is hereby incorporated by reference in its entirety.

FIELD OF INVENTION

The present invention relates to an apparatus for analysing beads and particles, such as polymer beads used e.g. for solid phase synthesis. The apparatus in one embodiment comprises a rotatable, circular disc comprising a plurality of through-going inlets, wherein an individual bead from a composition comprising different beads can be fixed to the disc at the end-position of a through-going inlet by applying a pressure drop over said disc comprising said through-going inlets. The pressure drop results in beads being sucked (i.e. detachably fixed) onto the disc on top of the through-going inlets.

When the disc is rotated the beads are transferred from the position where they initially became attached to the disc to fixed positions wherein suitable devices for measuring and/or analysing and/or sorting the beads can be operated in order to e.g. measure and/or analyse and/or sort at least one bead of a plurality of beads.

Also provided are methods for measuring and/or analysing and/or sorting particles, as well as methods for processing particles once they have been analysed and/or sorted.

BACKGROUND OF INVENTION

When large numbers of polymer beads, such as more than 10.000 beads, are to be analysed one by one at an acceptable total analysis time, the beads are typically dispersed in a liquid and passed through a measuring section of the analysis instrument.

In order for the beads to be lined up in a flow channel and passed through a measuring section one by one, while at the same time avoiding that beads stick together or to the walls of the flow system, a high flow velocity is required. Typical flow velocities are in the order of 1 m/s (meter per second) is required. Consequently the residence time of each bead in the measuring section is very short, typically less than 1 millisecond. This poses a number of serious problem as not all measuring or analysing devices can operate within such a short "window of opportunity" for measuring and analysing bead properties. Furthermore, the devices which can in fact operate in the "window of opportunity" of less than 1 millisecond often does not work reliably or under optimal conditions with such a short residence time of the beads.

Also, the demands on the measuring components are very high and prevents the application of certain advanced and time consuming measuring methods. If there is a need for sorting the beads on the basis of the measured properties, there is often not enough time to complete the algebra and very complicated mathematical calculations required to establish whether a bead is to be selected or discarded on the basis of the measurement and analysis performed. One reason for this shortcoming of prior art devices for bead sorting is that the sorting unit is typically placed at a very short distance downstream from the measuring section. Accordingly, time consuming mathematical calculations cannot be used in this context as a bead would have passed the sorting unit long before the result of the measuring of bead properties can be established.

Increasing the distance between the measuring section and the sorting unit often does not offer any practical solution to the problem as an increased distance also increases the risk of beads getting stuck to the wall sections, or getting stuck together, and a longer flow section furthermore contributes to variations in the velocity of individual beads—both of which factors will result in a reduced validity of the results required for a correct sorting of beads.

A further problem often encountered in purely fluid dynamic based bead manipulation methods is that the flow of beads cannot be interrupted on demand without such an interruption causing a considerable shutdown period followed by often laborious and time-consuming start up procedures.

During the operation of a purely fluid based bead sorter, such as e.g. the COPAS bead sorter supplied by Harvard Bioscience, a number of difficulties regarding fluid handling of particles such as e.g. polymer beads are experienced. For example, beads tend to get stuck in the feed tube to the flow cell where the beads are analysed, and two or more beads may therefore stick together as they enter the flow cell. As a result a considerable fraction of beads are not sorted correctly, such as e.g. more than 20%, and the resulting fractions of beads must be resorted to obtain an acceptable level of accuracy. This is time-consuming and inefficient as it requires beads to be measured and analysed more than once.

In order for the beads to line up one by one in the feed tube to the flow cell a high flow velocity of about 1 m/s is required corresponding to a measuring time of less than 1 millisecond per bead and a computation time of less than 100 milliseconds from bead measurement to bead sorting. This places very high demands on sensors, data handling equipment, and the fluid handling components of the sorting unit. In cases where beads are to be imaged even lower exposure times, e.g. 10 microseconds, are required for freezing the motion of a passing bead and obtaining a sharp image.

In cases where advanced bead analysis, such as resolving the three dimensional structure of spatially encoded microparticles must be carried out at a high through-put rate, high flow velocities and corresponding low residence times in the flow cell poses an even greater challenge for the equipment as the data handling is much more complex compared to conventional bead sorters in which a more simple analysis, such as bead size or total fluorescence, is measured.

There is a need for an improved apparatus for bead analysis and sorting which allows high through-put rates while maintaining sufficiently high residence times, e.g. in a compartment or section in which bead properties can be measured, thus ensuring that more reliable data are generated for each and every bead, wherein each bead is preferably only measured once prior to being sorted on the basis of the result and analysis of the measurement of a bead property.

WO 01/77391 A1 (Quantum Dot) discloses devices, systems, kits, and methods for detecting and/or identifying a plurality of spectrally labeled bodies well-suited for performing multiplexed assays. By spectrally labeling the beads with materials which generate identifiable spectra, a plurality of beads may be identified within the fluid. Reading of the beads is facilitated by restraining the beads in arrays, and/or using a focused laser. The present invention is in one aspect directed to a bead sorter comprising a rotatable, circular capture body comprising a plurality of through-going inlets.

WO 99/42209 (Takeda) discloses a bead sorter comprising a bead holder. The bead holder has a surface having a recess sized to receive a single bead, a passage connected at one end thereof to the recess, and a restricting portion for preventing the bead from being entering into the passage. Also, the bead separator has first, second, and third stations. The first station is to introduce a negative pressure in the passage, thereby holding the bead in the recess. The second station is to eject a liquid around the recess retaining the bead, thereby removing a bead or beads possibly existing around the recess away from the recess. The third station is to introduce a positive pressure in the passage, thereby releasing the bead from the recess. A transporting means is provided for moving the recess through the first, second, and then third stations. One embodiment of the present invention is directed to a bead sorter which does not comprise a bead holder having a recess in at least one surface. Rather, the present invention employs in one embodiment a planar disc comprising a plurality of through-going inlets.

SUMMARY OF INVENTION

The present invention relates in one aspect to an apparatus for analysing beads and particles, such as polymer beads used e.g. for solid phase synthesis. The apparatus in one embodiment comprises a rotatable, capture body, such as a circular disc comprising a plurality of through-going inlets, wherein an individual bead from a composition comprising different beads can be fixed to the disc at the end-position of a through-going inlet by applying a pressure drop over said disc comprising said through-going inlets. The pressure drop results in beads being sucked (i.e. detachably fixed) onto the surface of the planar disc on top of the through-going inlets. As essentially all of the bead is present on top of the disc (i.e. extends from the surface rather than being contained in a recess therein), analysis of bead properties can be performed more readily and more easily while still ensuring a high through-put rate.

When the capture body, preferably in the form of a planar disc comprising a plurality of through-going holes, is rotated, the beads are transferred from the position where they initially became attached to the disc to fixed positions wherein suitable devices for measuring and/or analysing and/or sorting the beads can be operated in order to e.g. measure and/or analyse and/or sort at least one bead of a plurality of beads.

The present invention offers several solutions to the problems associated with prior art proposals for achieving a more efficient sorting of e.g. polymer beads:

The present invention ensures, when compared to the prior art, i) that the comparatively short measurement times of prior art devices can be increased, thus allowing more reliable data to be generated, and/or allowing a wider variety of analysing equipment to be used, ii) that the comparatively short analysis time (i.e. time for algebra/mathematical calculations) of prior art devices can be increased considerably, thereby allowing more conclusive results to be generated, thereby allowing a more correct sorting to be achieved, iii) that the limited spatial control over beads in prior art flow systems can be increased as the beads are detachably fixed to the capture body of the vacuum container of the apparatus of the present invention, and iv) that the sorting method can be interrupted at request for a short period of time without decreasing the high through-put rate—the reason being that no time-consuming and laborious start-up procedures are required.

In summary, when compared to fluid dynamics based instruments, the present invention allows for measurement exposure times orders of magnitude higher while maintaining comparable through-put rates, i.e. total number of beads screened per total screening time.

In one aspect of the present invention there is provided an apparatus for measuring a plurality of optically detectable particles or beads, such as polymer beads, said apparatus comprising a) a vacuum container comprising at least one planar capture body capable of rotating around a central axis,
   wherein said planar capture body comprises a plurality of through-going inlets,
   wherein the diameter of each inlet is smaller than the average diameter of the beads being measured and/or analysed and/or sorted, b) a pressure controlling device capable of controlling the pressure in the vacuum container, and c) a device for rotating the vacuum container around the axis of the capture disc.

The apparatus in one embodiment further comprises an analysing device for analysing results being generated from the measurement of the at least one property of the at least one bead or particle, wherein said analysis enables individual beads to be characterised and/or identified and optionally also sorted.

Also provided in accordance with the present invention are methods for measuring and/or analysing and/or sorting particles, as well as methods for processing particles once they have been analysed and/or sorted. In one aspect the methods comprise the steps of diverting the beads to the bead sorting apparatus of the invention, measuring at least one property of at least one bead, analysing the result of the measurement of the at least one property, and sorting at least one bead based on the analysis of the measurement result.

The analysis of beads can involve a determination of at least one bead property and/or involve identifying individual beads characterised by at least one unique feature, such as a plurality of spatially immobilised microparticles in each bead. Beads comprising a plurality of spatially immobilised microparticles are termed "encoded" beads.

The identification of individual beads from a composition of beads can involve a determination of the coordinates of the plurality of spatially immobilised microparticles in an "encoded" bead. The determination of the spatial coordinates preferably allows one to generate at least one distance matrix for the "encoded" bead to be identified.

Distance matrix data can be further processed in order to provide—if required—more conclusive results on the basis of which the identity of an individual "encoded" bead can be determined. One further data processing step involves providing, for an individual "encoded" bead to be identified, a set of all the possible geometrical figures, such as triangles, generated on the basis of the spatial coordinates used for the generation of at least one distance matrix for the bead in question.

It is thus possible to generate—based on the spatial coordinates of the spatially immobilised microparticles initially used for a determination of at least one distance matrix of the individual "encoded" bead to be identified—a well-defined set of all (i.e. the total set of) geometrical figures, such as triangles, which can be generated from the set of spatial coordinates of the spatially immobilised microparticles of a single "encoded" bead to be identified. The total set of e.g. triangles generated in this way can be used for the identification of individual "encoded" beads in a population of different beads such as polymer beads used for solid phase synthesis.

As data for the identification of all "encoded" beads in the bead population have initially been recorded on a data storage medium, i.e. data for the identification of all "encoded" beads in the bead population have been recorded prior to the actual step of identifying individual beads, all distance matrices and/or all geometrical figures will already have been stored on the data storage medium. The total set of distance matrices and/or the total set of geometrical figures is therefore available and can thus be used for analysing and/or identifying individual "encoded" beads.

Consequently, it is possible to compare—for an "encoded" bead to be identified—at least one distance matrix, or the total set of geometrical figures one can generate on the basis of the spatial coordinates of the spatially immobilised microparticles used for the distance matrix determination. An individual "encoded" bead will be identified once a "match" is found between the recorded at least one distance matrix for the bead to be identified and the already stored at least one distance matrix for all beads, or once a "match" is found between the recorded total set of geometrical figures for the bead to be identified and the already stored total set of geometrical figures for all beads, i.e. a "match" between a recorded data set and an already obtained (and stored) data set for the bead in question.

Accordingly, in preferred aspects of the present invention the below-mentioned methods are provided.

A method for measuring at least one property of at least one bead of a plurality of beads, such as polymer beads, said method comprising the steps of
 i) providing a plurality of beads each comprising at least one label,
 ii) providing an apparatus for measuring at least one property of at least one bead according to any of the measuring methods of the invention,
 iii) contacting at least one bead of the plurality of beads provided in step i) with the vacuum container capture body of the apparatus provided in step ii),
 iv) rotating the capture body to transfer at least one bead from the loading section of the vacuum container to the measuring section of the vacuum container, and
 v) using the measuring device of the apparatus for measuring at least one property of at least one bead.

A method for analysing data generated by measuring at least one property of at least one bead of a plurality of beads, such as polymer beads, said method comprising the steps of
 i) providing a plurality of beads each comprising at least one label,
 ii) providing an apparatus of the invention for analysing at least one property of at least one bead,
 iii) contacting at least one bead of the plurality of beads provided in step i) with the vacuum container capture body of the apparatus provided in step ii),
 iv) rotating the capture body to transfer at least one bead from the loading section of the vacuum container to the measuring section of the vacuum container,
 v) using the measuring device of the apparatus for measuring at least one property of at least one bead, and
 vi) analysing data generated by the measuring device for measuring at least one property of at least one bead.

A method for identifying at least one bead of a plurality of beads, such as polymer beads, said method comprising the steps of
 i) providing a plurality of beads each comprising at least one label,
 ii) providing an apparatus of the invention for analysing at least one property of at least one bead,
 iii) contacting at least one bead of the plurality of beads provided in step i) with the vacuum container capture body of the apparatus provided in step ii),
 iv) rotating the capture body to transfer at least one bead from the loading section of the vacuum container to the measuring section of the vacuum container,
 v) using the measuring device of the apparatus for measuring at least one property of at least one bead, and
 vi) using the analysing device for analysing data generated by the measuring device for measuring at least one property of at least one bead, and
 vii) identifying at least one bead of a plurality of beads by analysing the data generated by the measuring device for measuring at least one property of at least one bead.

A method for sorting at least one bead of a plurality of beads, such as polymer beads, said method comprising the steps of
 i) providing a plurality of beads each comprising at least one label,
 ii) providing an apparatus according to the invention for sorting at least one bead,
 iii) contacting at least one bead of the plurality of beads provided in step i) with the vacuum container capture body of the apparatus provided in step ii),
 iv) rotating the capture body to transfer at least one bead from the loading section of the vacuum container to the measuring section of the vacuum container,
 v) using the measuring device of the apparatus for measuring at least one property of at least one bead,
 vi) using the analysing device for analysing data generated by the measuring device for measuring at least one property of at least one bead, and
 vii) sorting the at least one bead of a plurality of beads based on the result of the analysis performed in step vi).

A method for sorting at least one bead of a plurality of beads, such as polymer beads, said method comprising the steps of
 i) providing a plurality of beads each comprising at least one label,
 ii) providing an apparatus according to the invention for sorting at least one bead,
 iii) contacting at least one bead of the plurality of beads provided in step i) with the vacuum container capture body of the apparatus provided in step ii),
 iv) rotating the capture body to transfer at least one bead from the loading section of the vacuum container to the measuring section of the vacuum container,
 v) using the measuring device of the apparatus for measuring at least one property of at least one bead, and
 vi) using the analysing device for analysing data generated by the measuring device for measuring at least one property of at least one bead,
 vii) identifying at least one bead of a plurality of beads by analysing the data generated by the measuring device for measuring at least one property of at least one bead, and
 viii) sorting the at least one bead of a plurality of beads based on the identification performed in step vii).

A method for treating at least one bead of a plurality of beads, such as polymer beads, said method comprising the steps of
 i) providing a plurality of beads each comprising at least one label,
 ii) providing an apparatus according to the invention for treating at least one bead,
 iii) contacting at least one bead of the plurality of beads provided in step i) with the vacuum container capture body of the apparatus provided in step ii),
 iv) rotating the capture body to transfer at least one bead from the loading section of the vacuum container to the measuring section of the vacuum container, v) using the measuring device of the apparatus for measuring at least one property of at least one bead,
vi) analysing data generated by the measuring device for measuring at least one property of at least one bead, and
vii) treating at least one bead of a plurality of beads based on the result of the analysis performed in step vi).

A method for treating at least one bead of a plurality of beads, such as polymer beads, said method comprising the steps of
i) providing a plurality of beads each comprising at least one label
ii) providing an apparatus according to the invention for treating at least one bead,
iii) contacting at least one bead of the plurality of beads provided in step i) with the vacuum container capture body of the apparatus provided in step ii),
iv) rotating the capture body to transfer at least one bead from the loading section of the vacuum container to the measuring section of the vacuum container,
v) using the measuring device of the apparatus for measuring at least one property of at least one bead, and
vi) using the analysing device for analysing data generated by the measuring device for measuring at least one property of at least one bead,
vii) identifying at least one bead of a plurality of beads by analysing the data generated by the measuring device for measuring at least one property of at least one bead, and
viii) treating at least one bead of a plurality of beads based on the identification obtained in step vii).

A method for treating at least one bead of a plurality of beads, such as polymer beads, said method comprising the steps of
i) providing a plurality of beads each comprising at least one label,
ii) providing an apparatus according to the invention for treating at least one bead,
iii) contacting at least one bead of the plurality of beads provided in step i) with the vacuum container capture body of the apparatus provided in step ii),
iv) rotating the capture body to transfer at least one bead from the loading section of the vacuum container to the measuring section of the vacuum container,
v) using the measuring device of the apparatus for measuring at least one property of at least one bead,
vi) analysing data generated by the measuring device for measuring at least one property of at least one bead,
vii) sorting the at least one bead of a plurality of beads based on the result of the analysis performed in step vi), and
viii) treating the at least one bead of a plurality of beads having been sorted in step vii).

A method for treating at least one bead of a plurality of beads, such as polymer beads, said method comprising the steps of
i) providing a plurality of beads each comprising at least one label,
ii) providing an apparatus according to the invention for treating at least one bead,
iii) contacting at least one bead of the plurality of beads provided in step i) with the vacuum container capture body of the apparatus provided in step ii),
iv) rotating the capture body to transfer at least one bead from the loading section of the vacuum container to the measuring section of the vacuum container,
v) using the measuring device of the apparatus for measuring at least one property of at least one bead, and
vi) using the analysing device for analysing data generated by the measuring device for measuring at least one property of at least one bead,
vii) identifying at least one bead of a plurality of beads by analysing the data generated by the measuring device for measuring at least one property of at least one bead,
viii) sorting the at least one bead of a plurality of beads based on the identification performed in step vii), and
ix) treating the at least one bead of a plurality of beads having been sorted in step viii).

When the invention relates to "encoded" beads, the analysing step of the above methods preferably involves the determination of the coordinates in space of the spatially immobilised microparticles of at least one "encoded" bead, and the generation, for preferably each of the analysed beads, of at least one distance matrix on the basis of said determination of coordinates of spatially immobilised microparticles.

Accordingly, there is provided in one embodiment a method for determining or calculating for an "encoded" bead at least one distance matrix of said bead, preferably by a method comprising the steps of
i) determining for each microparticle of the encoded bead the 2D coordinates in the XZ-plane and in the YZ-plane, thereby generating a first set of data and a second set of data,
ii) combining the first set of data and the second set of data and thereby obtaining at least one set of 3D coordinates for the microparticles, and
iii) calculating the distance matrix as the full set of distances between particles for which the set of 3D coordinates is obtained.

Preferably, only one distance matrix is obtained for each "encoded" bead. When more than one distance matrix is obtained it is preferred to re-calculate the distance matrix in accordance with preferred methods directed to this, as disclosed in more detail herein below in the detailed description of the invention.

The above method for determining the distance matrix of the at least one "encoded" bead preferably comprises the further steps of
iv) comparing the Z-coordinates of different particles within each particle, and
v) selecting particles wherein the difference between Z-coordinates is less than a predetermined threshold value, delta-Z,
vi) pair-wise grouping the selected particles according to delta-Z values,
vii) maintaining the X-coordinate and the Z-coordinate for each of the pair-wise grouped particles, and
viii) switching the Y-coordinate between pair-wise grouped particles, thereby obtaining an alternative set of 3D coordinates from which an alternative distance matrix can be calculated.

By determining the distance matrix for each bead and store the data as a "finger print" for each bead, it is possible to subsequently identify individual beads in a composition comprising beads for which the distance matrix has already been determined.

Accordingly, there is provided a method for identifying individual beads comprising the steps of
i) determining the set of distance matrices for individual encoded beads according to the methods of the present invention,
ii) deriving from each of the distance matrices generated in step i) all of the possible geometrical figures, such as triangles, which can be generated by connecting microparticle coordinates with straight lines, and iii) recording and storing the set of geometrical figures for each "encoded" bead of the composition to be identified,
iv) selecting a subset of "encoded" beads,
v) identifying one or more of the selected "encoded" beads on the basis of a comparison of the set of geometrical figures of said bead(s) with all sets of geometrical figures recorded for the composition in step iii).

The geometrical figures are preferably triangles. Preferred methods for deriving geometrical figures in the shape of triangles from methods for distance matrix determinations are listed herein below. The method is based on categorizing and classifying 3D positions from 2 2D projections.

The objective of the method is to determine 3D coordinates of spatially immobilised microparticles within e.g. a beaded polymer matrix. Accordingly, a large set of unknown 3D locations of spatially immobilised microparticles is rapidly searched though creation of a 3 dimensional table using the length of each side of the spanned triangle as an entry.

The aim of the search is to create a classification table, based on known distances between particles derived from each orthogonal image pair. Two such image pairs giving rise to the same sets of distances are most likely image pairs of the same bead.

The number of microparticle to microparticle distances of each encoded bead is large, and does discriminate well among a large set (100000 or more) of encoded beads. Utilizing the constraints of 3D connectivity, the method employ the constraint given by triangles in 3D.

Each code spans one or more triangles, where each triangle spans a plane. The number of spanned planes is significant less than the number of spanned distances between microparticle sets.

The aim is to create a lookup table where each entry is the distance between the side length of each triangle, equal to a spanned plane in 3D. A 3D look-up table can be stored in memory, and look-up for matches is performed efficiently.

Within each table entry three units spanning this particular plane is stored in a linked list. Each image is searched for triangles with the same side length, limiting the number of matches significantly. Each match is then searched individually for full 3D correspondence. The best number of table entries i.e. the unit of each length depends on the set of length differences, but as a general rule, each length unit should contain the variation of side lengths when capturing several image of the same unit.

Accordingly, there is provided a method for identifying an individual bead, $b_q$, of a plurality of beads, $B=(b_1, b_2, \ldots, b_H)$, where $1 \leq q \leq H$, and H being the number of beads, H preferably being less than $10^{17}$, such as less than $10^{15}$, such as less than $10^{13}$, such as less than $10^{11}$, such as less than $10^{10}$, for example less than $10^9$, such as less than $10^8$, said method comprising the steps of 1. providing a plurality of distance encoded beads, B,
2. obtaining one orthogonal pair of images, $(I_{h,x,z}, I_{h,y,z})$, of each bead, $b_h$, where $h=1, 2, \ldots, H$, of said plurality of distance encoded beads, B,
3. deriving from each of said orthogonal pairs of images, $(I_{h,x,z}, I_{h,y,z})$, the set, $C_h$, of possible sets of three-dimensional microparticle positions represented by x, y, and z image pixel values for each bead, $b_h$, $C_h = (c_{h,1}, c_{h,2}, \ldots, c_{h,Eh})$, where $c_{h,e} = (x_{h,f,e}, y_{h,f,e}, z_{h,f,e})$, where $f=1, 2, \ldots, F_h$, and $F_h$ being the number of microparticles of bead $b_h$, and $e=1, 2, \ldots, E_h$, and $E_h$ being the number of possible sets of three-dimensional microparticle positions for bead $b_h$, 4. deriving for each set of possible sets of three-dimensional microparticle positions one distance matrix $$D_{h,e} = \begin{vmatrix} 0 & d_{h,e,1,2} & d_{h,e,1,3} & \ldots & d_{h,e,1,Fh} \\ d_{h,e,2,1} & 0 & d_{h,e,2,3} & \ldots & d_{h,e,2,Fh} \\ d_{h,e,3,1} & d_{h,e,3,2} & 0 & & \ldots \\ \ldots & \ldots & & \ldots & \\ d_{h,e,Fh,1} & d_{h,e,Fh,2} & \ldots & & 0 \end{vmatrix}$$

where $d_{h,e,i,j}$=integer$([(x_{h,e,i}-x_{h,e,j})^2+(y_{h,e,i}-y_{h,e,j})^2+(z_{h,e,i}-z_{h,e,j})2]^{1/2})$, where $i=1,2,\ldots F_h$, and $j=1,2,\ldots,F_h$, 5. deriving for each distance matrix, $D_{h,e}$, the full set of derivable triangles, $T_{h,e}=(t_{h,e,1}, t_{h,e,2}, \ldots, t_{h,e,Ghe})$, each triangle being represented by its three side length, $T_{h,e}=[t_{h,e,1}, t_{h,e,2}, \ldots, t_{h,e,Ghe}]=[(d_{h,1,2}, d_{h,1,3}, d_{h,2,3}),$
$(d_{h,1,2}, d_{h,1,4}, d_{h,2,4}), \ldots, (d_{h,(Fh-2),(Fh-1)}, d_{h,(Fh-2),Fh}, d_{h,(Fh-1),Fh})]$, $G_{h,e}$ being the total number of derivable triangles from distance matrix, $D_{h,e}$, 6. generating a subset, U, of all triangles, T, derived for the full set of beads, B, said subset of triangles comprising all different triangles derived for the full set of beads, $U=(u_1, u_2, \ldots, u_W)$, where $u_i \neq u_j$, for $i \neq j$, and $i=1, 2, \ldots, W$, and $j=1, 2, \ldots, W$, and W being the total number of different triangles derived for the full set of beads, B, 7. generating a look-up table, L, that for every triangle, $u_r$, where $r=1, 2, \ldots, W$, gives the subset, $A_r$, of the full set of beads, B, for which subset of the full set of beads at least one of its derived sets of triangles comprises $u_r$, $L=[(u_1, A_1), (u_2, A_2), \ldots, (u_w, A_w)]$, 8. obtaining one orthogonal pair of images of the bead, $b_q$, to be identified,
9. deriving from said one orthogonal pair of images the full set of possible sets of three-dimensional microparticle positions, $C_q=(c_{q,1}, c_{q,2}, \ldots c_{q,Eq})$, 10. deriving for each of said sets of possible sets of three-dimensional microparticle positions one distance matrix $$D_{q,e} = \begin{vmatrix} 0 & d_{q,e,1,2} & d_{q,e,1,3} & \ldots & d_{q,e,1,Fq} \\ d_{q,e,2,1} & 0 & d_{q,e,2,3} & \ldots & d_{q,e,2,Fq} \\ d_{q,e,3,1} & d_{q,e,3,2} & 0 & & \ldots \\ \ldots & \ldots & & \ldots & \\ d_{q,e,Fq,1} & d_{q,e,Fq,2} & \ldots & & 0 \end{vmatrix}$$

11. deriving for each distance matrix, $D_{q,e}$, the full set of derivable triangles, $T_q=(t_{q,e,1}, t_{q,e,2}, \ldots, t_{q,e,Gqe})$, each triangle being represented by its three side length, $T_q=[t_{q,e,1}, t_{q,e,2}, \ldots, t_{q,e,Gqe}]=[(d_{q,1,2}, d_{q,1,3}, d_{q,2,3}),$
$(d_{q,1,2}, d_{q,1,4}, d_{q,2,4}), \ldots, (d_{q,(F-2),(F-1)}, d_{q,(F-2),F}, d_{q,(F-1),F})]$, 12. finding for each of said triangles of said set of triangles, $T_q$, derivable from bead $b_q$ the corresponding set, $B_q$, of subsets of beads according to said look-up table, L, for which at least one of its derived sets of triangles comprises each of said triangles of said set of triangles, $T_q$, derivable from bead $b_q$, 13. registering for each of the beads of said subset of beads, $B_q$, the number of triangles contained in $T_q$, 14. identifying bead $b_q$ as the bead of said subset of beads, $B_q$, that has the highest number of triangles contained in $T_q$.

The apparatus according to the invention and the methods disclosed herein above makes it possible to perform applications such as e.g.:

A method for recording individual reaction steps involved in the step-wise synthesis of a chemical compound on an optically detectable bead, said method comprising the steps of a) spatially immobilizing a plurality of microparticles in each optically detectable bead, b) isolating, preferably by automated selection, at least a subset of the spatially encoded beads provided in step a), c) recording and storing a distance matrix or a geometrical figure derivable from the distance matrix for each bead, wherein said distance matrix or geometrical figure is preferably generated by any of the methods disclosed herein, d) stepwise synthesising chemical compounds on functional groups present on the encoded beads, wherein the identity of each bead is recorded and stored for each reaction step, and e) obtaining for each bead a record of the individual reaction steps, as well as a method for identifying a chemical compound having been synthesised on an optically detectable bead comprising a plurality of spatially immobilised microparticles comprising at least one label, said method comprising the steps of a) performing the recording method cited herein immediately above, b) selecting beads of interest by using an assay or a diagnostic screen selective for the chemical compound having been synthesized on the bead, c) recording the distance matrix for each of the beads selected in step b), d) comparing the distance matrix recorded in step c) with all of the distance matrices recorded and stored in step c) of the recording method cited herein immediately above, thereby obtaining information about the identity of the selected bead, e) identifying for each selected bead the sequence of individual steps having lead to the synthesis of the chemical compound, and f) identifying, based the sequence of individual steps, the chemical structure of the compound.

In a further aspect there is provided a method for generating a composition comprising a plurality of encoded beads, said method comprising the steps of i) synthesizing a monomer and/or macro-monomer and a crosslinker for polymerisation, and, ii) mixing the monomer and/or macro-monomer with microparticles to give an even dispersion of microparticles in the mixture, and iii) polymerising the monomer and/or macro-monomer by either i) suspension polymerisation and/or; ii) inverse suspension polymerisation and/or iii) bulk polymerisation followed by granulation and/or iv) droplet polymerisation.

In an even further aspect there is provided a method for generating a composition comprising a plurality of encoded beads and detecting and/or identifying individually identifiable beads, said method comprising the steps of:

(a) preparing a plurality of beads comprising spatially immobilised microparticles comprising at least one marker;

(b) detecting and/or quantifying the said markers of each bead and assigning a code, such as the result of a determination of the location of spatially encoded microparticles or vacuoles, for each bead;

(c) identifying beads having distinctive codes; and optionally (d) identifying beads having similar codes; and further optionally (e) sorting the beads having distinctive codes from the beads having non-distinctive codes to thereby provide a plurality of encoded beads.

There is also provided the use of such a composition comprising a plurality of encoded beads linked to a bioactive compound for identifying bioactive compound binding partners, and a use of the composition of beads linked to different bioactive compounds for diagnostic purposes, wherein the binding and determination of a predetermined binding partner to a substrate or bioactive compound on the carrier is at least indicative of a positive diagnosis.

Preferred embodiments of the present invention is disclosed in the drawings and in the below detailed description of the invention.

DEFINITIONS

Figure 1:
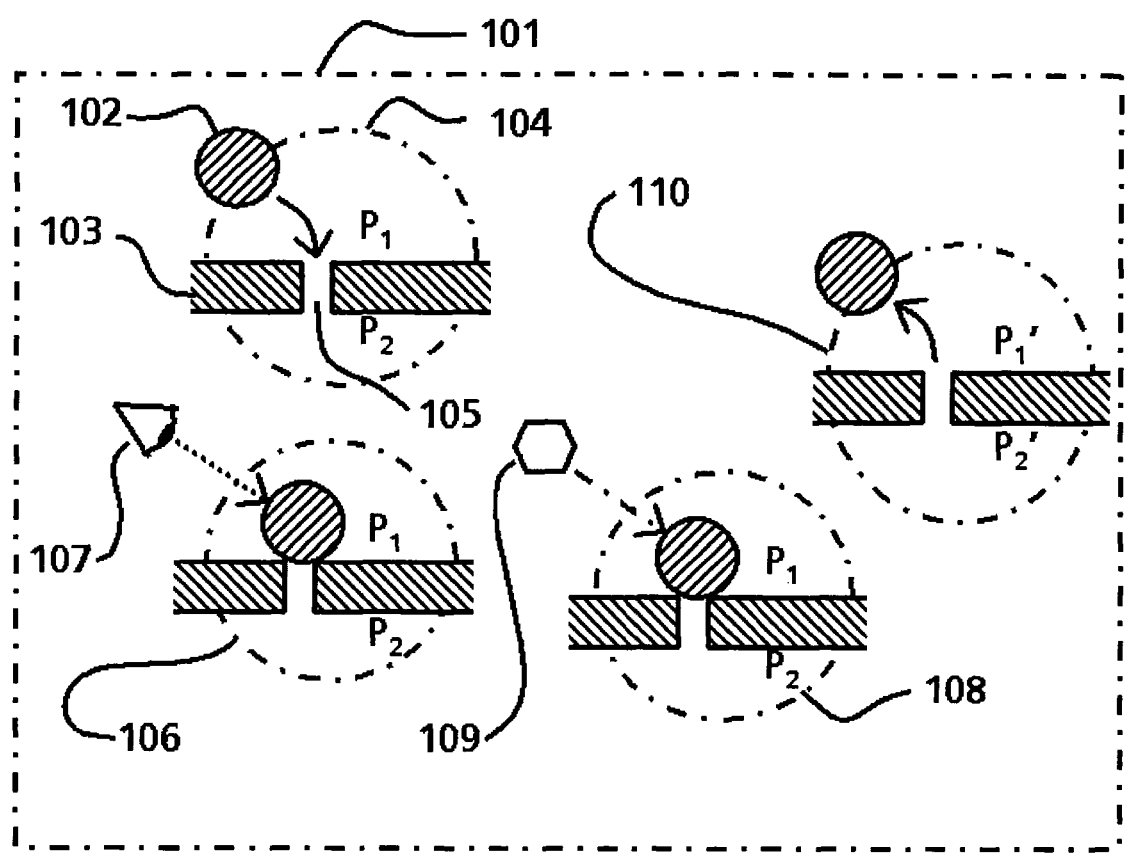
FIG. 1. illustrates the principle of the present invention: 101 dispersion liquid, 102 bead, 103 capture body, 104 loading section (P1>P2), 105 capture hole, 106 measuring section (P1>P2), 107 means for measuring, 108 treating section (P1>P2), 109 means for treating, 110 unloading section (P1'<P2').
Figure 2:
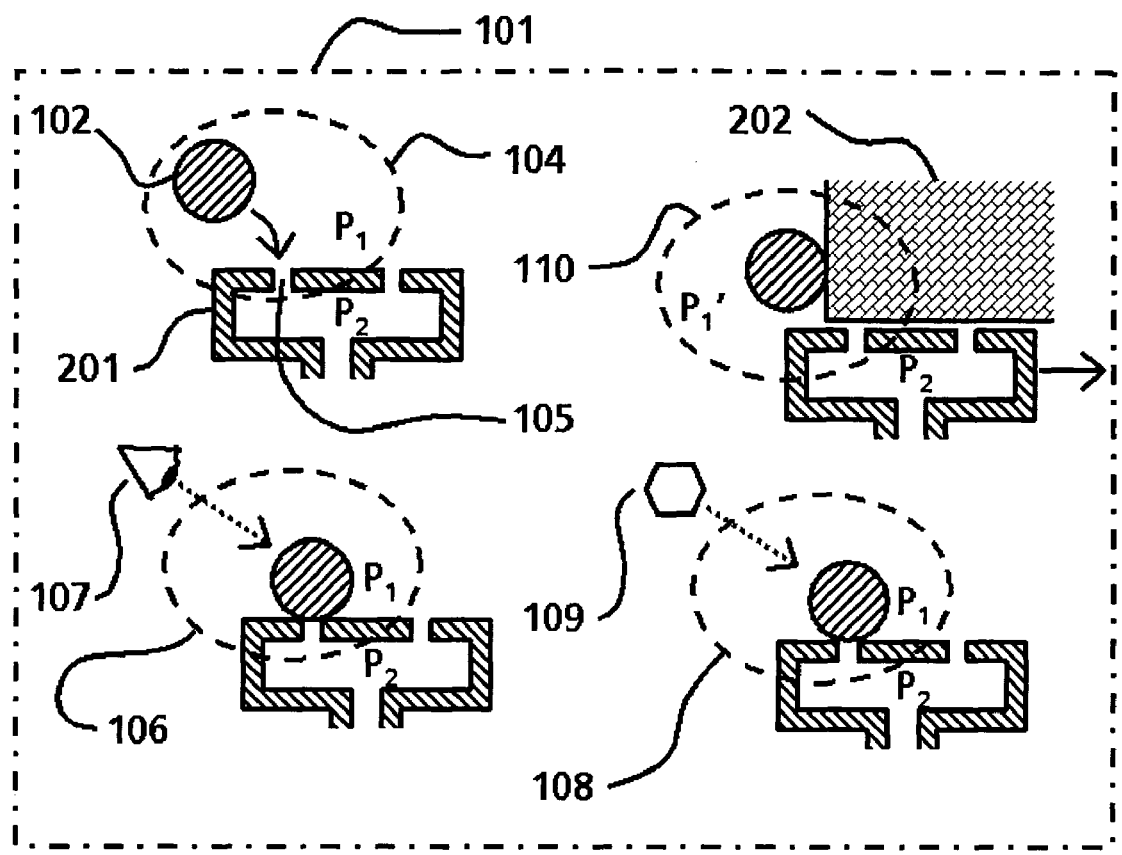
FIG. 2. illustrates the principle of using a vacuum container: 201 vacuum container, 202 bead stopper.

Bead: A bead is an essentially spherical solid particle with a diameter in the range 0.05 mm to 5 mm, and more typically in the range 0.1 mm to 1 mm. Beads can comprise in principle any solid material, but typical materials are silica and polymers, especially cross-linked polymers that can be used for solid phase synthesis, such as cross-linked polystyrene or polyethylene glycol.

Bioactive compound: Molecules comprising a sequence of building blocks, which includes e.g. L-amino acids, D-amino acids, or synthetic amino acids, such a beta-amino acids, as well as natural and non-natural nucleotides and polynucleotides, and carbohydrates. It will also be understood that different basis sets of building blocks may be used at successive steps in the synthesis of a compound of the invention.

Carrier: Used interchangeably with bead.

Code: Used interchangeably with the unique nature of individually identifiable beads, the identification of which resides in the unique spatial distribution of a plurality of microparticles or vacuoles. The code for each bead in principle is unique.

Coordinates: The coordinates are relative spatial coordinates assigned to microparticles in the bead 2 D-coordinates: these are coordinates of microparticles in a 2-D projection of the bead along one of three orthogonal axes.

Dispersion: Heterogeneous fluid comprising beads and dispersion liquid.

Dispersion liquid: A liquid for dispersing of beads.

Encoded bead: This is bead formed by polymerisation of a monomer mixture comprising a dispersion of microparticles.

Essentially: This term signifies that a physical process often yields a result that deviates from the theoretical result expected due to heterogeneity and incomplete control of the process.

Essentially mono-disperse size distribution: This indicate that a slight tendency towards inhomogeneous bead size or microparticle size can be expected in any process for preparation of beads and microparticles respectively.

Essentially spherical: Any spherical object for which the distance from the gravitational centre to any point on the surface of the object is in the range of from a quarter of the average distance from the gravitational centre to the surface to preferably less than four times the average distance from the gravitational centre to the surface.

Essentially the same diameter: The diameters are never identical since a gaussian distribution of bead sizes is obtained during polymerisation Fluorescently detectable: An unsaturated organic molecule, a complex, an alloy or a transition metal that is excited at one wavelength and, due to electronic structure and heat emission, returns to the ground state with the emission of a photon at a different wavelength, wherein said emission can be detected.

Granulation: Process whereby a solid body is mechanically broken into smaller fragments.

HYDRA: PEG-tri-aminoethylamine star copolymer.

Individually detectable: This refer to the separation of beads in a fluidic stream of beads that allow recording of the encoding pattern of each individual bead.

PEGA: PEG-acrylamide copolymer (may be alkylated on amide)

Photon fluorescence spectroscopy: One photon fluorescence spectroscopy, which is the same as standard fluorescence spectroscopy, is based on the facts that a molecule can be excited by a single photon, and that the excited molecule after a internal process emits a photon with a lower energy than the excitation photon. The energy (the spectrum) as well as the rate of emission is specific for the molecule in its specific environment. Two-photon excitation of fluorescence is based on the principle that two photons of longer wavelength light are simultaneously absorbed by a fluorochrome which would normally be excited by a single photon, with a shorter wavelength. The non-linear optical absorption property of two-photon excitation limits the fluorochrome excitation to the point of focus.

POEPOP: Polyethyleneglycol-polyoxypropylene copolymer

Resolution: This term refers to the resolution of a detection method, in a CCD framegrap this is defined by the number of pixels and the optics used to produce the picture, in a scanning laser detection this relates to the cross-section of a laser beam at the point of excitation.

Solid phase synthesis: Synthesis where one of several of the reactants forming the target molecule is attached to a solid support e.g. a bead.

Spatial position: Position of a bead or microparticle in space defined by Cartesian coordinates Spatially immobilised microparticles: Microparticles which are immobilised in a surrounding polymer matrix in such a way that the individual distances between the immobilised microparticles are constant in a given solvent.

SPOCC: Polymer obtained by ring opening polymerisation of partially or fully 3-methyloxetan-3-ylmethyl alkylated PEG.

Swelling: When beads or microparticles or vacuoles are capable of swelling, any physical measurement of the aforementioned, including size determinations and volume determinations, refer to measurements conducted for the swelled bead or microparticle or vacuole. Swelling of the beads are for practical reasons measured as the volume of a packed bed of beads swelled in a specific solvent and divided by the dry weight of the beads. The unit is given as ml/g. Typical solvents are water, methanol and dichloromethane, but any suitable solvent may be chosen. When the refractive index of the swelled bead is different from the refractive index of the surrounding solvent the swelled bead will function as an optical lens. When the relative positions of immobilised microparticles inside the swelled beads are determined by optical means this lens effect may give rise to inaccurate determination of the relative positions of the immobilised microparticles. Preferred solvents give rise to as little difference in refractive index between the solvent and the swelled bead as possible. For instance when the polymer matrix comprises cross-linked polyethyleneglycol a one-to-one mixture of ethanol and glycerol gives rise to nearly no refractive index difference.

Unique distance matrix: Each bead is uniquely identified by an orientation independent distance matrix describing the relative positions of microparticles within the encoded bead.

Uniquely identifiable: Used herein interchangeably with "individually identifiable", i.e. that a single bead can be identified on the basis of the spatial configuration of the microparticles immobilised in the bead. The encoded beads are "individually identifiable" within the limits of statistical probability of occurrence of identical beads and resolution of identification method. In one embodiment, with a practical resolution of 1:100 and only 4 encoding microparticles the probability of e.g. selecting two identical beads is $10^{-6}$ according to Monte-Carlo simulation. A total of $\sim 10^{15}$ different beads may be encoded. More preferably, more than 95%, such as more than 97%, for example about or more than 98%, such as about or more than 99% of all beads will be "individually identifiable" under practical circumstances.

Vacuole: Space comprising gaseous or liquid composition of matter, wherein said matter is identifiable by having at least one spectroscopically or optically detectable parameter which distinguishes the vacuole from the bead. Vacuoles may be present in e.g. polymer particles instead of microparticles.

DETAILED DESCRIPTION OF THE INVENTION

The present invention in a preferred embodiment provides an apparatus comprising devices for bead manipulation and bead measurement.

The bead manipulation device preferably comprises a mechanical bead handling apparatus comprising a vacuum container comprising a capture disc for bead manipulation.

Once captured onto the capture disc of the vacuum container the beads can be measured, e.g. by using an imaging device capable of generating an image of each bead which can be used for bead identification. The generated images can be stored on a data storage medium and analysed by an analysis device for analysing the results generated by the imaging device. Accordingly, the apparatus can further comprise a device for bead analysis based on the data generated by the imaging device. In an even further embodiment the apparatus can also comprise a device for bead processing based on the data generated by the imaging device and/or the data generated by the analysing device.

The principle of the operation of the apparatus according to the present invention is illustrated in FIG. 1. A bead (102) is dispersed in a dispersion liquid (101) and brought into proximity of the capture body (103), preferably in the form of a disc. The bead is placed firmly on top of a through-going inlet (capture hole) (105) due to the formation of a pressure drop, $P_2-P_1$, over the inlet.

The circular capture body (103) can be manipulated, such as rotated in a step-wise fashion, so that a bead, once it has been firmly fixed onto an inlet, can be transferred to a measuring (imaging) section (106) where one or more properties of the bead can be measured by a suitable device for measuring said one or more properties (107). The measuring section and the measuring device will preferably be stationary, whereas the step-wise motion of the capture disc will transfer—in a step-wise fashion—beads to the measuring section, one bead after the other. Accordingly, the term "section" as used herein will be understood to refer to a particular volume that contains the full track of the capture holes or parts thereof, and through which at least one capture hole can be manipulated. By the "track of the capture holes" is meant the spatial geometry described by the moving capture holes. In the case of a rotating capture disc with capture holes arranged along a circle centered around the axis of rotation of the capture disc, the track of the capture holes is a circle. In preferred embodiments of the present invention a section contains only parts of the track of the capture holes, and preferably all capture holes can be manipulated through a section. In cases where an apparatus of the present invention includes a guiding plate, a section typically is fixed relative to the guiding plate. In cases, where the guiding plate comprises a guiding channel, a section typically refers to a volume including a specific part of the guiding channel. Accordingly, any bead which is measured by the measuring device is positioned in a measuring section. The beads are preferably measured in stationary mode, i.e. in between the step-wise motions which are required in order to rotate the capture disc and transfer beads from one section (e.g. a loading section) to another section (e.g. a measuring section).

It is to be understood that the capture body can be of various geometries other than circular and can be manipulated in various ways other than rotation. As an example the capture body can be spherical with capture holes arranged along a circle and can be rotated around and axis perpendicular to the geometrical plane of the capture holes and going through the centre of the circle described by the capture holes. As a further example a capture body can comprise a rectangular capture surface with a rectangular array of capture holes arranged in rows and columns, and can e.g. be manipulated in directions parallel to the rows and columns of the capture holes. Furthermore the loading and/or unloading can be performed batch wise. As an example, a capture body can be loaded with beads by immersing the capture surface of the capture body into a dispersion of beads, and can be unloaded by immersing the capture surface in dispersion liquid and disconnecting the vacuum body from the vacuum and optionally connecting the vacuum container to a pressurized source of dispersion liquid.

Examples of suitable measuring devices are e.g. imaging devices, such as microscopes, CCD-cameras, confocal microscopes, scanning laser microscopes, non-imaging devices, such as photo-multiplier tubes, and spectrophotometers, such as infrared spectrometers, ultraviolet spectrometers, UV-VIS spectrometers, and Raman spectrometers.

The properties measured can optionally be analysed further by a device suitable for analysing the results generated in the measuring section.

Examples of suitable analysing devices are e.g. computers with computer programs installed. Suitable computer programs can comprise but are not limited to computer programs for image processing, such as finding bright dots, for extracting the three-dimensional positions of bright dots from orthogonal fluorescence image pairs of spatially encoded beads, for metric calculations, such as determining the distance matrix between bright dots from the three-dimensional positions of dots, and for identifying individual spatially encoded beads on the basis of the distance matrix as described elsewhere. Further examples are programs for comparing total bead fluorescence against a preset value, generating a sorting result on the basis of the comparison, for keeping track of the position of beads and their associated sorting results, and for controlling an actuator of an optional sorting section of an apparatus of the present invention. Furthermore, computer programs can control the means for treating a bead in one or more optional treating sections of the present invention, such as keeping track of synthesis beads and their individual predetermined building block exposure sequences and control the addition of specific building blocks to said one or more optional treating sections in accordance thereto.

Once a bead has been subjected to a measuring step and a particular property has been measured, and optionally also analysed, the capture body can be further manipulated, such as rotated, preferably in the same orientation as previously, so that a bead having been measured and optionally also analysed, subsequently enters a processing section (108) where the bead can optionally be processed by a suitable processing device (109).

Examples of suitable treating devices are e.g. lasers for etching or bleaching, compartments connected to the treating section by tubes for infusion of chemical and/or biological compounds for performing chemical reactions, heating devices, ultraviolet lasers, or lamps for accelerating a desired chemical reaction. As an example a compound can be added that reacts with a specific chemical group if present in the bead upon the formation of a fluorescent compound, e.g. a short lived fluorescent compound. The presence or absence of the specific chemical group is then determined in a downstream measuring section by total fluorescence measurement.

By bleaching is meant a process whereby the colour and/or fluorescence of a material be reduced or eliminated. As an example a fluorescent and/or colour bead can be given a specific mark for purposes of e.g. keeping track of the bead, by bleaching a certain pattern therein.

By etching is meant a process whereby the microscopic interactions, such as covalent or ionic bonds, Van der Waals forces, hydrogen bonds, and the like, that keep the microscopic entities of a solid material together are eliminated, whereby the material deteriorates. As an example a laser can etch one or more through-going holes in a bead for improved access of large molecules to the core of the bead.

By chemical reaction is meant a process that breaks existing chemical bonds, such as covalent bonds, ionic bonds, or hydrogen bonds, and forms new chemical bonds within a given chemical compound. As an example chemical compounds with a desired structure can be synthesised on beads for solid phase synthesis, so-called synthesis beads, by exposing the beads to building blocks in a specified sequence. As an example the treating device can comprise a plurality of compartments comprising chemical building blocks said compartments being connected to the treating section by at least one tube for diverting individual chemical building blocks to the treating section, such that specific beads can be exposed to specific building blocks in the treating section.

By acceleration of a chemical reaction is meant a process whereby the reaction rate of a chemical reaction is increased. One example of acceleration is initiation, which is a process that increases a specific chemical reaction rate by orders of magnitude without considerably influencing the reaction rate of other chemical reactions. As an example polymer beads comprising carbon-carbon double bonds, such as present in vinyl groups, can be cross-linked by exposure to ultraviolet irradiation.

In a similar and still further step of operating the capture body, the bead can be transported to an unloading section (110) by suitable manipulation of the capture body. The bead in question can be removed from the capture body e.g. by reversing the pressure drop having been exerted during the aforementioned steps, i.e. by reversing—once the bead enters the unloading section—the pressure drop $P_2'-P_1'$ over the inlet to which the bead has been attached during the abovementioned operations.

The bead sorting and imaging apparatus described in principle above allows a fast and reliable sorting, imaging and identification of a plurality of polymer beads. Using the bead sorting apparatus disclosed herein it is possible to perform methods enabling an imaging in a single hour of as many as more than 10.000 beads, such as more than 20.000 beads, such as at least 30.000 beads, such as at least 36.000 beads, such as at least 76.000 beads per hour, with imaging exposure times of about 1/20 second or less. Imaging exposure times in this range are orders of magnitudes longer than the approximately 10 microseconds exposure times allowed for by a purely fluid dynamics based systems.

Furthermore, the sensor for detecting the coming of a bead, which is an essential component of the purely fluid dynamics based system, is rendered superfluous by the present invention due to the accurate mechanical control of the capture body being operated by a stepper motor.

Figure 9:
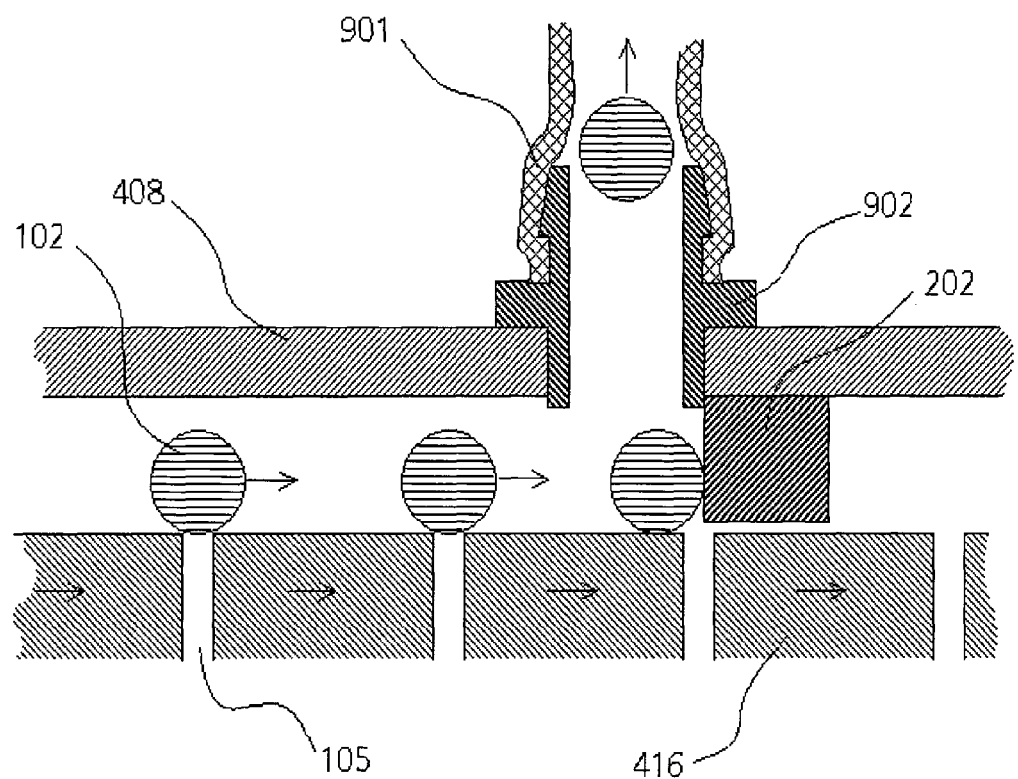
FIG. 9. shows an unloading section for removing beads from the capture body by use of a bead stopper: 901 tube, 902 connecting piece.

FIG. 1 discloses the principle of attaching a bead to a through-going inlet of a capture disc and transferring the bead to certain (stationary) "utility sections" by rotating the disc. In a preferred embodiment of the present invention, as illustrated in FIG. 9, the capture body forms part of a (capture) vacuum container (903) connected to a vacuum so that an essentially constant pressure, $P_2$, can be maintained inside the capture vacuum container throughout the operation of the apparatus. The capture vacuum container ensures that the capture body surface can be moved freely around a central axis with only a minimum of friction.

The vacuum container comprises a first (outer) surface onto which beads can be captured, and through going inlets extending from the first surface to a second (inner) surface.

The captured beads can be transferred between different "utility sections"—defined by fixed positions occupied by different beads over time—when the vacuum container is rotated around a central axis. By "utility sections" is meant sections such as e.g. loading sections, measuring sections, analysing sections, processing sections, and unloading sections.

The beads can finally be removed from the capture vacuum container at an unloading section (110) by rotating the capture vacuum container so that a bead on the first surface is contacted by a bead stopper (202) which forces the bead away from the first surface of the capture vacuum container. The use of a bead stopper eliminates the need for supplying a strong vacuum near the first surface of the capture vacuum container at the unloading section.

In one aspect of the invention there is provided a vacuum container comprising a) a circular capture disc comprising a plurality of through-going inlets, b) a circular capture disc support supporting the capture disc at a distal end thereof (at the perimeter) and being connected at a proximal end (at the central axis) of the capture disc to c) a hollow shaft, wherein the hollow shaft is preferably fitted with a shaft hole so that a vacuum (i.e. a pressure below 1 bar) can be applied to the interior of the vacuum container, and d) a stepper motor operably linked to a momentum transfer split for transferring the momentum from the stepper motor to the vacuum container, thereby causing the vacuum container to rotate in a controlled, step-wise fashion.

In the above description the pressure drop over the capture disc is generated by applying a vacuum to the interior of the vacuum body. It is to be understood though that the pressure drop can be generated in other ways. One alternative is to apply a pressure to the dispersion liquid contacting the outer surface of the capture disc by e.g. connecting a pressurized dispersion liquid reservoir thereto. A further alternative is to apply a vacuum to the inside of the vacuum container and at the same time to apply a pressure to the dispersion liquid on the outside.

The above-described vacuum container comprising a rotatable capture disc for bead sorting is preferably integrated into an apparatus for bead sorting further comprising the following features i) a bead feeding section for diverting beads to the vacuum container of the bead sorting apparatus, ii) a loading section for loading beads onto the capture disc of the vacuum container, iii) a device for rotating the vacuum container and thereby transferring beads detachably attached to through-going inlets of the capture disc from one location to another location, iv) a measuring section for optically measuring at least one property of a bead attached to the capture disc, v) an optical measuring device for measuring the at least one bead property, vi) an analysing device for analysing and storing the data obtained from measuring the at least one bead property, and vii) at least one unloading section for unloading beads from the capture disc of the vacuum container.

An overview of the apparatus for bead sorting according to the invention is described herein below with reference to FIG. 3.

Overview of Bead Sorting Apparatus

Figure 3:
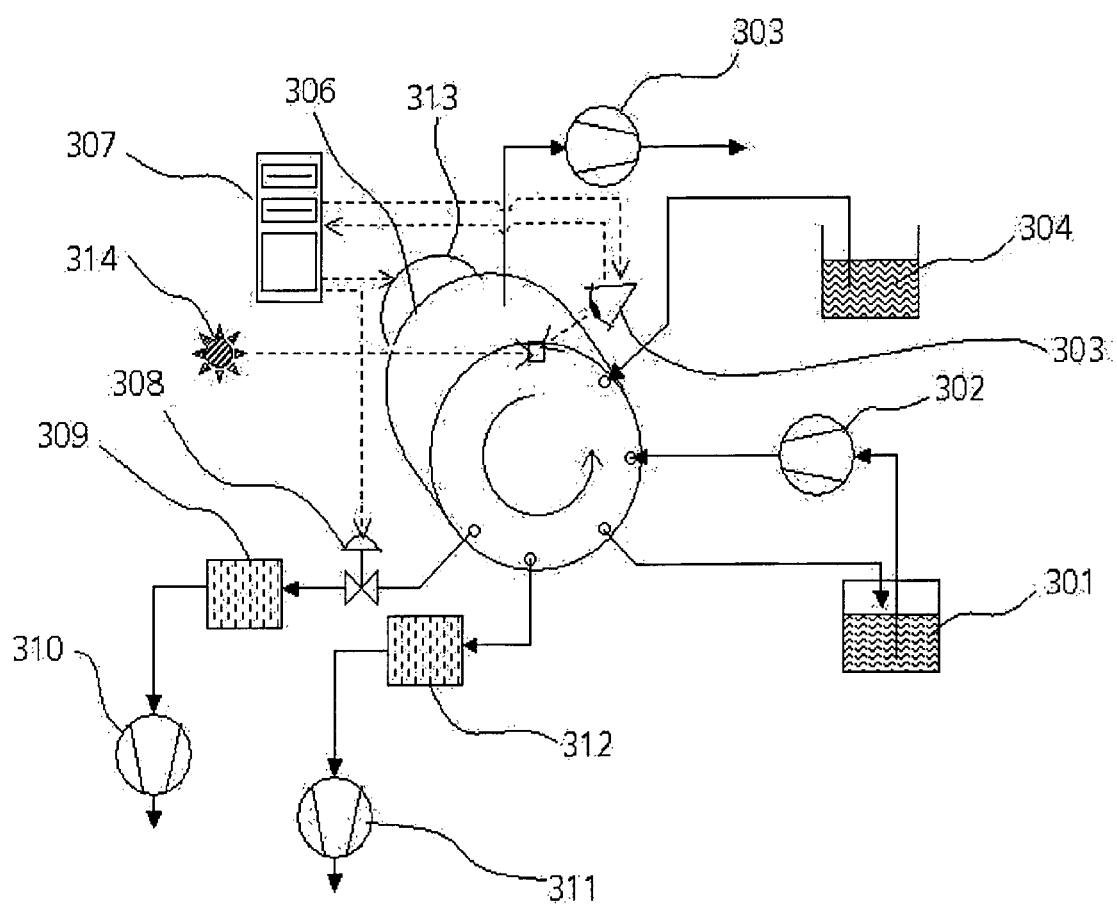
FIG. 3. shows an overview of an apparatus: 301 bead suspension reservoir, 302 bead suspension pump, 303 measuring device, 304 Water reservoir, 305 water pump, 306 Outer cylinder of bead handling apparatus, 307 Computer, 308 valve, 309 first bead filter, 312 second bead filter, 310 third water pump, 311 second water pump, 313 stepper motor, 314 laser.

The following paragraphs describe with reference to FIG. 3 the best mode for operating the bead sorting apparatus of the invention as well as the methods for bead sorting which are thereby enabled.

FIG. 3 illustrates a bead suspension reservoir (301) in which beads to be sorted can be suspended in water by a sufficiently rapid stirring. The beads can be diverted to the bead suspension reservoir e.g. following a solid phase synthesis step. A bead suspension pump (302) supplies the suspended beads from the bead suspension reservoir to the bead feeding section of the apparatus. Any non-captured beads can be re-circulated to the bead suspension reservoir from the excess bead unloading section.

The water reservoir (304) diverts aqueous liquid such as water to the water feeding section of the apparatus. The water in the water reservoir preferably has a free surface for ensuring a water pressure inside the guiding channel of approximately 1 bar.

The first water pump (305) is connected to the vacuum connecting piece of the apparatus for maintaining a vacuum inside the vacuum container. The vacuum ensures that beads remain firmly fixed to the capture disc of the vacuum container during transfer to at least one or more of a measuring section and an analysing section. The transfer occurs when beads having been fixed to the capture disc of the vacuum container by the applied vacuum pressure are rotated in step-wise motions by the action of a stepper motor operated by a computer (307).

An illumination source (314) positioned in the measuring section for illuminating a bead in the measuring section preferably comprises at least one laser. Once a bead has been illuminated by the laser, the image of the bead thereby obtained is recorded by an imaging device (303) and optionally also stored on a data storage medium in a computer (307).

The computer (307), or a set of different computers, can be used for controlling the stepper motor, as well as controlling the imaging device for imaging beads, storing imaging data, analysing the images obtained, and controlling the piston valve at the unloading section.

The imaging device (303) preferably comprises two CCD cameras. Each CCD camera is equipped with an image intensifier, a microscope objective for simultaneous imaging of a bead inside the measuring section, and a fluorescence filter for blocking the laser light and for transmitting fluorescence emission from the beads.

The images obtained are preferably stored on a data storage medium in a computer and analysed with regard to total number of fluorescent microparticles embedded in each bead. An analysis result is generated for each bead stating the number of fluorescence microparticle in the bead. A sorting result is subsequently generated for each bead by comparing the analysis result to a specified interval so that if the analysis result lies within the interval the sorting result=1, whereas, if the analysis result lies outside of the interval, the sorting result=0, Each bead, its associated sorting result, and its position on the capture disc from the measuring section and forward is recorded by a computer.

At the sorting section each bead is removed from the disc and transferred to the second bead filter (309) if its associated sorting result=1, whereas the bead is left on the capture disc if its analysis result=0, At the unloading section all beads that were not removed at the sorting section are removed from the capture disc and transferred to the first bead filter (312), In this way, at least two fractions of beads are generated, one fraction containing beads with a number of fluorescent microparticles within the specified interval, and one fraction containing beads with a number of fluorescent microparticles outside the specified interval.

A third water pump (310) generates a vacuum for removing beads from the capture disc at a sorting section. The removal of beads is ensured by the actions of a piston valve (308) connecting the vacuum of the third water pump to the sorting section. A second filter (309) can retain beads removed at the sorting section. A second water pump 311) generates a vacuum for removing beads not removed at the unloading section from the capture disc at the unloading section.

Operation of the Bead Sorting Apparatus

The below sections describe the actions routinely performed when operating the above-described apparatus.

Initially, the computer (307), the CCD-cameras, and the image intensifiers are turned on. The valve (308) is closed and the water reservoir (304) is filled with demineralised water. The first water pump (304) is activated, whereby a pressure of less than 0.5 bar is maintained inside the vacuum container. The third water pump (310) is started whereby a pressure of 0.1 bar is maintained downstream from the second bead filter (309). The second water pump (311) is started whereby a pressure of 0.1 bar is maintained downstream from the first bead filter (312).

The laser (314) is turned on whereby the measuring section is illuminated. A computer program is run which controls the stepper motor (313), the valve (308), and the CCD-cameras, and the image intensifiers so that the vacuum body is rotated in a step-wise fashion and so that one pair of orthogonal images are obtained, stored, and analysed in the computer every time a capture hole is momentarily at rest in the imaging section. The valve (308) is controlled on the basis of the result of the analysis of the images, thereby enabling sorting of the beads.

Vacuum Container

Figure 4:
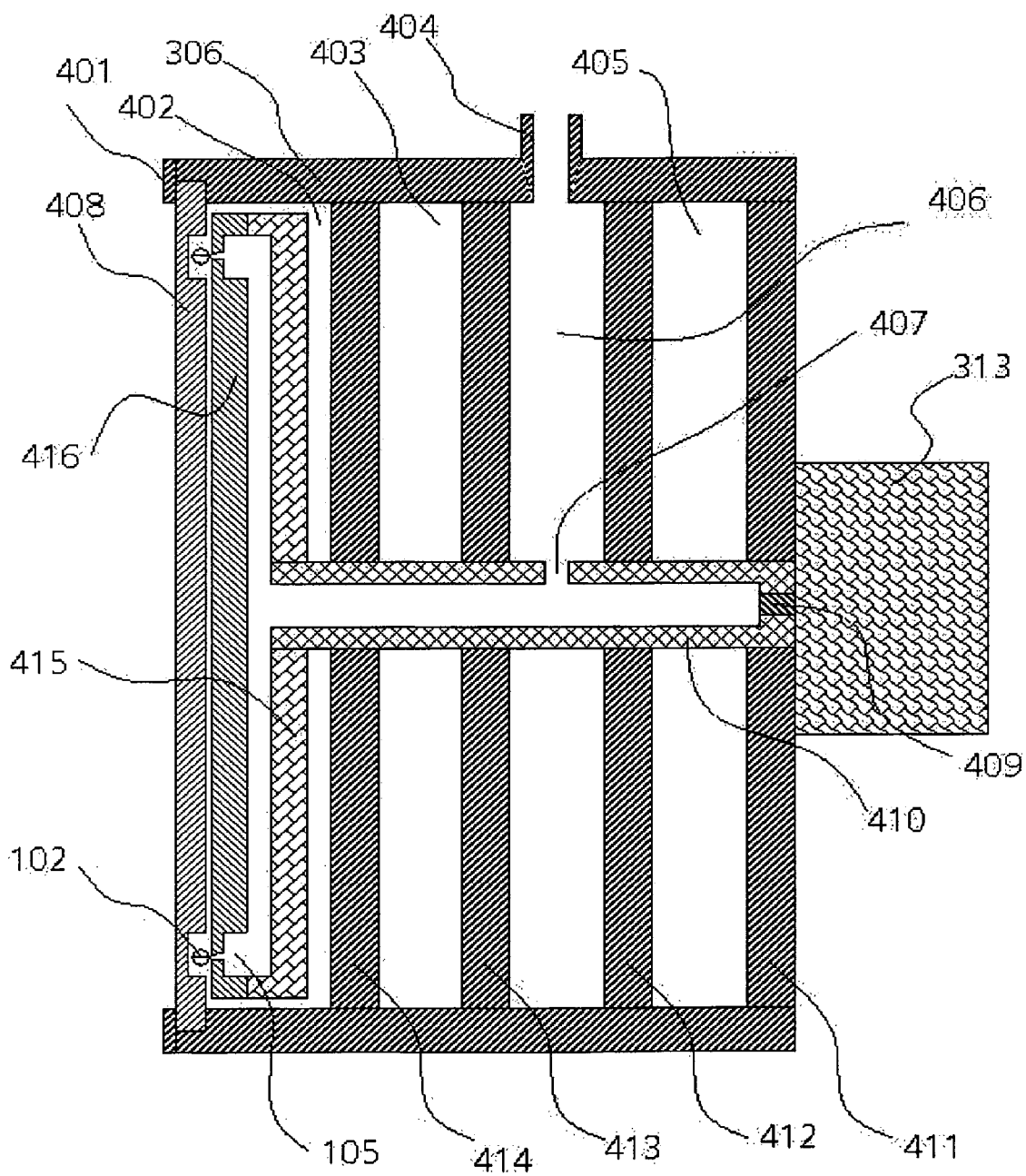
FIG. 4. shows a vacuum container and a vacuum container housing: 401 guiding plate holder, 402, 406 wet sections, 403, 405 dry sections, 404 vacuum connecting piece, 407 shaft hole, 408 guiding plate, 409 momentum transfer split, 410 hollow shaft, 411 back plate, 412-414 separation plates, 415 capture disc holder, 416 capture disc.

A detailed illustration of one preferred embodiment of a vacuum container and a vacuum container housing is provided in FIG. 4. The vacuum container according to this embodiment preferably comprises a) a circular capture disc (416) comprising a plurality of a through going inlets (105) forming a circle close to the perimeter of the capture disc,
such as e.g. a 100 mm diameter and 5 mm thick capture disc with e.g. about 100 cylindrical or conically shaped through-going inlets (capture holes) having the same diameter or different diameters through the disc (depending on whether the inlet is a cylinder or a cone). When being conical in shape, the through going inlets can have a diameter of about 0.2 mm at the first side of the disc, and a diameter of about 2.0 mm at the second side of the disc. The capture holes can e.g. be arranged along an 80 mm diameter circle 10 mm from the perimeter of the disc, b) a circular capture disc support (415),
preferably having an outer diameter of about 100 mm, supporting the capture disc (416) at a distal end and being connected at a proximal end to c) a hollow shaft (410),
preferably a hollow stainless steel shaft, wherein the shaft can have an outer diameter of about 6 mm and an inner diameter of about 4 mm, wherein the hollow shaft (410) is preferably fitted with a shaft hole (407) so that a vacuum (i.e. a pressure below 1 bar) can be applied to the interior of the vacuum container,

Capture Disc Holder of Vacuum Container

A cylindrical capture disc holder (415) makes it possible to apply a pressure drop over the disc. The capture disc holder (415) can have an outer diameter of e.g. 100 mm. The capture disc holder can support the disc at the perimeter of the disc while the central section of the capture disc holder is supported by a hollow shaft (410), preferably a hollow stainless steel shaft, through which shaft one can apply a first vacuum of less than e.g. 0.5 bar. The hollow stainless steel shaft (410) can have an outer diameter of about 6 mm and an inner diameter of about 4 mm.

Vacuum Container Housing

The vacuum container housing according to this embodiment serves the purposes of containing the dispersion liquid, holding the vacuum container in place, connecting the inside of the vacuum container to a vacuum, and transferring rotational momentum to the vacuum container.

The vacuum container housing in one embodiment preferably comprises a) an outer cylinder (303) for containing the dispersion liquid,
b) a vacuum pump connecting piece (404) therein for connecting the wet section (406) of the vacuum container housing to a suitable pump, such as e.g. a water pump for maintaining and controlling the vacuum inside the vacuum container,
c) a guiding plate (408) as illustrated in FIG. 4, and optionally
d) a momentum transfer split (409) operably linked to a stepper motor (313) for transferring the momentum from the stepper motor to the vacuum container thereby causing the vacuum container to rotate in a controlled step-wise fashion.

A suitable means for stepwise rotating the disc is a stepper motor with e.g. 200 steps per round mounted on the shaft and arranged so that the motor causes the disc and the container to rotate around a common central axis. In this way, the capture holes are moved along a planar, circular path. The stepper motor comprises an electronic stepper motor controller for controlling the motion of the stepper motor.

The guiding plate preferably comprises a circular guiding channel, such as e.g. a 1 mm deep circular guiding channel having an outer diameter of e.g. about 81.5 mm and an inner diameter of e.g. about 78.5 mm carved therein, said guiding plate further comprising a number of through-going inlets for supplying and retracting beads, or more preferably dispersion liquid comprising beads, to and from the guiding channel of the guiding plate, said guiding plate preferably further comprising a plurality of transparent sections or windows allowing illuminating and imaging of the beads, wherein the guiding plate is optionally attached to a guiding plate holder (401) for holding the guiding plate.

The at least one transparent section or window is preferably made from a material which does not absorb the illumination light from the source of illumination and/or the emission light emitted from the particles, preferably quartz or a suitable trans-parent polymer.

The vacuum container and vacuum container housing can be constructed in different ways in order to serve the purpose of transferring beads from one section of utility to another. The construction is not critical as long as it permits the container to function according to the principles of the invention. In FIG. 4 is illustrated a design based on a circular back plate (411), such as a circular stainless steel back plate (411), and a plurality of separation plates (412-414), such as circular stainless steel separation plates for separating dry sections (403, 405) from the wet sections (402, 406). The separation plates are preferably fitted with central through-going holes equipped with sealings for keeping the liquid from leaking from the wet sections to the dry sections. The plates are preferably further equipped with low friction bearings for ensuring low-friction and non-wobbling rotation of the shaft.

The individual components of a vacuum container comprising a) a circular capture disc comprising a plurality of a through going inlets forming a circle close to the perimeter of the capture disc, b) a circular capture disc support supporting the capture disc at a distal end and being connected at a proximal end to c) a hollow shaft preferably fitted with a shaft hole so that a vacuum can be applied to the interior of the vacuum container, and of a vacuum container housing comprising d) a stepper motor operably linked to a momentum transfer split for transferring the momentum from the stepper motor to the vacuum container thereby causing the vacuum container to rotate in a controlled step-wise fashion, and optionally further components, is disclosed in the following.

Figure 5:
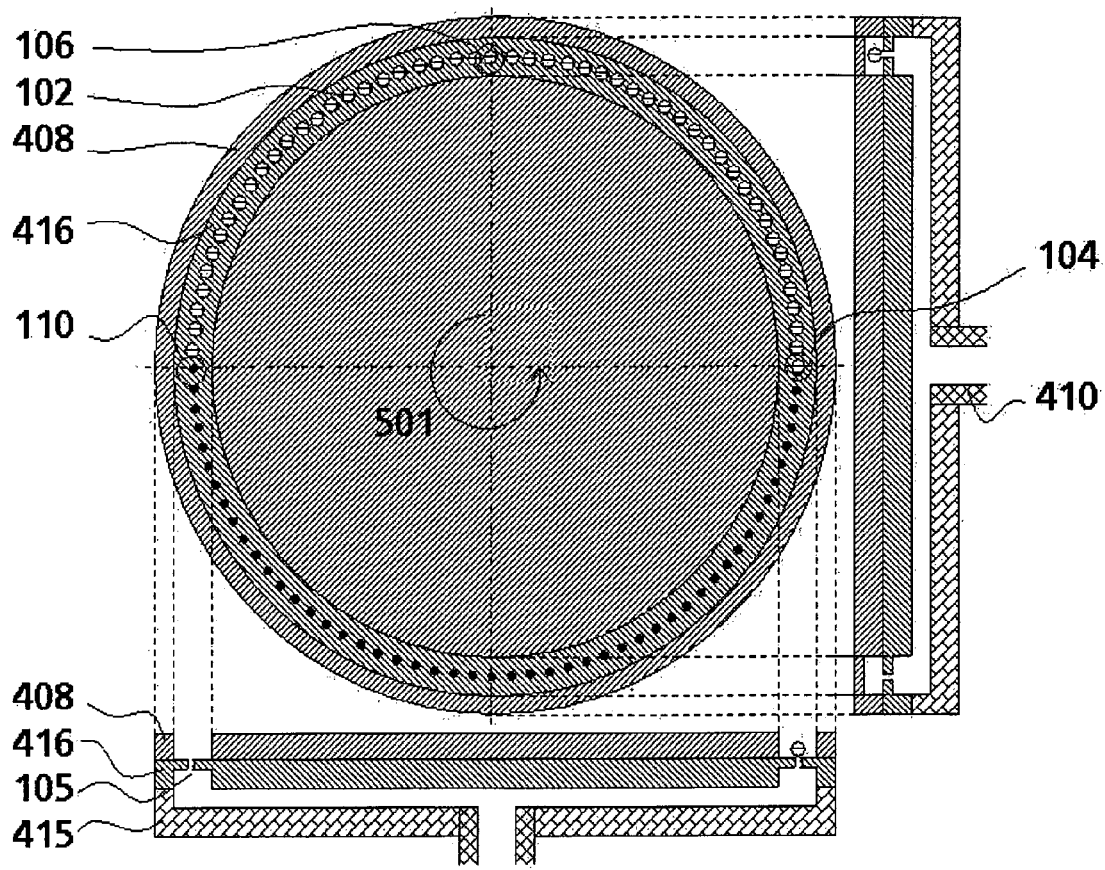
FIG. 5. shows parts of a vacuum container and a vacuum container housing: 501 direction of rotation.

FIG. 5 illustrates detailed side and top views of a capture disc of the vacuum container and vacuum container housing illustrated in FIG. 4.

The capture body (416) can comprise e.g. a 100 mm diameter and 5 mm thick plastic disc comprising two planar, circular sides, a first and a second side. The capture holes (105) can comprise any suitable number of through-going inlets, such as e.g. about 100 cylindrical through-going inlets of varying diameter, the diameter being e.g. about 0.2 mm at the first side of the disc (to which the beads are attached), and the diameter being e.g. about 2.0 mm at the second side of the disc. In a preferred embodiment the number steps of the stepper motor is divisible by the number of capture holes, and the capture holes are equidistantly spaced, whereby it is obtained that all capture holes are at rest at the exact same positions.

The capture holes (through-going inlets) can e.g. be arranged along an 80 mm diameter circle positioned about 10 mm from the perimeter of the disc.

Figure 16:
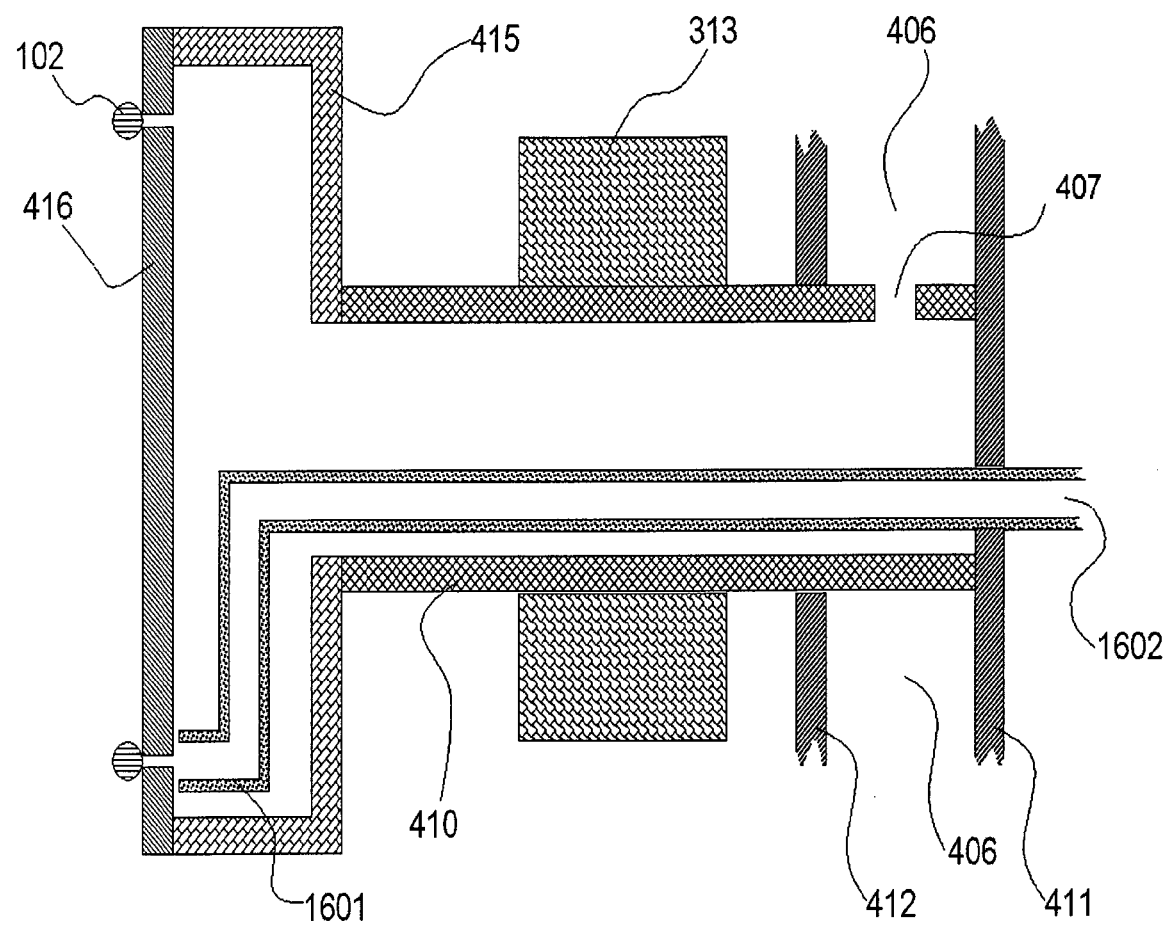
FIG. 16. Rotating vacuum container with hollow shaft stepper motor. 1601 tube for local back pressure control, 1602 inlet to tube for local back pressure control.

FIG. 16 discloses an embodiment wherein the rotating vacuum container is fitted with a hollow shaft stepper motor. 1601 is tube for local back pressure control, 1602 is inlet to tube for local back pressure control.

In one embodiment of the present invention the device for rotating the vacuum container of the apparatus comprises a hollow shaft stepper motor (313), such as an SMH88.1.M supplied by STÖGRA Antriebstechnik GmbH, München, Germany. In a further embodiment of the invention a tube (1601) having an inlet (1602) is positioned inside the rotating vacuum container and being fixed by the back plate (411) such that said tube does not rotate when the vacuum container is rotated. The tube has its outlet close to the back of the capture disc (416), such as 0.1 mm or less from the capture disc, or contacting the capture disc. Said outlet of said tube is positioned such that the capture holes pass said outlet of said tube when the vacuum container is rotated. Said outlet of said tube is further positioned such that the capture holes are at rest at said outlet in between the step-wise rotation of the vacuum container induced by the stepper motor. Hereby it is obtained that the pressure drop across a capture hole positioned at said outlet of said tube can be controlled independently of the pressure drop across the remaining capture holes by applying a pressure or a vacuum to said inlet of said tube. As an example an inverse pressure drop, i.e. higher pressure on the back of the capture disc than on the front of the capture disc, i.e. $P_2' > P_1'$ (see FIG. 1) can be generated in a confined region of the capture disc, e.g. across one single capture hole. In a preferred embodiment of the present invention said outlet is positioned in the unloading section of the apparatus and a pressure is applied to said inlet of said tube. Hereby it is obtained that a captured bead be released in the unloading section due to the local inverse pressure drop induced by the tube. In one embodiment of the present invention said outlet of said tube covers two or more capture holes, whereby it is obtained that the pressure drop across said two or more capture holes can be controlled independently of the pressure drop across the remaining capture holes. In a preferred embodiment of the present invention said outlet of said tube is positioned in the unloading section of the apparatus and covers more than two capture holes, e.g. 10 capture holes, whereby it can be used for effectively releasing beads from the capture disc in the unloading section. In a further embodiment of the present invention two tubes are placed inside the vacuum container, the outlet of first of said two tubes being positioned in the sorting section of the apparatus and the outlet of second of said two tubes being positioned in the unloading section of the apparatus, whereby it is obtained that beads can be removed from the capture disc in the sorting section or in the unloading section on demand.

In addition to tubes for locally controlling the pressure drop across the capture disc the use if a hollow shaft stepper motor allows for various further stationary devices to be inserted into the rotating vacuum container. As an example a mechanical device, comprising a cylinder, said cylinder having a diameter less than the minimum diameter of the capture holes, and means for manipulating said cylinder in its longitudinal direction and perpendicular to the capture disc, can be placed such that the cylinder can penetrate one capture hole in the time between the step-wise rotation of the capture disc. Said cylinder can be used for cleaning possible blocked capture holes. As a further example of stationary devices a light source can be placed inside the rotating vacuum container and positioned such that light shines through one or more capture holes. The spectroscopic properties of the beads can then be measured with a photo-sensor positioned in the guiding plate (408) across the light source.

Utility Sections of the Apparatus for Bead Sorting

Loading Section

The loading section (104) can comprise a volume of e.g. at least 1 mm$^3$, said volume being confined in an essentially cylindrical space extending from the surface of the first side of the disc and into the dispersion liquid and positioned at the circle described by the capture holes.

In a preferred embodiment the loading section comprises an elongated volume extending along the track of the capture holes for a distance corresponding to several times the average distance between neighbouring capture holes, such that at all times during the operation of the apparatus multiple capture holes, such as at least ten capture holes, are contained in the loading section, whereby the probability of a capture hole capturing a bead while traversing the loading section is increased compared to the case of a loading section containing only one capture hole at a time. In order to further increase the chance of capture holes capturing a bead inside the loading section the number of mobile beads in the loading section should be maximised. By "mobile beads" is meant beads that can be captured by a an empty passing capture hole by action of the flow of dispersion liquid towards the capture hole. At low numbers of beads (the bead number) the number of mobile beads (the mobile bead number) increases with increasing bead number up to a certain critical bead number, the clogging bead number, where beads become immobilised by friction and adhesion interactions with neighbouring beads and with the solid surfaces surrounding the loading section. Hence, the bead number in the loading section should be kept just below the clogging bead number. It should be noticed then, that the clogging bead number depends on various parameters, such as e.g. bead size, bead composition, dispersion liquid composition, dispersion liquid flow velocity, and loading section geometry. To avoid the bead capture rate from becoming the throughput limiting factor in the operation of the apparatus the mobile bead number should be maximised.

As already mentioned, the mobile bead number can be increased by increasing the clogging bead number. As an example this can be achieved by inducing static flow in the loading section, e.g. by stirring, such as stirring with a magnetic stirrer, or by infusing dispersion liquid at one end of the loading section and withdrawing dispersion liquid from the distal end of the loading section. In many cases a more pronounced effect can be achieved by inducing an alternating flow field.

A further obvious way of increasing the mobile bead number is to extend the loading section along the track of the capture holes. Obviously the length of the loading section is limited by the total length of the track of the moving capture holes. In the case of a circular capture hole track the total length of the capture hole track can be increased by increasing the diameter of the capture hole track. In cases where the capture holes are arranged along a circle in a capture disc the total length of the capture hole track can be increased by increasing the diameter of the capture disc. If for instance a 500 mm capture disc be used, a total of up to 500 capture holes can be arranged along a circle with 3 mm between neighbouring capture holes. The loading section can then be designed such that at least 400 capture holes be present in the loading section at all times during operation. This significantly increases the probability of a capture hole capturing a bead in the loading section compared to the case of a 100 mm diameter capture disc with the same inter-capture hole distance.

The unloading section (110) preferably also comprises an at least 1 mm$^3$ essentially cylindrical space extending from the surface of the first side of the disc and into the dispersion liquid and positioned at the circle described by the capture holes at e.g. 1800 from the loading section.

Unloading Section

Once the beads have passed through the measuring section (106) and an analysis section (607), they need to be unloaded from the capture disc. In the embodiment disclosed in FIG. 4 one unloading section (606) is illustrated, which serves to unload beads. A detailed disclosure of a preferred embodiment of the unloading section is provided in FIG. 9. Also, an unloading section (110) is illustrated in FIG. 5 opposite to the loading section (104) in the illustrated embodiment.

When a bead enters the unloading section it is firmly fixed onto a through-going inlet of the disc due to the pressure drop over the inlet. Any type of pressure controlling equipment can be used in an unloading section for normalising the vacuum or, preferably, for generating a reverse pressure drop over the part of the disc which at any one time is positioned in the unloading section. The pressure controlling equipment can e.g. comprise a pipe for unloading beads, preferably of stainless steel, having a length of e.g. about 20 mm and an inner diameter of e.g. about 1.1 mm.

The pipe comprises a first end and a second end, and the pipe is preferably positioned perpendicular to the first side of capture disc, the first end of the pipe pointing towards the first side of the disc and being positioned about 1 mm from the capture disc and entering the unloading section, the second end of the pipe being connected to a second vacuum of 0.1 bar, whereby a reverse pressure drop, $P_1'-P_2'=-0.4$ bar, is generated over the capture disc at the unloading section, The measuring section can be defined by a 1 mm³ spherical space extending from the surface of the first side of the disc and into the dispersion liquid. The measuring section (106) for measuring at least one bead property, and optionally also analysing the data resulting from the measuring, is preferably positioned on the circle perimeter defined by the capture holes at an angle of 90° from both the loading section (104) and the unloading section.

Accordingly, beads are transferred from the loading section via the measuring section to the unloading section. The measuring section is so positioned that the step-wise rotation of the disc causes a through-going inlet (capture hole) to which a bead is fixed to be stationary (i.e. not moving) when the bead fixed to the through-going inlet passes the measuring section. This ensures that individual beads can be measured in "stationary mode" during the movements generated by the stepper motor.

The apparatus for measuring individual beads comprises a light source for illuminating a single bead when the bead is positioned in the measuring section, and one or more sets of objectives and cameras for obtaining images of the beads from one or more angles. This is further illustrated in FIG. 8.

Figure 6:
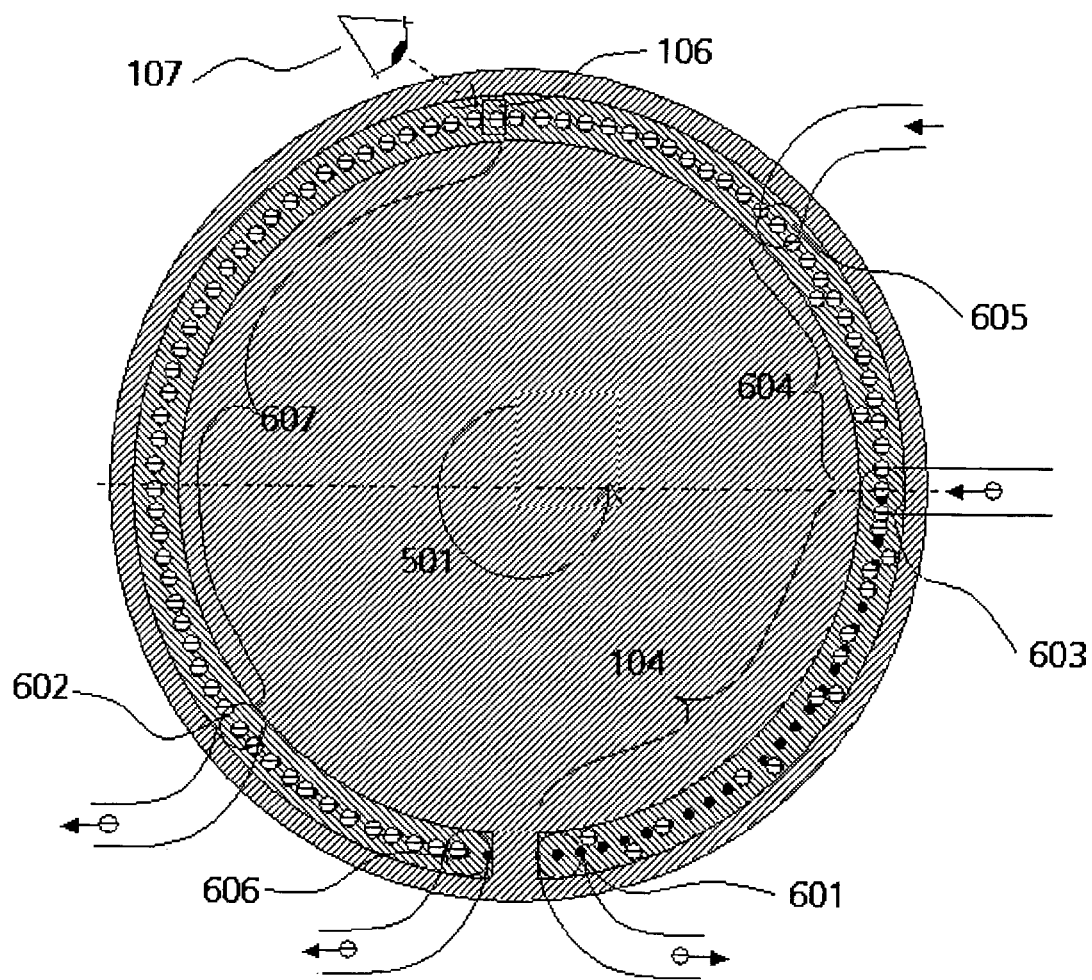
FIG. 6. shows sections of an apparatus: 601 excess bead unloading section, 602 sorting section, 603 bead feeding section, 604 excess bead flushing section, 605 water feeding section, 606 unloading section, 607 analysing section.

The different sections of the bead sorting apparatus is illustrated in more detail in FIG. 6. It will be understood that the term "section" can refer to a part of the capture disc when said part is positioned in a predetermined location with respect to e.g. the stationary devices used for measuring, analysing and the like, including a predetermined stationary location, as the disc is rotated in a step-wise fashion during the operation of the apparatus.

With reference to FIG. 6, the sections of utility can be e.g. a loading section (104), a measuring section (106), an analysis section (607), and at least one unloading section (602, 606).

For example, the through-going capture inlet n will initially be located in the loading section for being loaded with a bead.

As the stepper motor rotates the disc a single step, the through-going capture inlet n will be rotated one step in the orientation of the rotation. At the same time, the through-going capture inlet n+1 will be located in the loading section for being loaded with a bead.

As the stepper motor rotates the disc another single step, the through-going capture inlet n+1 will be rotated one step in the orientation of the rotation. At the same time, the through-going capture inlet n+2 will be located in the loading section for being loaded with a bead, and so on.

As the stepper motor rotates the disc step-wise, the through-going capture inlet n will be rotated a plurality of steps in the orientation of the rotation. After a certain number of step-wise rotations, the through-going capture inlet n will have been rotated so many steps that it will be positioned in the measuring section.

In the embodiment of the capture disc disclosed in FIG. 6, the beads having been dispersed in a dispersion liquid are brought into contact with the capture disc at a bead feeding section (603) where the dispersed beads are diverted to the capture disc loading section (104), preferably via a guiding channel as illustrated in FIG. 6.

In the loading section (104) the beads are sucked onto the through-going capture inlets of the capture disc, and non-captured beads are removed in an excess bead unloading section (601).

There is also provided a liquid feeding section (605) in which e.g. water can be diverted to the guiding channel generating a flow of water in a direction away from the water feeding section. Also provided in this embodiment is an excess bead flushing section (604) for flushing any non-captured beads away from the flushing section and towards the bead feeding section, whereby it is obtained that only captured beads proceed from the excess bead flushing section towards the measuring section. Examples of non-captured beads include non-captured beads sticking to captured beads, non-captured beads sticking to the surface of the capture disc, non-captured beads sticking to the walls of the guiding channel, and freely flowing non-captured beads. In this way it is ensured that non-captured beads do not pass the water feeding section.

Measuring Section

In the measuring section (106) a measuring device enables the generation of an appropriate imaging of the beads.

Figure 7:
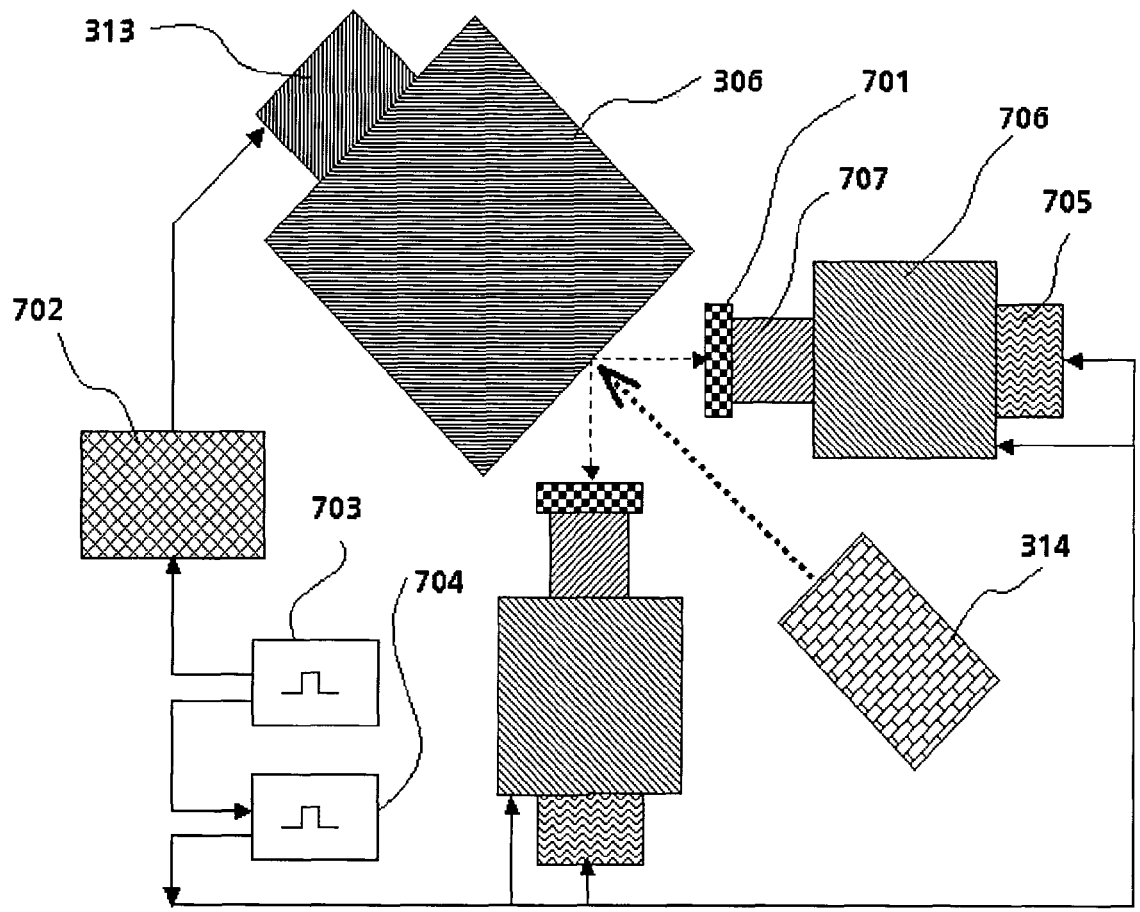
FIG. 7. shows an imaging device for obtaining orthogonal image pairs of beads: 701 fluorescence filter, 702 stepper motor controller, 703 first electric pulse generator, 704 second electric pulse generator, 705 CCD camera, 706 image intensifier, 707 objective.

FIG. 7 illustrates one preferred embodiment for imaging of beads. In this embodiment, the measuring device comprises a stepper motor (313), a stepper motor controller (702), a first electric pulse generator (703), a second electric pulse generator (704), a laser (313), two imaging systems, each comprising a CCD camera (705), an image intensifier (706), an objective (707), a fluorescence filter (701).

Figure 8:
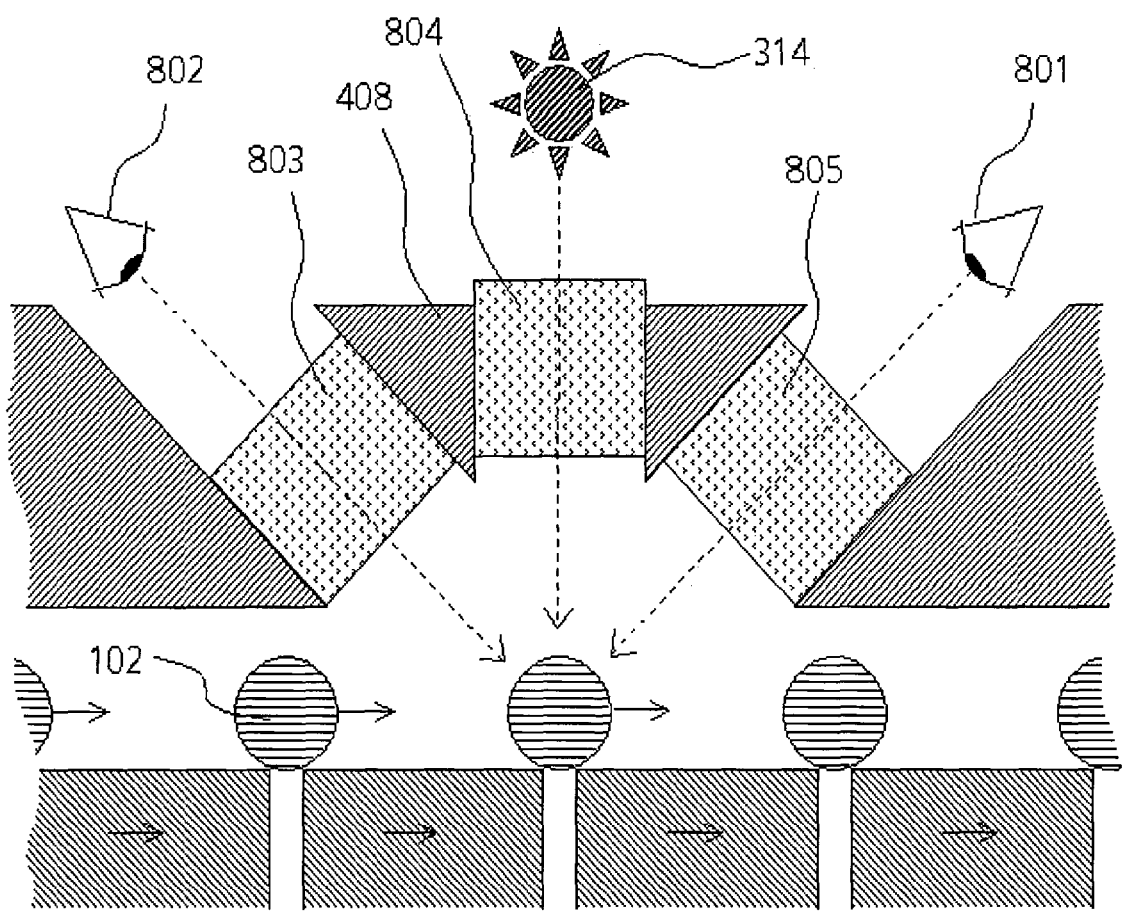
FIG. 8. shows details of a measuring section for obtaining orthogonal image pairs of beads: 801 first microscope, 802 second microscope, 803 second imaging window, 804 illumination window, 805 first imaging window.

FIG. 8 illustrates in detail the set-up of the measuring section according to one embodiment of the present invention.

A first and a second through-going cylindrical imaging hole of a diameter of about 2 mm in the guiding plate is inclined 450 to the plane surface of the guiding plate and arranged perpendicular to each other and further arranged so that their axis cross at a point on the surface of the capture disc at the circle described by the capture holes. This ensures that a bead can be simultaneously imaged from two orthogonal directions through the imaging holes.

First and a second imaging windows are illustrated (801, 803), as well as a through-going illumination hole of a diameter of about 1.5 mm in the guiding plate and perpendicular to the plane surface of the guiding plate and positioned so that the axis of the illumination hole goes through the point at which the axis of the imaging holes cross, whereby a bead can be simultaneously illuminated and imaged.

The illumination window (804) preferably comprises a polished glass cylinder of a diameter of about 1.5 mm and a length about 2 mm inserted, and optionally fixed with a glue, in the illumination hole, whereby the illumination hole is sealed.

The measuring device is described in more detail herein below

In preferred embodiments of the present invention it is desirable to read distance-encoded synthesis beads at a high rate, i.e. reading at least 10000 spatially encoded beads per hour, preferably more than 20000 spatially encoded beads per hour, such as more than 30000 spatially encoded beads per hour.

The reading of encoded bead must result in data from which the distance matrix of individual spatially encoded beads can be extracted by the device analysing the data generated by the measuring device.

In one preferred embodiment there is provided a device for measuring (recording) and storing at least one image of at least one spatially encoded bead comprising a plurality of beads, said device preferably comprising i) at least one source of illumination, preferably a continuous wave laser, ii) at least one pulse generator, iii) at least one image intensifier, and iv) at least one CCD camera, such as two or more CCD cameras.

The measuring device can comprise or be linked to a computer running a program for calculation of distance matrices for individual spatially encoded beads as disclosed herein below.

The photo-sensor for detecting entry of an encoded bead into the imaging section of the flow cell preferably comprises an optical objective for focussing said imaging section of said flow cell onto the photo-sensitive area of said photo-sensor. The optical objective of said photo-sensor preferably comprises a fluorescence filter for blocking the light of said laser, and the fluorescence filter is capable of transmitting the fluorescence emission from an individual encoded bead.

The CCD-camera(s) for recording at least one fluorescence image of an individual encoded bead preferably comprises a gated image intensifier for amplifying the fluorescence emission from the encoded bead. Each of the gated image intensifiers preferably comprises an optical objective for focussing said imaging section of said flow cell onto the photo-sensitive area of each image intensifier. Each optical objective preferably comprises a fluorescence filter for blocking the light of said laser, and the fluorescence filter is capable of transmitting the fluorescence emission from an individual encoded bead.

The pulse generator can be an electrical square wave pulse generator for triggering said two or more CCD-cameras and/or said two or more image intensifiers.

It is preferred that the device further comprises an image storage system comprising one or more of the following elements: A framegrabber for recording the images from said two or more CCD-cameras, an electronic memory-device for storing said images from said framegrabber, a program code for controlling said electronic memory-device, and a computer for integrating said framegrabber and said electronic memory device and for executing said program code.

The bead measuring device can be used in methods for recording and optionally also storing images of individual spatially encoded beads. This is achieved by performing e.g. a method comprising the steps of
1. Dispersing spatially encoded beads in a dispersion liquid,
2. Diverting the dispersion of spatially encoded beads to the capture disc of the vacuum container,
3. Rotating the capture disc and transferring the beads one by one to the measuring section,
4. Recording one pair of orthogonal fluorescence images of each spatially encoded bead, and
5. Optionally storing the images of each spatially encoded bead on a computer, The measuring device preferably comprises:
1. A continuous wave laser for illuminating said imaging section of the measuring device.
2. Two or more video-cameras for obtaining fluorescence images of an encoded bead, each one of said two or more video-cameras being equipped with one gated image intensifier for amplifying the fluorescence emission from the encoded bead, and each one of said image intensifiers being equipped with one optical objective for focussing said imaging section of said flow cell onto the photo-sensitive area of each image intensifier, and each optical objective being equipped with one fluorescence filter for blocking the light of said laser, and said fluorescence filter transmitting the fluorescence emission from the encoded bead
3. An electrical square wave pulse generator for triggering said two or more cameras and said two or more image intensifiers The device preferably also comprises an electrical cable connecting the output terminal of said photo-sensor to the trigger input of said pulse generator whereby it is obtained that a square wave pulse is generated when the output voltage of said photo-sensor is above the trigger-voltage of said pulse generator. Also provided are electrical cables for connecting the output terminal of said pulse generator to the input terminals of said two or more video-cameras and said two or more image intensifiers, whereby it is obtained that two simultaneous images are recorded with said two cameras.

The optical objectives of the image intensifiers can optionally comprise means for increasing the depth of field such as e.g. any one or more of
1. phaseplates such as waveplates such as cubic phase modulation masks placed in the lens system [E. Ben-Eliezer, Z. Zalevsky, E. Marom, N. Konforti, J. Opt. A: Pure Appl. Opt. 5 (2003) S164-S169], [E. R. Dowski and W. T. Cathey, Applied Optics, vol. 34, no 11, pp. 1859-1866, April, 1995],
2. high depth of field endoscopes, such as 1 mm perceived depth of field endoscopes, such as 1 mm perceived depth of field rigid endoscopes,
3. a duplicate set of two or more cameras equipped with image intensifiers, optical objectives, and fluorescence filters, each one of said cameras of said duplicate set of cameras being positioned opposite each one of said cameras of said two or more cameras, each of said cameras of said duplicate set of two or more cameras having a different focus plane than said opposite camera of said two or more cameras, whereby it is obtained that a duplicate set of images are obtained with different focal planes, and a microbead which are far from the focal plane of any one of said two or more cameras will be close to the focal plane of said opposite camera of said duplicate set of two or more cameras and vice versa, and therefore will appear sharply in one of the images obtained with two opposite cameras, or 4. means for varying the aperture placed in the lens system, whereby the depth of field can be increased by decreasing the aperture but whereby at the same time the light sensitivity is decreased, thus whereby the best compromise between depth of field and light sensitivity can be obtained, such as means for varying the aperture in the range from 10 mm to 2 mm, whereby the perceived depth of field in an image of field of view of 1.2 mm×1.5 mm can be varied in the range from about 0.1 mm to 0.8 mm when a CCD camera equipped with an image intensifier and a conventional 10× magnification microscope objective is used.

The image storage system preferably comprises:
1. A framegrabber for recording the images from said two or more cameras
2. An electronic memory-device for storing said images from said framegrabber
3. A program code for controlling said electronic memory-device
4. A computer for integrating said framegrabber and said electronic memory device and for executing said program code, and The image storage system can further comprise means for digital decoding of images obtained with the use of
1. phaseplates, as described above, in order to generate sharper images,
2. a sufficiently high depth of field endoscopes, as described above, and
3. opposing cameras, whereby higher depth of field images can be reconstructed.

The continuous wave laser can e.g. be a BluePoint series supplied by Rainbow Photonics, the Cobolt Blue series supplied by Cobolt AB, or the Blue CrystaLaser series supplied by Crysta Laser of wavelength 473 nm for illuminating the imaging section of said central section of said flow cell and for controlling the position and geometry of said imaging section of said central section of said flow cell, The CCD cameras can e.g. be a CPL high speed series supplied by Canadian Photonics Labs Inc., the SR-CMOS series supplied by Vision Research, or the SVS series supplied by SVS-Vistek GmbH, a first and a second CCD camera, and be positioned perpendicular to each other and aligned relative to said imaging section of said central section of said flow cell in such a way that the CCD chips of said CCD cameras run parallel to the flat surfaces of said central section of said flow cell and so that said imaging section of said central section of said flow cell can be projected onto said two CCD chips of said two CCD cameras by optical means described below.

The image intensifiers can e.g. be supplied by Hamamatsu or the Proxifier series supplied by Proxitronic, or the GPM series supplied by Photonicstech, and connected to said two CCD cameras for amplifying the optical signal emitted from the illuminated section of said imaging section of said flow cell.

Two objectives (such as the MS-50 supplied by MEIJI TECHNO or the QM-100 supplied by Questar) are preferably connected to said first and second CCD cameras whereby the optical signal from said imaging section is focused onto said two CCD chips of said two CCD cameras.

Two optical filters (emission band pass filters, e.g. type 528-50 supplied by Ferroperm or Chroma) are connected to the above-mentioned objectives for blocking the laser light and transferring the fluorescence emission from the fluorescent spatially immobilised microparticles of the encoded beads described elsewhere, An electronic pulse generator, e.g. of the type TGP110 supplied by Thurlby Thanders instruments, TTi, can preferably be used for generating a pulse for simultaneous triggering said two cameras and said two image intensifiers, whereby simultaneous pairs of images can be recorded with said two CCD cameras.

A framegrabber, e.g. of the type GrabLink Expert supplied by Eurecard, can be connected to the output terminals of said two CCD cameras for transferring the electronic signals from said two CCD cameras to a computer, e.g. a personal computer (such as e.g. a PC type Pentium 4 supplied by Unit-One electronics) connected to the output terminals of said framegrabber for electronically storing the images from said two CCD cameras. As an alternative to the use of CCD cameras any suitable digital camera can be used, e.g., C-MOS cameras. As an alternative to the use of image intensifiers connected to CCD cameras, on-chip multiplication gain cameras can also be used.

Analysis Section

Once the beads have passed through the measuring section (106), they are transferred by further step-wise rotation to an analysis section (607). In the analysis section (607) the images resulting from the imaging of captured beads in the imaging section are being analysed at the same time as the beads are being transferred in a step-wise fashion towards the one unloading section (606).

A variety of data processing methods can be carried out when analysing the data generated by the measuring of the at least one bead property by the measuring device in the measuring section. Examples of data processing methods and their results are described in detail herein below.

Analysing Bead Properties by Distance Matrix Determination

In one embodiment, the spatial immobilisation of the plurality of microparticles in each bead is essentially unique for each bead. The spatial positions of microparticles in each bead can be defined by sets of coordinates, (x,y,z) of microparticle centers of said microparticles, relative to one reference point of the detection. Furthermore, the relative positions in space of centers (x,y,z) of immobilised microparticles can be detected based on recording of 2D-projections of the microparticles.

In one embodiment, three 2D-projections are recorded along 3 orthogonal axis x, y and z to generate three sets of 2D-coordinates (y,z), (x,z) and (x,y), respectively, from which the 3D-coordinates (x,y,z) of microparticle centers can be derived. A stack of 2D projections can be generated by confocal or focal microscopy to recreate the 3D image matrix of the bead from which the relative microparticle position (x,y,z) in space can be determined.

One method for determination of relative microparticle positions within a bead can be based on using focussed scanning lasers for determining the coordinates x, y and z of a microparticle detachably fixed on a capture disc inlet by fast scanning two orthogonally aligned lasers over three cross sections of the bead.

Accordingly, it is possible to determine the coordinates x, y and z of a microparticle position by using a single laser and a rotating mirror that via 2 or three geometrically arranged static mirrors reflects the laser beam along 2 or 3 orthogonal axis.

A further method for determination of relative microparticle positions within a bead can be based on phase shifting digital holography, which determines the 3D structure of the interface between the microparticles and the surrounding polymer of the bead based on the reflections of light of said interface [Ichirou Yamaguchi, Jun-ichi Kato, Sohgo Ohta, and Jun Mizuno, 1 Dec. 2001, Vol. 40, No. 34, APPLIED OPTICS], [Etienne Cuche, Frédéric Bevilacqua, and Christian Depeursinge Mar. 1, 1999/Vol. 24, No. 5/OPTICS LETTERS 291].

Accordingly, one method for recording the unique pattern of each encoded bead comprises the steps of recording the relative coordinates of the center of the spatially immobilised microparticles and calculating a distance matrix based on the recorded coordinates. Accordingly, it is possible to convert the relative coordinates into absolute and unique parameters for each bead by generating for each bead a distance matrix of inter microparticle distances.

The coordinates of the microparticles in a bead can be generated in a variety of different ways.

1. A laser or conventional light excitation of the entire bead can be combined with detection along 3 orthogonal axis with three CCD cameras and the three sets of coordinates measured in 2D X,Y; Y,Z and X,Z for each microparticle can be used to correlate the microparticles to give a unique set of parameters XYZ for each immobilised microparticle.
2. A principle of focal or confocal microscopy can be used to obtain a 3D representation of the bead in which the 3 coordinates are the x and y of the microparticle in the a particular picture while the z-coordinate is derived from the focal depth.
3. Using fluorescence labelled microparticles a set of two focussed alternating scanning lasers along three orthogonal axis can excite the fluorophores on a microparticle of a spatially encoded bead located on the capture disc in the measuring section and the fluorescence can be recorded with a photo-sensor equipped with a fluorescence filter. The coordinates are generated from the three excitation coordinates.

The methods and spatially encoded beads described above can be used to identify single beads out of a very large assembly of beads by rapid decoding at any point of process time. They can furthermore be used in connection with diagnostic kits where a large mixture of beads are used in a fashion similar to that of spatial arrays of e.g. DNA or protease substrates.

When polymer beads encoded with spatially immobilised microparticles are to be identified by the distance matrix between said spatially immobilised microparticles, the relative position of each microparticle must be determined within some acceptable experimental error, such as a general spatial uncertainty of e.g. one microparticle diameter. As a further example two or more sets of 2D projections of microparticles can give rise to more than one set of three-dimensional microparticle positions.

To a large extent this can be done by multiple imaging or laser scanning. However, erroneous distance matrices may result in cases where the optical data obtained gives rise to two or more three-dimensional (3D) interpretations. For instance, when encoded beads are viewed from two orthogonal angles corresponding to an x,z-projection and a y,z-projection, a "correspondence problem" arises when two or more spatially immobilised microparticles have the same z-value within the optical accuracy of the equipment. One example of the "correspondence problem" arising from one set of images giving rise to two or more possible 3D-structures is illustrated in FIG. 9.

Below is provided three non-limiting examples of conceivable solutions to the "correspondence problem"

Solution 1: Focal Depth Evaluation

Spatially immobilised microparticles positioned at the focal plane of the imaging objective appear as sharp and intense bright spots, whereas microparticles positioned away from the focal plane of the objective appear as less sharp and less intense, the sharpness and intensity gradually decreasing as the distance from the microparticle to the focal plane increases.

In case that the dimensions of the imaging section exceeds the focal depth of the objectives, any 2D-projection will—apart from giving the 2D-positions of each microparticle—also provide information about the distance of each microparticle from the focal plane. This information can be used to distinguish between spatially immobilised microparticles which are otherwise indistinguishable or result in the calculation of more than one distance matrix.

Figure 10:
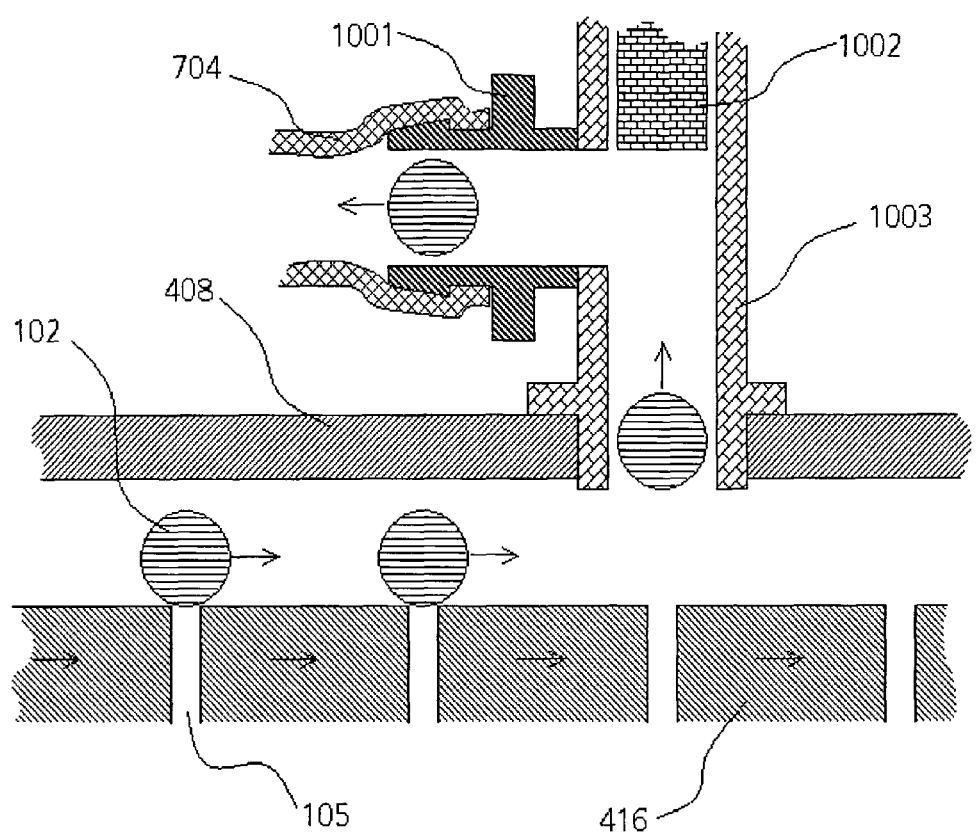
FIG. 10. shows a sorting section for selectively removing beads from the capture body by suction: 1001 connecting piece, 1002 piston, 1003 piston cylinder, 1004 tube.

One example of the correspondence problem is given in FIG. 10 in PCT/DK03/00635.

Solution 2: Principal Component Projection

This solution is provided essentially by performing the method steps listed herein below:

1. Obtaining an orthogonal pair of images of each spatially encoded bead,
2. Determining the 2D-positions of each spatially immobilised microparticle in each of said two orthogonal images,
3. Combining the resulting two orthogonal sets of 2D-positions whereby the set of possible sets of 3D-positions is obtained for each spatially encoded bead.
4. Calculating the principal component axis, x', y', z', of one of set of possible sets of 3D spatially immobilised microparticle positions.
5. Calculating the projected set of 3D spatially immobilised microparticle positions by projecting the 3D spatially immobilised microparticle positions onto said principal component axis.
6. Calculating the projected distance matrix based on the projected set of 3D spatially immobilised microparticle positions.
7. Identifying single spatially encoded beads by comparing the full set of projected distance matrices of single spatially encoded beads against the full set of projected distance matrices of all spatially encoded beads. The best fit of single projected distance matrices hereby obtained identifies single spatially encoded beads.

Encoded bead identification based on the principal component projected distance matrix is considerably more stable towards mismatching of spatially immobilised microparticles than encoded bead identification based on the conventional distance matrix.

Solution 3: Multiple Distance Matrix Calculation

A multiple distance matrix can be calculated by performing the steps of

1. Obtaining an orthogonal pair of images of each spatially encoded bead,
2. Determining the 2D-positions of each spatially immobilised microparticle in each of said two orthogonal images,
3. Combining the resulting two orthogonal sets of 2D-positions whereby the set of possible 3D-positions is obtained for each spatially encoded bead.
4. Computing the set of distance matrices corresponding to the set of 3D-positions thus determined.

8. Identifying single spatially encoded beads by comparing the full set of distance matrices of single spatially encoded beads against the full set of sets of distance matrices of all spatially encoded beads. The best fit of single distance matrices hereby obtained identifies single spatially encoded beads.

Theoretical Design Criteria for Spatially Encoded Beads

To demonstrate the versatility of the above methods, theoretical design criteria for spatially encoded beads with optimal features for identification can be obtained by 1. Forming a virtual set of spatially encoded beads in a computer on the basis of a set of spatially encoded bead properties, e.g., spatially encoded bead size distribution, spatially immobilised microparticle size distribution, and number of spatially immobilised microparticles per bead. Optical parameters should be included in the analysis, especially the uncertainty involved in the determination of the spatially immobilised microparticle positions,
2. Simulating random rotation of all spatially encoded beads,
3. Computing one pair of orthogonal projections of each of the spatially immobilised microparticles of each spatially encoded bead,
4. Combining the two orthogonal sets of 2D-positions whereby the set of possible 3D-positions is obtained for each spatially encoded bead,
5. Computing the set of distance matrices corresponding to the set of 3D-positions thus determined,
6. Identifying single spatially encoded beads by comparing the full set of distance matrices of single spatially encoded beads against the full set of distance matrices of all spatially encoded beads. The best fit of single distance matrices hereby obtained identifies single spatially encoded beads.
7. Registering the number of not-identified spatially encoded beads,
8. Varying one or more spatially encoded bead parameters and repeating the sequence 1 to 7 a one or more times.

Finding Theoretical Encoded Beads (EB) Design Criteria

A virtual set of N=5000 spatially encoded beads was formed in a computer with the use of a MatLab code. The following input parameters were used:

| Input parameter | Symbol | Value | Unit |
|---|---|---|---|
| EB diameter | D | 800 | micrometers |
| Spatially immobilised microparticle diameter | d | 10 | micrometers |
| Number of spatially immobilised microparticles per EB | M | 5 | — |
| Standard deviation of the error of the spatially immobilised microparticle positions | δ | 4 | micrometers |

This virtual set of spatially encoded beads was fed to a MatLab code for multiple distance matrix identification, which gave rise to the following output parameters:

| Output parameter | Symbol | Value | Unit |
|---|---|---|---|
| Number of spatially encoded beads with correspondence problem | C | 458 | |
| Number of ill-identified spatially encoded beads | E | 165 | |

The number of spatially immobilised microparticles per spatially encoded bead, M, and the standard deviation of the error of the spatially immobilised microparticle positions, δ, were varied stepwise and fed to the multiple distance matrix ID code.

Figure 11:
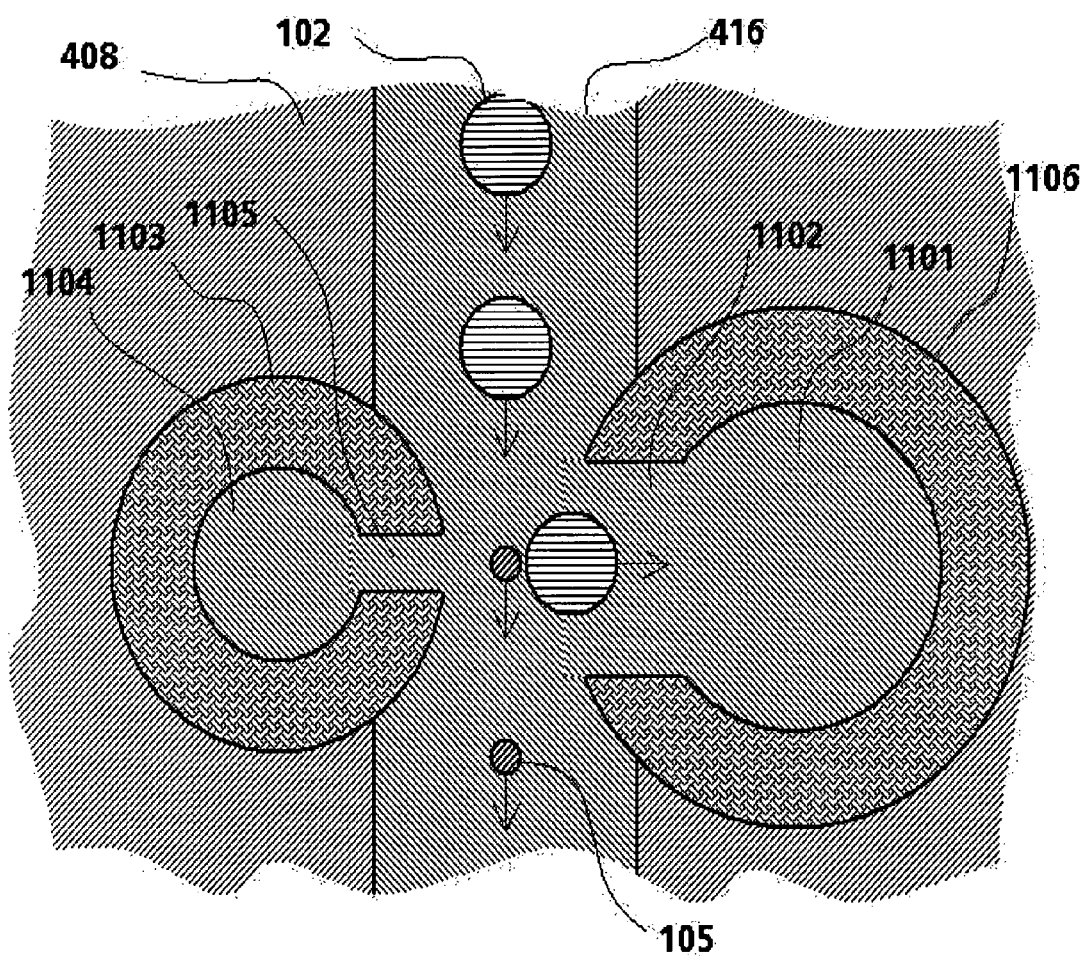
FIG. 11. shows a sorting section for selectively blowing beads from the capture body: 1101 vacuum volume, 1102 vacuum outlet, 1103 high pressure connecting piece, 1104 high pressure volume, 1105 high pressure outlet, 1106 vacuum connecting piece.

The result in terms of the number of spatially encoded beads with correspondence problem, C, and the number of ill-identified spatially encoded beads, E, is given in FIG. 11 of PCT/DK03/00635 where C and E are plotted against M and δ.

It can be seen from the upper plot of FIG. 11 of PCT/DK03/00635 that the number of correspondence problems increases with increasing number of spatially immobilised microparticles and with the error associated with the determination of the relative spatially immobilised microparticle positions as one would expect.

The lower plot in FIG. 11 FIG. 11 of PCT/DK03/00635 shows that in order to minimize the number of ill-identified spatially encoded bead, each spatially encoded bead should preferably comprise from 4 to 6 spatially immobilised microparticles. However, other numbers are also possible, such as from 3 to 8 spatially immobilised microparticles, for example 3 or 4 spatially immobilised microparticles, such as from 6 to 8 spatially immobilised microparticles for example 3, 4, 5, 6, 7, or 8 spatially immobilised microparticles.

At numbers of spatially immobilised microparticles below 4, the number of ill-identified spatially encoded beads increases abruptly, and at numbers higher than 4 spatially immobilised microparticles, the number of ill-identified spatially encoded beads increases gradually. The plot further shows that the number of ill-identified spatially encoded beads gradually increases with the positional error, and that the method breaks down when the positional error involved in the determination increases from 6 to 8 micrometers. These results can be used as design parameters for generating individually identifiable, spatially encoded beads.

For finding the 2D spatially immobilised microparticle-positions in images with the use of MatLab Imaging toolbox, it is possible to use e.g. a number of Gauss models, such as from 6 to 8 Gauss models, with same shape and varying size are applied to the image. For each Gauss model applied, one goodness-of-fit images are generated with the use of linear filtering. A new image is generated on the basis of the goodness-of-fit images as pixel-wise maximum of the goodness-of-fit images. The 2D spatially immobilised microparticle-positions can be found in this image as the positions of local maxima that have a goodness-of-fit value above a pre-set threshold value.

Sorting Section

Once the beads have passed through the measuring section (106) and an analysis section (408), they are optionally sorted into at least two fractions. In the embodiment disclosed in FIG. 4 one sorting section (602) is illustrated, but more sorting sections are required in other embodiments. The sorting section (602) serves to remove certain beads from the capture body while leaving other beads to proceed to the unloading section.

Figure 12:
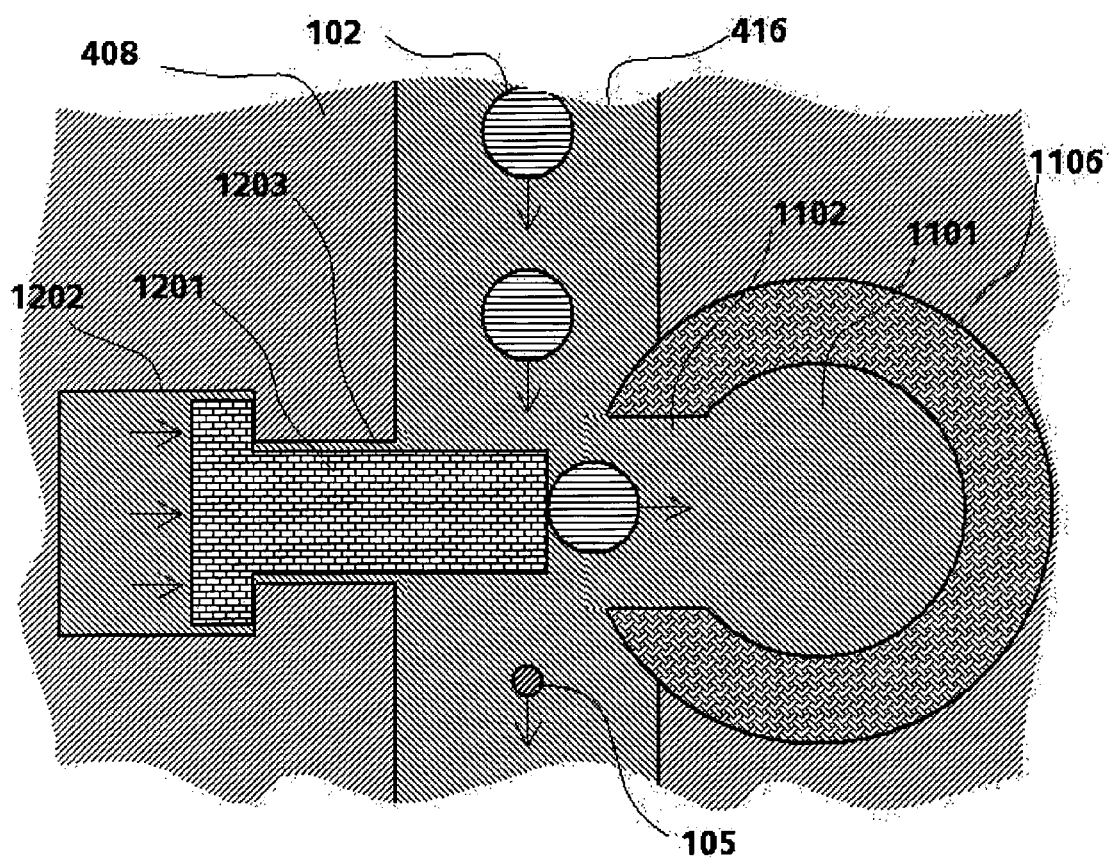
FIG. 12. shows a sorting section for selectively displacing beads from the capture body with a bead displacing body: 1201 bead displacing body, 1202 bead displacing body container, 1203 bead displacing body guiding channel.

Detailed disclosures of preferred embodiments of the sorting section are provided in FIGS. 10, 11, and 12, respectively.

FIG. 9 discloses the unloading section comprising an inlet in the guiding plate (408) fitted with a connecting piece (902) for forming a connection to a pump via a tubing (901). A stationary bead stopper (202), e.g. a PMMA bead stopper, is attached to one or more wall parts of the guiding channel, e.g. by a thin layer of glue, and blocks almost entirely the cross section of the guiding channel, thus ensuring that all beads (102) fixed to a capture hole (105) and entering the unloading section are unloaded from the capture disc (416). The stationary bead stopper at the same time keeps beads from passing from the loading section to the unloading section in the direction opposite the direction of the motion of the capture holes. This ensures that all beads passes the measuring section on the way from the loading section to the unloading section.

The sorting section is illustrated in a preferred embodiment in FIG. 10. The sorting section for unloading beads (102) from the capture disc (416) is located upstream of the unloading section (illustrated in a preferred embodiment in FIG. 9) and preferably comprises a through-going hole delimited by a cylinder (1003) in the guiding plate (408) with a piston valve (1002) positioned within the cylinder. The cylinder (1003) has an inner diameter of about 1 mm and is arranged perpendicular to the guiding channel so that the extended axis of the piston valve projects through the centre of the capture holes (105) of the capture disc (416) for the period of time during which the capture disc is stationary in-between the step-wise rotation of the capture disc. The piston valve (1002) positioned in the cylinder (1003) serves to connect and disconnect a vacuum in the guiding channel generated by a water pump. Preferably, a connecting piece (1001) connects the water pump to the piston valve via a tube (1004). A computer can be used to control the state of the valve (open vs. closed).

In a further embodiment of sorting section illustrated in FIG. 11 the sorting section preferably comprises a first cylindrical through-going hole in the guiding plate with a cylindrical high pressure connecting piece (1103) therein comprising a first end extending from the surface of the guiding plate (408) for connecting the high pressure connecting piece to the outlet of a valve via a high pressure tube, the inlet of said valve being connected to a pressurised water source, a second end positioned 0.1 mm from the surface of the capture body (416), an interior high pressure volume (1104), a high pressure outlet (1105) near the surface of the capture body and positioned such that the distance between the high pressure outlet and a passing capture hole be at its minimum in the time interval between the steps-wise motion of the capture holes, whereby it is obtained that when the valve is open a captured bead is blown away from its capture hole by the flow caused by the pressure drop over the high pressure outlet without neighbouring beads being affected, a second cylindrical through-going hole in the guiding plate with a cylindrical vacuum connecting piece (1106) therein comprising a first end extending from the surface of the guiding plate (408) for connecting the vacuum connecting piece to a vacuum via a vacuum tube, a second end positioned 0.1 mm from the surface of the capture body, an interior vacuum volume (1101) with a diameter allowing for a bead to unhindered pass through the vacuum connecting piece, a vacuum outlet (1102) near the surface of the capture body and positioned opposite the high pressure outlet of the high pressure connecting piece, said vacuum outlet connecting the vacuum volume to the guiding channel and having a cross section allowing for a bead to unhindered enter from the guiding channel to the vacuum volume, whereby it is obtained that a bead that has been blown away from its capture hole is drawn from the guiding channel and into the vacuum volume due to the flow caused by the pressure drop over the vacuum outlet, and removed from the apparatus via the vacuum tube.

It is essential that the pressure drop over the vacuum outlet be sufficiently high for being able to draw away beads that have been blown from their capture holes from the guiding channel, yet sufficiently low to not remove captured beads from their capture holes.

In yet a further embodiment of the second, optional unloading section illustrated in FIG. 12 the unloading section comprises a bead displacing body (1201) contained inside a bead displacing body container (1202) and restricted by a bead displacing body guiding channel (1201) connecting said bead displacing body container to the guiding channel, said bead displacing body container and said bead displacing body guiding channel extending from the surface of the capture body (416) and a distance less than the thickness of the guiding plate into the guiding plate, said bead displacing body guiding channel restricting the motion of said bead displacing body such that said bead displacing body can move only in directions essentially perpendicular to the motion of the beads, and said bead displacing body container restricting the motion of said bead displacement body such that said bead displacement body can only move a fixed distance in directions essentially perpendicular to the motion of the beads corresponding to a few bead diameters, and such that at one extreme of said restricted motion of said bead displacing body said bead displacing body extends across the track of the moving capture holes, and such that at the other extreme of said restricted motion of said bead displacing body said bead displacing body does not extend across the track of the moving capture holes and such that the shortest distance between the said bead displacing body to the track of the moving capture holes be larger than the bead radius, and means for manipulating said bead displacing body comprising a magnetic bead displacing body, and an electric coil positioned above said magnetic bead displacing body such that when a voltage is applied to said electric coil a magnetic field is generated that causes said magnetic bead displacing body to move to said one extreme of said restricted motion of said bead displacing body and such than when an opposite voltage is applied to said electric coil a magnetic field is generated that causes said magnetic bead displacing body to move to said other extreme of said restricted motion of said bead displacing body, whereby it is obtained that a bead can be displaced from its capture hole or not removed from its capture hole at the unloading section depending on the voltage applied to said electric coil, a second cylindrical through-going hole in the guiding plate with a cylindrical vacuum connecting piece (1106) therein comprising a first end extending from the surface of the guiding plate (408) for connecting the vacuum connecting piece to a vacuum via a vacuum tube, a second end positioned 0.1 mm from the surface of the capture body, an interior vacuum volume (1101) with a diameter allowing for a bead to unhindered pass through the vacuum connecting piece, a vacuum outlet (1102) near the surface of the capture body and positioned opposite the high pressure outlet of the high pressure connecting piece, said vacuum outlet connecting the vacuum volume to the guiding channel and having a cross section allowing for a bead to unhindered enter from the guiding channel to the vacuum volume, whereby it is obtained that a bead that has been blown away from its capture hole is drawn from the guiding channel and into the vacuum volume due to the flow caused by the pressure drop over the vacuum outlet, and removed from the apparatus via the vacuum tube.

whereby it is obtained that beads can be sorted into two fractions, by controlling the voltage applied to the electric coil.

When both the unloading section and the sorting section are present the different sections are connected to different pumps or the same pump for generating a vacuum in the unloading section and sorting section, respectively.

Accordingly, using the apparatus for bead sorting disclosed herein above it is possible to perform a method wherein a) beads are dispersed in dispersion liquid, thereby providing a dispersion comprising the beads to be measured and sorted,
b) the stepper motor is started, whereby the vacuum container comprising the capture disc is rotated in a step-wise manner in the direction indicated by the arrow in FIG. 5,
c) the vacuum container comprising the capture disc is submerged in dispersion liquid,
d) a first and a second vacuum is applied to the vacuum container and to the pipe for unloading beads by activating suitable pressure controlling devices including pumps,
e) dispersion comprising the dispersed beads is fed to the loading section of the apparatus, the beads being confined to a circular volume contacting the first surface of the capture disc by a stationary circular channel, such as a 1.1 mm deep and 1 mm wide stationary circular channel carved in a guiding plate and extending from the surface of the first surface of the disc and running along the perimeter of the circle defined by the capture holes: The capture holes are positioned in the middle part of the channel, whereby the beads are sucked onto the capture disc, essentially only one bead being captured at each capture hole.
f) individual beads are transferred along a circular path through the measuring section, where the beads are imaged, the images preferably being analysed and stored on a data storage medium such as e.g. a computer.
g) individual beads are further transferred to the unloading section where they are unloaded and removed from the capture disc through the pipe.

Encoded Beads Comprising Spatially Immobilised Microparticles

It is one object of the present invention to provide a polymer matrix for solid phase synthesis in the form of a bead comprising a plurality of spatially immobilised microparticles or vacuoles, wherein each microparticle or vacuole is individually detectable. The beads have different optical or spectroscopic properties from those of the immobilised microparticles or vacuoles. The immobilised microparticles or vacuoles can be mono-disperse or hetero-disperse, and the immobilised microparticles can be regular spherical beads or vacuoles, or they can be irregular microparticles. The bead can be spherical, i.e. having a regular, rounded shape, or it can have an irregular shape.

Each bead preferably comprises at least 2 microparticles, such as at least 3 microparticles, for example at least 4 microparticles, and preferably 10 or less microparticles, such as less than 5 microparticles. The microparticles can be essentially spherical, and preferably at least 2 such as 3, for example 5 of said microparticles have essentially the same diameter. The microparticles are preferably essentially mono-disperse and/or less than 10 micrometer in diameter, such as less than 5 micrometer in diameter, for example less than 1 micrometer in diameter, such as less than 0.1 micrometer in diameter.

The present invention resides in one embodiment in a bead on which a compound can be synthesised, wherein the bead has at least two markers integrally associated therewith, which markers are detectable and/or quantifiable during synthesis of the compound. The markers define a code identifying the bead before, during and after synthesis of a compound. Through the use of its plurality of detectable and/or quantifiable markers, preferably optically detectable and/or quantifiable markers, the bead of the present invention provides more "pre-encoded" information compared to other beads of the prior art and thus provides larger combinational library sizes that can be encoded.

This "pre-encoded" information may be read by specialized apparatus such as e.g. flow cytometers and the information can be used to track the synthetic history of an individual bead in a combinatorial process as described hereinafter. An example of a specialised apparatus for recording the "pre-encoded" information contained in an encoded bead is the specialised encoded bead reader apparatus disclosed herein below.

The larger the diversity of detectable and/or quantifiable markers of a bead, the greater the degree of decipherability or resolution of the bead in a large population of beads. In this regard, each detectable and/or quantifiable marker of a bead provides at least a part of the information required to distinctively identify the bead. The larger the number of such markers, the more detailed the identifying information that is compilable for a given bead, which may be used to distinguish that bead from other beads. On the other hand the complication of detection is increased markedly with the number of markers.

Markers

The microparticles can comprise a marker, which is detectable by any form of electromagnetic radiation including fluorescent emission. However, the marker can also be detected by fast spectroscopic techniques other than fluorescence spectroscopy. The microparticles of said beads in one embodiment comprise a spectroscopically detectable marker and/or a fluorescence detectable marker.

Fluorescence detectable markers are preferably selected from the fluorescent group of compounds and materials consisting of fluorescent organic poly-cyclic compounds, conjugated vinylic compounds, hetero-cyclic transition metal complexes, rare earth metal compounds, inorganic oxides and glasses.

Fluorescence detectable markers can be detected by two photon fluorescence spectroscopy and/or by one photon fluorescence spectroscopy. Fluorescence detectable markers can additionally be detected by time-correlated photon fluorescence spectroscopy.

Examples of detection by fast spectroscopic techniques other than fluorescence spectroscopy include, but is not limited to fast spectroscopic techniques such as infrared spectroscopy, raman spectroscopy, visible light spectroscopy, UV spectroscopy, electron spin resonance, and nuclear magnetic resonance.

The fluorescence detectable marker is preferably selected from the group consisting of dyes based on the structure of fluorescein, Oregon green, rhodamine, aminobenzoic acid, Alexa™ probes, BODIPY-dyes, cascade blue dye, coumarine, naphthalenes, dansyl, indoles, pyrenes pyridyloxazole, cascade yellow dye, Dapoxyl Dye, Fluorescamine, aromatic ortho di-aldehydes, OPA and NDA, ATTO-Tag's, 7-Nitrobenz-2-Oxa-1,3-Diazole or derivatives thereof. The fluorescence detectable marker in one embodiment is preferably a UV or visible light-excitable microsphere.

Fluorescent dyes may be incorporated into beads and microparticles by any suitable method known in the art, such as copolymerisation of a polymerisable monomer and a dye-containing co-monomer or addition of a suitable dye derivative in a suitable organic solvent to an aqueous suspension as for example disclosed in Singer et al., (supra including references cited therein), Campian et al. (1994, In "Innovation and Perspectives on Solid Phase Synthesis" Epton, R., Birmingham: Mayflower, 469-472, incorporated herein by reference) and Egner et al. (1997, Chem. Commun. 73 5-73 6, incorporated herein by reference). Alternatively, fluorescent beads may be produced having at least one fluorescent spherical zone. Such microparticles may be prepared as for example described in U.S. Pat. No. 5,786,219 (Zhang et al.), which is incorporated herein by reference. In a preferred embodiment, one or more fluorescent dyes are incorporated within a microparticle.

Also included in the present invention are markers which are detectable by fast detection techniques other than spectroscopy, such as light scattering, reflection, diffraction or light rotation.

Electromagnetic radiation-related markers are preferably selected from the group consisting of fluorescence emission, luminescence, phosphorescence, infrared radiation, electromagnetic scattering including light and X-ray scattering, light transmittance, light absorbance and electrical impedance.

Preferably, the electromagnetic radiation-related marker is a light emitting, light transmitting or light absorbing marker detectable by illuminating the microparticle with incident light of one or more selected wavelengths or of one or more selected vectors.

It is preferred that at least one of the markers of a bead is an electromagnetic radiation-related marker suitably selected from the group consisting of atomic or molecular fluorescence emission, luminescence, phosphorescence, infrared radiation, electromagnetic scattering including light and X-ray scattering, light transmittance, light absorbance and electrical impedance.

The fluorescence emission can result from e.g. excitation of one or more fluorescent markers attached to, or contained within, the bead. In the case of two or more fluorescent markers being utilised, the markers can be the same and the markers can comprise the same or varying amounts of a fluorophore. In the latter case the markers are intensity-differentiated.

Alternatively, the markers may be different wherein they are present in a ratio of 1:1 or varying ratios. Reference may be made in this regard to WO 95/32425 which is incorporated herein by reference.

Exemplary fluorophores which may be used in accordance with the present invention include those listed in WO 93/06121, which is incorporated by reference herein.

Any suitable fluorescent dye may be used for incorporation into the bead of the invention. For example, reference may be made to U.S. Pat. Nos. 5,573,909 (Singer et al., which is incorporated herein by reference) and 5,326,692 (Brinkley et al., which is incorporated herein by reference) which describe a plethora of fluorescent dyes. Reference may also be made to fluorescent dyes described in U.S. Pat. Nos. 5,227,487, 5,274, 113, 5,405,975, 5,433,896, 5,442,045, 5,451,663, 5,453,517, 5,459,276, 5,516,864, 5,648,270 and 5,723,218, which are all incorporated herein by reference.

In one embodiment, one or more of the fluorescent markers can preferably be incorporated into a microparticle, such as a polymeric microparticle, or a ceramic microparticle. Such microparticles can preferably be attached to a bead by use of e.g. colloidal interactions as for example disclosed by Trau and Bryant in PCT/AU98/00944, incorporated herein by reference.

When the marker is spectroscopically detectable, there is in one embodiment provided a marker capable of being probed by a range of frequencies differing by less than about 20%, such as less than about 10%, based on the numerical highest frequency value. The marker can also be probed by one or more predetermined frequencies.

Any suitable method of analysing fluorescence emission is encompassed by the present invention. In this regard, the invention contemplates techniques including, but not restricted to, 2-photon and 3-photon time resolved fluorescence spectroscopy as for example disclosed by Lakowicz et al. (1997, Biophys. J., 72: 567, incorporated herein by reference), fluorescence lifetime imaging as for example disclosed by Eriksson et al. (1993, Biophys. J., 2: 64, incorporated herein by reference), and fluorescence resonance energy transfer as for example disclosed by Youvan et al. (1997, Biotechnology et alia 3: 1-18).

Luminescence and phosphorescence may result respectively from a suitable luminescent or phosphorescent label as is known in the art. Any optical means of identifying such label may be used in this regard.

Infrared radiation may result from a suitable infrared dye. Exemplary infrared dyes that may be employed in the invention include, but are not restricted to, those disclosed in Lewis et al. (1999, Dyes Pigm. 42 (2): 197), Tawa et al. (1998, Mater. Res. Soc. Symp. Proc. 488 (Electrical, Optical, and Magnetic Properties of Organic Solid-State Materials IV), 885-890), Daneshvar, et al. (1999, J. Immunol. Methods 226 (1-2): 119-128), Rapaport et al. (1999, Appl. Phys. Lett. 74 (3): 329-331) and Durig et al. (1993, J. Raman Spectrosc. 24 (5): 281-5), which are incorporated herein by reference. Any suitable infrared spectroscopic method may be employed to interrogate the infrared dye. For instance, fourier transform infrared spectroscopy as for example described by Rahman et al. (1998, J. Org. Chem., 63: 6196, incorporated herein by reference) may be used in this regard.

Suitably, electromagnetic scattering may result from diffraction, reflection, polarisation or refraction of the incident electromagnetic radiation including light and X-rays. In this regard, the beads may be formed of different materials to provide a set of beads with varying scattering properties such as different refractive indexes as for example described supra. Any suitable art recognised method of detecting and/or quantifying electromagnetic scatter may be employed. In this regard, the invention also contemplates methods employing contrast variation in light scattering as, for example, described in van Helden and Vrij (1980, Journal of Colloidal and Interface Science 76: 419-433), which is incorporated herein by reference.

Markers other than electromagnetic radiation-related markers can be utilised, optionally in combination with electromagnetic radiation-related markers. Such markers include e.g. size and/or shape of the bead. For example, beads may be shaped in the form of spheres, cubes, rectangular prisms, pyramids, cones, ovoids, sheets or cylinders, including intermediate forms as well as irregular shapes. Electrical impedance across a bead may be measured to provide an estimate of the bead volume (Coulter).

The marker in one embodiment comprises a chromophoric label. Suitable beads comprising such chromophores are described e.g. by Tentorio et al. (1980, Journal of Colloidal and Interface Science 77: 419-426), which is incorporated herein by reference.

A suitable method for non-destructive analysis of organic pigments and dyes, using a Raman microprobe, micro-fluorometer or absorption micro-spectrophotometer, is described for example in Guineau, B. (1989, Cent. Rech. Conserv. Documents Graph., CNRS, Paris, Fr. Stud. Conserv 34 (1): 38-44), which is incorporated herein by reference.

Alternatively, the marker may comprise a magnetic material inclusive of iron and magnetite, or an marker that is detectable by acoustic backscatter as is known in the art.

It will be understood from the foregoing that the number of beads having different detectable codes will be dependent on the number of different detectable and/or quantifiable markers integrally associated with the beads.

Beads Comprising Polymers and Other Materials

Beads can comprise any solid material as long as it has sufficient mechanical strength to withstand the mechanical stress invoked on a bead captured at a capture hole. Also the beads must be sufficiently hard to withstand being sucked through the capture hole. On the other hand preferred materials are sufficiently flexible for the bead to conform sufficiently to the capture hole to seal the capture hole when captured and thereby ensuring a maximum difference in pressure between the part of the bead facing the capture hole and the part of the bead facing away from the capture hole, said pressure difference giving rise to a force acting on the bead in a direction opposite to the normal force acting on the bead imposed by the capture body, said opposing forces immobilising the bead at the capture hole. A wide range of materials conform to the above criteria and include cross-linked synthetic polymers, biological specimens, such as fish spawn, reptile and amphibian eggs, and aquatic animals of proper size and shape. Preferred materials for beads comprise materials capable of providing a basis for combinatorial chemistry, especially polymers capable of providing a basis for combinatorial chemistry. Also inorganic materials capable of providing a solid phase basis for combinatorial chemistry can be used.

Beads Comprising Polymers

Polymers for encoded beads according to the present invention are preferably optically transparent in the optical excitation range of the fluorescent marker and/or the emission wavelength range of the fluorescent marker comprised by the microparticles and/or vacuoles of the polymer matrix.

Encoded polymer beads according to the invention can be prepared from a variety of polymerisable monomers, including styrenes, acrylates and unsaturated chlorides, esters, acetates, amides and alcohols, including, but not limited to, polystyrene (including high density polystyrene latexes such as brominated polystyrene), polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidenechloride and polydivinylbenzene, as well as PEGA, SPOCC and POEPOP. The beads may be prepared from styrene monomers or PEG based macro-monomers.

The polymer is in preferred embodiments selected from the group consisting of polyethers, polyvinyls, polyacrylates, polymethacrylates, polyacylamides, polyurethanes, polyacrylamides, polystyrenes, polycarbonates, polyesters, polyamides, and combinations thereof.

In more preferred embodiments, the polymer is selected from the group consisting of SPOCC, PEGA, HYDRA, POEPOP, PEG-polyacrylate copolymers, polyetherpolyamine copolymers, cross-linked polyethylene di-amines, and combinations thereof.

Encoded Beads Other than Polymer Beads

However, the invention is not limited to the above polymers as beads other than polymer beads can in principle comprise any at least partly transparent solid material capable of providing a base for combinatorial chemistry. As illustrative examples, the beads can be polymeric supports such as polymeric beads, which are preferably formed from polystyrene cross-linked with 1-5% divinylbenzene. Polymeric beads can also be formed from hexa-methylenediaminepolyacryl resins and related polymers, poly N-{2-(4-hydroxylphenyl) ethyl}acrylamide (i.e., (one Q)), silica, cellulose beads, polystyrene beads poly (halomethylstyrene) beads, poly (halostyrene) beads, poly (acetoxystyrene) beads, latex beads, grafted copolymer beads such as polyethylene glycol/polystyrene, porous silicates for example controlled pore-glass beads, polyacrylamide beads for example poly (acryloylsarcosine methyl ester) beads, dimethylacrylamide beads optionally cross-linked with N,N'-bis-acrylolyl ethylene di-amine, glass beads coated with a hydrophobic polymer inclusive of cross-linked polystyrene or a fluorinated ethylene polymer which provides a material having a rigid or semi-rigid surface, poly (N-acryloylpyrrolidine) resins, Wang resins, Pam resins, Merrifield resins, PAP and SPARE polyamide resins, polyethylene functionalised with acrylic acid, kieselguhr/polyamide (Pepsyn K), polyHipe™, PS/polydimethylacrylamide copolymers, CPG, PS beads and Tentagel™, PEG-PS/DVB copolymers.

Ceramic beads may be comprised of silica, alumina, titania or any other suitable transparent material. A suitable method of making silica beads is described, for example in "The Colloid Chemistry of Silica and Silicates" (Cornell University Press) by Ralph K Iler 1955 and U.S. Pat. No. 5,439,624, the disclosures of which are incorporated herein by reference. Reference may also be made to WO95/25737 and WO97/15390, incorporated herein by reference, which disclose examples of such beads.

Dimensions of Encoded Beads

The beads according to the invention preferably has a ratio $R=a/b$ between a) the volume of the bead and b) the average volume of the microparticles which is in the range of from 10000000:1 to 10:1, such as in the range of from 1000000:1 to 30:1, for example in the range of from 1000000:1 to 100:1, for example in the range of from 1000000:1 to 200:1, such as in the range of from 1000000:1 to 1000:1, for example in the range of from 100000:1 to 1000:1, such as in the range of from 100000:1 to 2000:1.

Independently of the above ratios, the beads according to the invention preferably comprises an average volume of the swelled bead of from 0.000001 µL-50 µL, such as an average volume of the swelled bead of from 0.00001 µL-5 µL, for example an average volume of the swelled bead of from 0.001 µL-1 µL, such as an average volume of the swelled bead of from 0.01 µL-0.1 µL.

Any combination of the above falls within the invention and accordingly, for a ratio $R=a/b$ between a) the volume of the bead and b) the average volume of the microparticles which is in the range of from 10000000:1 to 10:1, such as in the range of from 1000000:1 to 30:1, for example in the range of from 1000000:1 to 100:1, for example in the range of from 1000000:1 to 200:1, such as in the range of from 1000000:1 to 1000:1, for example in the range of from 10000:1 to 1000:1, such as in the range of from 100000:1 to 2000:1, the average volume of the swelled bead can be from 0.000001 µL-50 µL, such as an average volume of the swelled bead of from 0.00001 µL-5 µL, for example an average volume of the swelled bead of from 0.001 µL-1 µL, such as an average volume of the swelled bead of from 0.01 µL-0.1 µL.

Composition Comprising a Plurality of Encoded Beads

The invention is in one embodiment directed to a plurality of beads comprising a population that is pre-encoded. Accordingly, each bead of that population has a code, which distinctively identifies a respective bead before, during and after said synthesis from other beads. The diversity of the said population of beads, therefore, resides in beads of said population having relative to each other different spatial locations of detectable markers, which are used to provide distinctive codes for detection of each of those beads.

The composition of beads of the invention may be used in many applications, such as affinity chromatography for purification and/or isolation of desirable target compounds, and combinatorial chemistry procedures that do or do not involve a split-and-combine procedure. Preferably, however, such assemblies are used in combinatorial chemistries, which involve a split-process-recombine procedure.

Preparation of Beads

A plurality of beads according to the invention may be prepared by any suitable method. Preferably, when colloidal beads including polymeric and ceramic beads are used as beads, the colloid dispersion of such beads is stabilised. Exemplary methods imparting colloidal stabilisation are described for example in Hunter, R. J. (1986, "Foundation of Colloid Science", Oxford University Press, Melbourne) and Napper, D. H. (1983, "Polymeric stabilisation of Colloidal Dispersions" Academic Press, London), the disclosures of which are incorporated herein by reference. In this regard, the most widely exploited effect of nonionic polymers on colloid stability is steric stabilisation, in which stability is imparted by polymer molecules that are absorbed onto, or attached to, the surface of the colloid beads. Persons of skill in the art will recognise that it is possible to impart stability by combinations of different stabilisation mechanisms: e.g., surface charge on the beads can impact colloidal stability via electrostatic stabilisation, and an attached polyelectrolyte can impart stability by a combination of electrostatic and steric mechanisms (electrosteric stabilisation). Polymer that is in free solution can also influence colloid stability. Stabilisation by free polymer is well-documented (Napper 1983, supra) and is called depletion stabilisation.

Preferably, steric stabilisation of colloid dispersions is employed. In this regard, steric stabilisation is widely exploited because it offers several distinct advantages over electrostatic stabilisation. For example, one advantage is that aqueous sterically stabilised dispersions are comparatively insensitive to the presence of electrolytes because the dimensions of non-ionic chains vary relatively little with the electrolyte concentration.

Any suitable stabilising moiety may be used for stabilising colloidal dispersions. Exemplary stabilising moieties that impact on colloidal stability are given herein below: Poly (oxyethylene), Poly (vinyl alcohol), Poly (acrylic acid), Poly (acrylamide), and sorbitol monolaurate as well as commonly used emulsion stabilizers.

The composition of encoded, beads preferably comprises at least $10^2$ individually identifiable beads, such as at least $10^3$ individually identifiable beads, for example at least $10^5$ individually identifiable beads, such as at least $10^7$ individually identifiable beads, for example at least $10^9$ individually identifiable beads, such as at least $10^{11}$ individually identifiable beads, for example at least $10^{13}$ individually identifiable beads, such as at least $10^{15}$ individually identifiable beads, for example at least $10^{17}$ individually identifiable beads, such as at least $10^{19}$ individually identifiable beads, for example at least $10^{21}$ individually identifiable beads, such as at least $10^{23}$ individually identifiable beads.

Preparation of Encoded Beads

It is a further object of the invention to provide a method for generating a composition comprising a plurality of encoded beads, said method comprising the steps of i) synthesizing a monomer and/or macro-monomer and a crosslinker for polymerisation, and, ii) mixing the monomer and/or macro-monomer with microparticles to give an even dispersion of microparticles in the mixture, and iii) polymerising the monomer and/or macro-monomer by either i) suspension polymerisation and/or; ii) inverse suspension polymerisation and/or iii) bulk polymerisation followed by granulation and/or iv) droplet polymerisation.

In particular, spatially encoded PEGA-type polymer beads can be prepared by inverse phase co-polymerisation at 70° C. of acrylamide-end-capped polyethyleneglycol and acrylamide in a 1:1 ratio in 2% (w/w) aqueous sorbitan monolaurate in the presence of 0.6% (w/w) di-methylformamide swelled Oregon green (supplied by Molecular probes) dyed microspheres (TentaGel M30202 supplied by RAPP Polymere). After polymerisation the beads are washed with demineralised water and sieved. The resulting 0.5-0.7 mm diameter fraction is isolated and e.g. analysed in the apparatus described in Example 1 herein. Preferably, more than 60% of the encoded beads, such as about 80% or more than 80% of the encoded beads comprise from 4 to 10 microparticles, such as from 4-6 microparticles.

In a further aspect there is provided a method for generating a composition comprising a plurality of encoded beads and detecting and/or identifying individually identifiable beads, said method comprising the steps of:

(a) preparing a plurality of beads comprising spatially immobilised microparticles comprising at least one marker;

(b) detecting and/or quantifying the said markers of each bead and assigning a code, such as the result of a determination of the location of spatially encoded microparticles or vacuoles, for each bead;

(c) identifying beads having distinctive codes; and optionally (d) identifying beads having similar codes; and further optionally (e) sorting the beads having distinctive codes from the beads having non-distinctive codes to thereby provide a plurality of encoded beads.

There is also provided the use of such a composition comprising a plurality of encoded beads linked to a bioactive compound for identifying bioactive compound binding partners, and a use of the composition of beads linked to different bioactive compounds for diagnostic purposes, wherein the binding and determination of a predetermined binding partner to a substrate or bioactive compound on the carrier is at least indicative of a positive diagnosis.

Bioactive compounds of particular interest are e.g. those which may be so screened include agonists and antagonists for cell membrane receptors, toxins, venoms, viral epitopes, hormones, sugars, co-factors, peptides, enzyme substrates, drugs inclusive of opiates and steroids, proteins including antibodies, monoclonal antibodies, antisera reactive with specific antigenic determinants, nucleic acids, lectins, polysaccharides, cellular membranes and organelles.

The present invention also encompasses as bioactive compounds a plurality of unique polynucleotide or oligonucleotide sequences for sequence by hybridisation (SBH) or gene expression analyses. Persons of skill in the art will recognise that SBH uses a set of short oligonucleotide probes of defined sequence to search for complementary sequences on a longer target strand of DNA. The hybridisation pattern is used to reconstruct the target DNA sequence. Accordingly, in the context of the present invention, an aqueous solution of fluorescence labelled single stranded DNA (ssDNA) of unknown sequence may be passed over the library of polynucleotide or oligonucleotide compounds and adsorption (hybridisation) of the ssDNA will occur only on beads which contain polynucleotide or oligonucleotide sequences complementary to those on the ssDNA. These beads may be identified using an apparatus and the methods of the present invention.

Once a compound having the desired activity is obtained, the sequence of reaction steps experienced by the bead on which the compound was synthesised may be deconvoluted simply by analysing the tracking data for that bead as described, for example, hereinafter. The sequence of building blocks defining the compound of interest may thus be ascertained and a molecule comprising this sequence can by synthesised by conventional means (e.g., amino acid synthesis or oligonucleotide synthesis) as is known in the art.

Encoded beads can be sorted according to at least one optical parameter, i.e., a physical property that influences the optical signal arising from the encoded bead, such as size and shape and number of microparticles per encoded bead, whereby it is obtained that the resulting encoded beads are individually identifiable by optical means. Preferred means for sorting encoded beads include sedimentation, centrifugation, sieving, cyclone separation, total fluorescence separation, and separation according to number of microparticles per encoded bead. Accordingly, separation based on total fluorescence and/or separation based on the number of microparticles per encoded bead can be carried out simultaneously and/or sequentially using an apparatus of the present invention further comprising an analysing device and a sorting device.

The polymerisation reaction can preferably be a radical initiated chain polymerisation reaction, or an anion initiated ring opening polymerisation reaction, or a cation initiated ring opening polymerisation reaction.

Functional groups on the beads can subsequently be reacted with different bioactive compound building blocks as described herein elsewhere. Each reaction step can be monitored as essentially each bead of the encoded bead is individually detectable. The below methods describe in more detail the preparation of microparticles.

Sorting Microparticles According to Size and Controlling the Size Distribution of Microparticles.

Microparticles may be sorted according to at least one optical parameter, i.e., a physical property that influences the optical signal arising from the microparticle, such as size, shape, colour, or fluorescence, whereby it is obtained that the relative positions of said microparticles can be determined by optical means. Preferred means for sorting microparticles include sedimentation, centrifugation, sieving, and cyclone separation.

Using spatially immobilised microparticles as microparticles in encoded beads places some limitations on the size of the spatially immobilised microparticles. Too large spatially immobilised microparticles tens to shadow each other and too small spatially immobilised microparticles may pass through the optical set-up unnoticed.

Generally the size distribution of spatially immobilised microparticles synthesized by suspension polymerisation or emulsion polymerisation is very broad. Hence, a method for obtaining a fraction of spatially immobilised microparticles with controlled size distribution is required.

It has been found that the micro beads in di-methylformamide (DMF) solution after centrifugation at 250 rpm for 22 min are considerably smaller than the micro beads in the sediment. This indicates that it is possible to remove small beads by repeated centrifugation at 250 rpm and removing the liquid phase after each run, i.e. the concentration of small beads in the sediment should decrease after each run.

Post Identification of Spatially Encoded Beads

The sequence comprising 1) determination of the spatially immobilised microparticle positions in the images, 2) calculation of the corresponding set of possible 3D-positions of the spatially immobilised microparticles and the corresponding distance matrices, and 3) the distance matrix based identification, may be too time consuming to allow for on-line identification of encoded beads. As an alternative post identification of "hits", i.e., spatially encoded beads carrying compounds which have shown to be of interest in a given assay can be carried out As the hits are not identified until after the full combinatorial chemistry synthesis, the hit identification will have to be carried out after the combinatorial synthesis process has been finished. Following a procedure comprising the following steps can do this:

1. A plurality of spatially encoded polymer beads is synthesized
2. Images or laser scans of each encoded bead is recorded and stored as the beads are being split into a number of jars, $J_1$, $J_2$ ... $J_i$ in which jars one combinatorial synthesis step is carried out.
3. All beads are pooled
4. The sequence comprising steps 2 and 3 is repeated a number of times.
5. All spatially encoded beads are screened in a given assay and the hits are separated
6. The jar sequence of each hit is determined on the basis of the recordings obtained under step 2 and the use of an ID method.

Method for Generating an Encoded Bead Comprising Different Bioactive Compounds

It is a yet further object of the invention to provide a method for generating an encoded, bead comprising a bioactive compound, wherein essentially each bead of the polymer matrix is individually identifiable, said method comprising the steps of
i) spatially immobilizing microparticles in polymer beads,
ii) isolating encoded beads by automated sorting,
iii) recording and storing the distance matrix for essentially each bead,
iv) performing a stepwise synthesis of bioactive compounds by reacting functional groups of the encoded beads with at least one building block,
v) recording the identity of each bead that enter each reaction step iv),
vi) isolating beads of interest, preferably by performing an assay or a diagnostic screen,
vii) identifying the bioactive compound attached to at least one individual bead by recording the identity of at least one isolated bead, and optionally comparing said recording with the recording, preferably a distance matrix, recorded for at least a plurality of the remaining beads.

A binding assay for characterising or isolating bioactive compounds bound to the beads can be performed by measuring e.g. the binding of a protein to a ligand bound to the polymer matrix. Also, an assay can be performed by measuring e.g. an enzyme activity on a substrate bound to the polymer matrix. It is also possible to perform an assay by measuring e.g. enzyme inhibition of a molecule bound to the polymer matrix, or to perform an assay by measuring e.g. receptor interaction with a bioactive compound bound to the polymer matrix.

For the above methods, the plurality of microparticles preferably comprise a fluorescence detectable marker, such as a fluorescence detectable marker detectable by two photon fluorescence microscopy, or a fluorescence detectable marker detectable by one photon fluorescence microscopy.

Method for Deconvoluting a Conventional Library

In a further aspect, the invention provides a method for synthesising and deconvoluting a combinatorial library comprising the steps of:
(a) apportioning in a stochastic manner among a plurality of reaction vessels a plurality of beads on which a plurality of different compounds can be synthesised, wherein said plurality of beads comprises a population of detectably distinct beads each having a code, such as spatially immobilised microparticles or vacuoles, which distinctively identifies a respective bead before, during and after said synthesis from other beads,
(b) determining and recording the codes, preferably in the form of the spatial position of the immobilised microparticles or vacuoles, of said plurality of beads in order to track the movement of individual detectably distinct beads into particular reaction vessels of said plurality of reaction vessels, wherein said codes are determined prior to step (d);
(c) reacting the beads in each reaction vessel with a building block;
(d) pooling the beads from each reaction vessel;
(e) apportioning the beads in a stochastic manner among the plurality of reaction vessels;
(f) reacting the beads in each reaction vessel with another building block;
(g) recording the codes of said plurality of beads in order to track the movement of individual detectably distinct beads into particular reaction vessels of said plurality of reaction vessels, wherein said codes are recorded after step (e) and/or step (f;
(h) pooling the beads from each reaction vessel;
(i) iterating steps (e) through (h) as required in order to create a combinatorial compound library wherein member compounds of the library are associated with the detectably distinct beads and wherein codes of the detectably distinct beads are deconvolutable using tracking data provided by said recordal steps to identify the sequence of reactions experienced by the said detectably distinct beads.

The identification steps (step (c) and (d)) may be effected by use of any suitable method or apparatus for analysing the spatially immobilised markers of a bead.

Preferably, these steps are effected by flow cytometry, which typically detects optical parameters. For example, a flow cytometer may be used to determine forward scatter (which is a measure of size of a bead), side scatter (which is sensitive to refractive index and size of a microparticle (seen Shapiro 1995, "Practicalflow cytometry", 3d ed. Brisbane, Wiley-Liss)), and fluorescent emission.

Any suitable algorithm may be employed to track and/or sort individual detectably unique beads. Preferably, a real-time algorithm is employed.

Suitably, the step of sorting (step (e)) is characterised in that the population of detectably distinct beads constitutes at least about 50%, preferably at least about 70%, more preferably at least about 90%, and more preferably at least about 95% of the plurality of beads resulting from step (e).

From the foregoing, a population of detectably unique beads can be generated from a raw population of beads using e.g. specialised flow cytometric techniques. The population of detectably unique beads is thereby "pre-encoded" and can be used for combinatorial synthesis.

Building Block Reactions

The beads of the invention are applicable to any type of chemical reaction that can be carried out on a solid support. Such chemical reaction includes, for example:
1. 2+2 cycloadditions including trapping of butadiene;
2. [2+3] cycloadditions including synthesis of isoxazolines, furans and modified peptides;
3. acetal formation including immobilization of diols, aldehydes and ketones;
4. aldol condensation including derivatization of aldehydes, synthesis of propanediols;
5. benzoin condensation including derivatization of aldehydes;
6. cyclocondensations including benzodiazepines and hydantoins, thiazolidines, -turn mimetics, porphyrins, phthalocyanines;
7. Dieckmann cyclization including cyclization of diesters;
8. Diels-Alder reaction including derivitisation of acrylic acid
9. Electrophilic addition including addition of alcohols to alkenes;
10. Grignard reaction including derivatisation of aldehydes;
11. Heck reaction including synthesis of disubstituted alkenes;
12. Henry reaction including synthesis of nitrile oxides in situ (see 2+3 cycloaddition);
13. catalytic hydrogenation including synthesis of pheromones and peptides (hydrogenation of alkenes);
14. Michael reaction including synthesis of sulfanyl ketones, bicyclo] 2.2.2] octanes;
15. Mitsunobu reaction including synthesis of aryl ethers, peptidyl phosphonates and thioethers;
16. nucleophilic aromatic substitutions including synthesis of quinolones;
17. oxidation including synthesis of aldehydes and ketones;
18. Pausen-Khand cycloaddition including cyclization of norbornadiene with pentynol;
19. photochemical cyclisation including synthesis of helicenes;
20. reactions with organo-metallic compounds including derivitisation of aldehydes and acyl chlorides;
21. reduction with complex hydrides and Sn compounds including reduction of carbonyl, carboxylic acids, esters and nitro groups;
22. Soai reaction including reduction of carboxyl groups;
23. Stille reactions including synthesis of biphenyl derivatives;
24. Stork reaction including synthesis of substituted cyclohexanones;
25. reductive amination including synthesis of quinolones;
26. Suzuki reaction including synthesis of phenylacetic acid derivatives; and
27. Wittig, Wittig-Horner reaction including reactions of aldehydes; pheromones and sulfanyl ketones.

Reference may also be made to Patel et al., (April 1996, DDT 1 (4): 134-144) who describe the manufacture or synthesis of N-substituted glycines, polycarbamates, mercaptoacylprolines, diketopiperazines, HIV protease inhibitors, 1-3 diols, hydroxystilbenes, B-lactams, 1,4-benzodiazepine-2-5-diones, dihydropyridines and dihydropyrimidines.

Reference may also be made to synthesis of polyketides as discussed, for example, in Rohr (1995, Angew. Int. Ed. Engl. 34: 881-884).

Chemical or enzymatic synthesis of the compound libraries of the present invention takes place on beads. Thus, those of skill in the art will appreciate that the materials used to construct the beads are limited primarily by their capacity for derivitisation to attach any of a number of chemically reactive groups and compatibility with the chemistry of compound synthesis. Except as otherwise noted, the chemically reactive groups with which such beads may be derivatised are those commonly used for solid state synthesis of the respective compound and thus will be well known to those skilled in the art. For example, these bead materials may be derivatised to contain functionalities or linkers including —NH2, —NHNH2, —ONH2, —COOH, —SH, SeH, —SO3H, —GeH, or —SiR2H groups.

Linkers for use with the beads may be selected from base stable anchor groups as described in Table 2 of Fruchtel et al. (1996, supra, the entire disclosure of which is incorporated herein by reference) or acid stable anchor groups as described in Table 3 of Fruchtel et al. (1996, supra). Suitable linkers are also described in WO93/06121, which is incorporated herein by reference.

In the area of peptide synthesis, anchors developed for peptide chemistry are stable to either bases or weak acids, but for the most part, they are suitable only for the immobilisation of carboxylic acids. However, for the reversible attachment of special functional groups, known anchors have to be derivatised and optimised or, when necessary, completely new anchors must be developed. For example, an anchor group for immobilisation of alcohols is (6 hydroxymethyl)-3,4 dihydro-2H-pyran, whereby the sodium salt is covalently bonded to chloromethylated Merrifieldz resin by a nucleophilic substitution reaction. The alcohol is coupled to the support by electrophilic addition in the presence of pyridinium toluene-4 sulphonate (PPTS) in dichloromethane. The resulting tetrahydropyranyl ether is stable to base but can be cleaved by transetherification with 95% trifluoroacetic acid. Benzyl halides may be coupled to a photolabile sulfanyl-substituted phenyl ketone anchor.

It will also be appreciated that compounds prepared with the beads and/or process of the present invention may be screened for an activity of interest by methods well known in the art. For example, such screening can be effected by specialised flow cytometry invented from standard techniques such as described e.g. by Needels et al. (1993, Proc. Natl. Acad. Sci. USA 90: 1070010704, incorporated herein by reference), Dower et al. (supra), and Kaye and Tracey (WO 97/15390, incorporated herein by reference).

Synthesis of a Combinatorial Compound Library

A combinatorial library in accordance with the present invention is a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as peptides, carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule or mediating a biological activity of interest.

The library compounds may comprise any type of molecule of any type of sub-units or monomers, including small molecules and polymers wherein the monomers are chemically connected by any sort of chemical bond such as covalent, ionic, coordination, chelation bonding, etc., which those skilled in the art will recognize can be synthesized on a solid-phase support The term polymer as used herein includes those compounds conventionally called heteropolymers, i.e., arbitrarily large molecules composed of varying monomers, wherein the monomers are linked by means of a repeating chemical bond or structure. The polymers of the invention of this types are composed of at least two sub-units or monomers that can include any bifunctional organic or herteronuclear molecule including, but not limited to amino acids, amino hydroxyls, amino isocyanates, diamines, hydroxycarboxylic acids, oxycarbonylcarboxylic acids, aminoaldehydes, nitroamines, thioalkyls, and haloalkyls.

In the disclosure of the present invention, the terms "monomer," "subunits" and "building blocks" will be used interchangeably to mean any type of chemical building block of molecule that may be formed upon a solid-phase support. The libraries are not limited to libraries of polymers, but is also directed to libraries of scaffolded small molecules.

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports.

To make a combinatorial library, solid-phase supports are reacted with a one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. Thus, it is important to have methods and apparatuses which facilitate the efficient production of large numbers of chemical compounds, yet allow convenient tracking of the compounds over a number of reaction steps necessary to make the compounds.

Combinatorial libraries represent an important tool for the identification of e.g. small organic molecules that affect specific biological functions. Due to the interaction of the small molecules with particular biological targets and their ability to affect specific biological functions, they may also serve as candidates for the development of therapeutics. Accordingly, small molecules can be useful as drug leads eventually resulting in the development of therapeutic agents.

Because it is difficult to predict which small molecules will interact with a biological target. intense efforts have been directed towards the generation of large numbers, or "libraries", of small organic compounds. These libraries can then be linked to sensitive screens to identify the active molecules.

A number of libraries have been designed to mimic one or more features of natural peptides. Such peptidomimetic libraries include phthalimido libraries (WO 97/22594), thiophene libraries (WO 97/40034), benzodiazopene libraries (U.S. Pat. No. 5,288,514), libraries formed by the sequential reaction of dienes (WO 96/03424), thiazolidinone libraries, libraries of metathiazanones and their derivatives (U.S. Pat. No. 5,549,974), and azatide libraries (WO 97/35199) (for review of peptidomimetic technologies, see Gante, J., Angew. Chem. Int. Ed. Engl. 1994, 33, 1699-1720 and references cited therein).

The present invention also resides in a method of synthesising and deconvoluting a combinatorial library as described herein above. The codes of the plurality of beads are determined preferably before the first reaction step, although codes may be determined at any time before the first pooling step (step (d), cf. method steps cited above).

Preferably, every time the plurality of beads is apportioned into reaction vessels, each one of the vessels is analysed to determine which of the detectably distinct beads are in each reaction vessel. A database of all the beads (or corresponding gridspaces, supra) can thus be updated to show the synthetic history of the compound synthesised on each bead.

During a reaction step, the beads in each reaction vessel are reacted with a building block required to assemble a particular compound. Assembly of compounds from many types of building blocks requires use of the appropriate coupling chemistry for a given set of building blocks. Any set of building blocks that can be attached to one another in a step-by-step fashion can serve as the building block set. The attachment may be mediated by chemical, enzymatic, or other means, or by a combination of these.

The resulting compounds can be linear, cyclic, branched, or assume various other conformations as will be apparent to those skilled in the art. For example, techniques for solid state synthesis of polypeptides are described, for example, in Merrifield (1963, J. Amer. Chem. Soc. 35: 2149-2156). Peptide coupling chemistry is also described in "The Peptides", Vol. 1, (eds. Gross, E., and J. Meienhofer), Academic Press, Orlando (1979), which is incorporated herein by reference.

To synthesise the compounds, a large number of the beads are apportioned among a number of reaction vessels. In each reaction, a different building block is coupled to the growing oligomer chain. The building blocks may be of any type that can be appropriately activated for chemical coupling, or any type that will be accepted for enzymatic coupling.

Because the reactions may be contained in separate reaction vessels, even building blocks with different coupling chemistries can be used to assemble the oligomeric compounds (see, The Peptides, op. cit). The coupling time for some of the building block sets may be long. For this reason the preferred arrangement is one in which the building block reactions are carried out in parallel.

After each coupling step, the beads on which are synthesised the oligomers or compounds of the library are pooled and mixed prior to re-allocation to the individual vessels for the next coupling step. This shuffling process produces beads with many oligomer sequence combinations. If each synthesis step has high coupling efficiency, substantially all the oligomers on a single bead will have the same sequence. That sequence is determined by the synthesis pathway (building blockreactions and the order of reactions experienced by the beads) for any given bead.

The maximum length of the oligomers may be about 50, preferably from 3 to 8 building blocks in length, and in some cases a length of 10 to 20 residues is preferred. Protective groups known to those skilled in the art may be used to prevent spurious coupling (see, The Peptides, Vol. 3, (eds. Gross, E., and J. Meienhofer), Academic Press, Orlando (1981), which is incorporated herein by reference).

With enough beads and efficient coupling it is possible to generate complete sets of certain oligomers, if desired. The appropriate size of the beads depends on (1) the number of oligomer synthesis sites desired; (2) the number of different compounds to be synthesised (and the number of beads bearing each oligomer that are needed for screening); (3) the effect of the size of the beads on the specific screening strategies e.g. fluorescence-activated cell sorters (FACS) to be used; and (4) the resolution of the encoding/detection methods employed.

EXAMPLES

Example 1

Handling and Imaging of Spatially Encoded Polymer Beads

A bead sorting apparatus with auxiliaries for controlling the bead sorting, for imaging the beads, and for supplying vacuum was constructed comprising (numbers referring FIG. 7)

a rotating vacuum container comprising
a 100 mm diameter POM capture disc with 100 equidistant 0.2 mm diameter capture holes, arranged along an 80 mm diameter circular track running 10 mm from the edge of the capture disc, the capture disc being positioned with its planar surfaces vertical,
a 100 mm outer diameter POM capture disc holder for holding the capture disc and for containing the vacuum inside the vacuum container, and
a 5 mm outer diameter and 3 mm inner diameter stainless steel shaft with a hole therein for applying a vacuum,
a vacuum container housing comprising
a stainless steel cylinder (306) of inner diameter 10.2 mm surrounding the vacuum container,
a stainless steel circular back plate with a central through-going hole therein for connecting the shaft of the vacuum container to a stepper motor,
three stainless steel separation plates for separating the dry and wet sections of the interior of the cylinder, each separation plate having one central hole equipped with a sealing bearing for holding the shaft of the vacuum container and ensuring smooth rotation of the vacuum container,
a through-going inlet in the side of the stainless-steel cylinder equipped with a connecting piece and being connecting to a first gear pump (Ismatech MCP-Z) via a 4 mm inner diameter flexible tube for applying a vacuum to the vacuum container,
a PMMA circular front plate comprising
a 3 mm wide and 1 mm deep guiding channel centered above the capture holes of the capture disc for guiding the beads,
a measuring section at the 12 o'clock position of the guiding channel comprising three through-going cylindrical holes of 2 mm diameter in the guiding plate with polished PMMA cylinders of diameter 2 mm and length 2 mm inserted therein and arranged such that a bead positioned on the surface of the capture disc and at the center of the measuring section can be simultaneously illuminated through one cylinder by a laser and imaged from two orthogonal directions through the remaining two cylinders,
three water feeding holes in the guiding plate at the respective positions 2.30, 3, and 6 o'clock of the guiding channel equipped with connecting pieces and connected via 2 mm inner diameter silicone tubes to a water reservoir with a free surface for maintaining 1 bar pressure inside the main volume of the guiding channel,
a bead feeding hole in the guiding plate at the 4.30 o'clock position of the guiding channel equipped with a connecting piece and connected to a 5 ml manually operated bead feeding syringe containing an aqueous dispersion of beads, an unloading section comprising, a bead removal hole in the guiding plate at the 7.30 o'clock position of the guiding channel equipped with a connecting piece and connected to the one end of a cylindrical unloading bead container, the other end of the unloading bead container being connected to a gear pump (Ismatech Reglo-z) for supplying a vacuum at the removal hole, the unloading bead container further being equipped with a filter for retaining unloaded beads, and/or a bead stopper inserted in the guiding channel and arranged such that beads are forced away from the capture disc when entering the unloading section, means for rotating the vacuum container comprising a stepper motor (VEXTA PH265-01) (313) mounted on the outside of the back plate and being connected to the shaft of the vacuum container through the hole in the back plate, bead handling apparatus auxiliaries comprising a stepper motor controller (702) that causes the stepper motor to rotate anti-clockwise in steps of 0.9°, i.e., 400 steps per round, corresponding to four steps per capture hole, a first pulse generator (TTi TGP110) (703) with its main output terminal connected to the input of the stepper motor controller whereby it is obtained that the stepper motor rotates 0.9° for every electric pulse generated by the pulse generator, means for imaging the beads comprising a blue laser (313) for illuminating the central section of the imaging section, two CCD-cameras (705), each CCD-camera being equipped with one image intensifier (706), one microscope objective (8× magnification, 6 mm aperture) (707), and one green emission filter (701), the CCD-cameras being arranged such that beads can be imaged from two orthogonal directions in the imaging section, a second pulse generator (TTi TGP110) (704) with its input terminal connected to the AUX output terminal of the first pulse generator such that one delayed pulse is generated by the second pulse generator for every pulse generated by the first pulse generator, the main output terminal of the second pulse generator being connected to the cameras, the image intensifiers, and a computer such that images from the two cameras are simultaneously recorded for every pulse generated by the second pulse generator whereby it is obtained that images are recorded when the capture disc is at rest in-between every step of the capture disc.

The bead sorting apparatus and auxiliaries described above were operated in the following way:

The first gear pump was started at 2500 rpm whereby a vacuum was generated inside the vacuum container whereby water was drawn from the guiding channel into the capture holes whereby the pressure inside the guiding channel was lowered and whereby water was drawns from the water reservoir into the water feeding holes.

The second gear pump was started at 20% of maximum rotational speed whereby water was drawn from the unloading section of the guiding channel through the unloading bead container towards the second gear pump.

The first pulse generator was started in continuous single pulse mode at 0.5 seconds between pulses and a pulse width of 0.5 milliseconds whereby the axis of the stepper motor was caused to rotate 0.90 every 0.5 seconds.

The bead feeding syringe was gently shaken in order to evenly disperse the beads in the water whereafter approximately 0.1 ml of the bead dispersion was infused into the guiding channel through the feeding hole.

The second pulse generator was started in delayed triggered pulse mode with a delay of 0.1 seconds and a pulse width of 1.5 milliseconds whereby one pair of images of the central section of the measuring section were recorded for every rotational step of the vacuum container corresponding to four pairs of images for every capture hole passing the measuring section.

After 142 seconds the seconds the second pulse generator was stopped whereby the imaging was stopped.

After further 120 seconds the first pulse generator was stop whereby the rotation of the vacuum body was stopped.

The first and second gear pumps were stopped.

The water reservoir was disconnected from the guiding channel.

Figure 14:
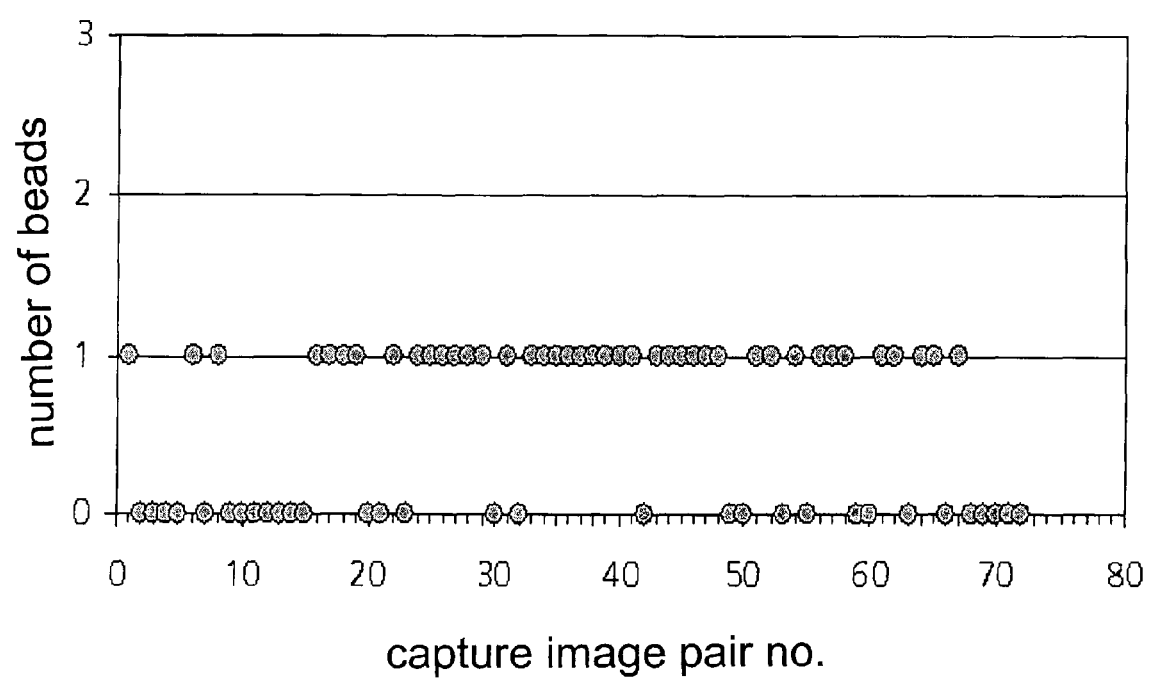
FIG. 14. Demonstration of utility: Number of beads observed in each capture image pair.

The operation of the bead sorting apparatus described above resulted in a portion of the beads being transported from the bead feeding syringe to the unloading bead container, and in a sequence of 287 image pairs comprising 72 capture image pairs being recorded with a capture hole positioned at the central section of the measuring section and 215 non-capture image pairs being recorded in-between the capture image pairs and with no capture hole positioned at the central section of the measuring section. In the capture image pairs the number of beads captured at each capture hole was noted and plottet against capture image pair number in FIG. 14. From the figure it can be seen that only two capture states of the capture holes were observed: no bead captured or one bead captured, which demonstrates that indeed single beads are captured by the present method. It is further apparent from the table that the bead frequency is significantly lower at the beginning as well as towards the end of the sequence compared to the bead frequency at the intermediate part of the sequence. The initial low bead frequency can be explained by the fact that it takes a certain time to transport a captured bead from the loading section to the measuring section. The few scattered captured beads at the beginning of the sequence indicate that a few beads were captured downstream from the loading section, i.e., closer to the measuring section. The absence of beads towards the end of the sequence is due to the loading section being emptied for beads.

Figure 13:
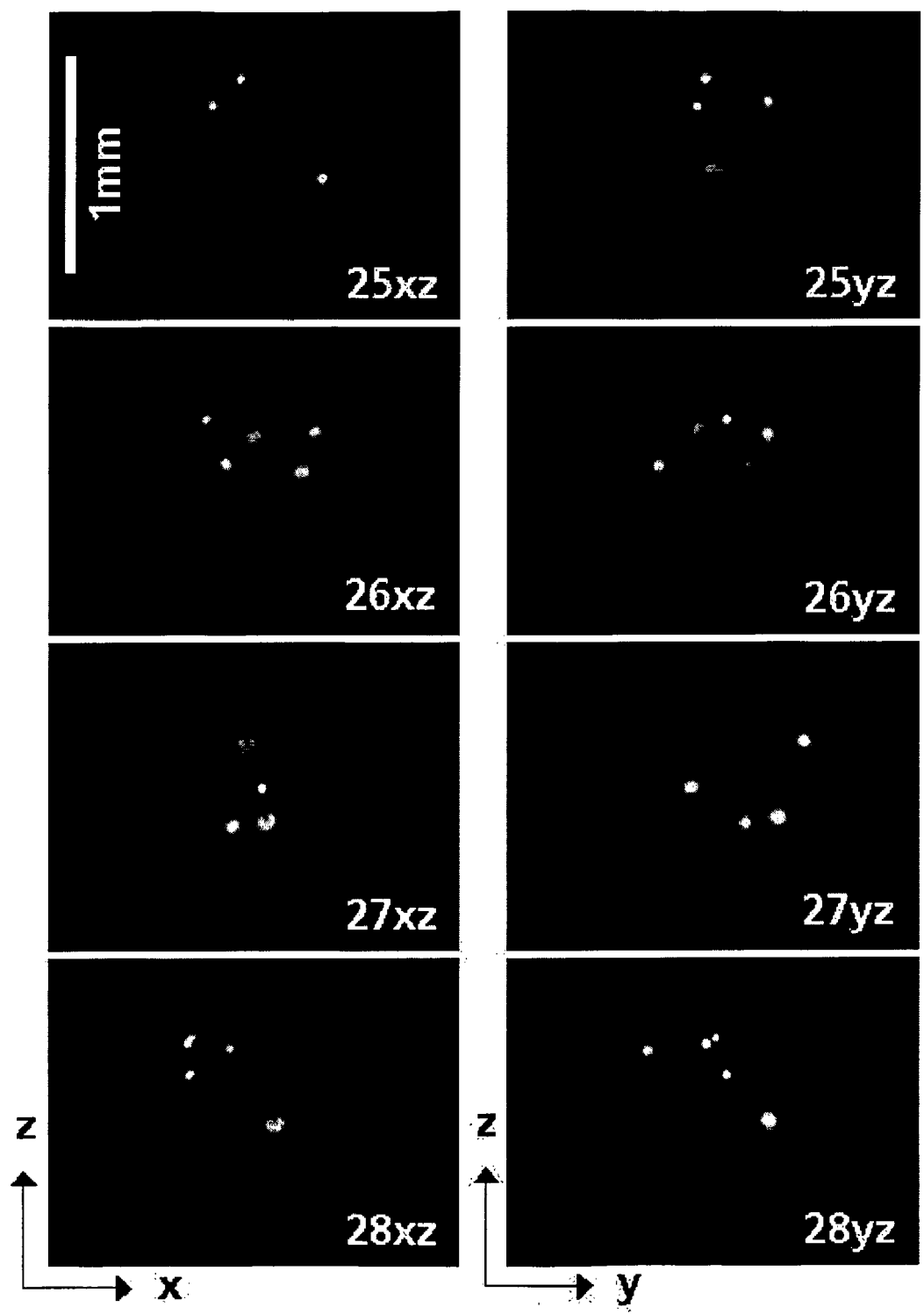
FIG. 13. Demonstration of utility: Sub-sequence of the sequence of capture image pairs showing orthogonal fluorescence image pairs of spatially encoded beads.

A sub-sequence of the sequence of capture image pairs are shown in FIG. 13 with capture image pair number and projection, xz or yz, indicated for each image. The fluorescent microparticles embedded in the beads show up in the images as bright spots on a dark background. On the basis of such images the three-dimensional positions of the centres of the microparticles can be determined and from this data the microparticle centre distance matrix be derived. This demonstrates the applicability of the present method for decoding of multiple distance encoded beads.

The present method is easily up-scaled in terms of total number of beads measured by keeping the first and second pulse generators running and by repeating the infusion of suspended beads at suitable time intervals such as every 140 seconds. Furthermore the throughput of the current method can be increased by lowering the time between pulses generated by the first pulse generator and reducing the time interval between infusion of suspended beads.

For practical purposes the total number of image pairs should be reduced by a factor of four by only recording capture image pairs.

Example 2

Upscaled Handling and Imaging of Spatially Encoded Polymer Beads

The bead handling apparatus and auxiliaries described in Example 1 were operated with the following operation parameters:

The first gear pump was running at 2500 rpm.

The second gear pump was running at 40% of maximum rotational speed.

The first pulse generator was running in continuous single pulse mode with 0.08 seconds between pulses and a pulse width 0.5 milliseconds.

The bead feeding syringe was mounted on a syringe pump set to run in continuous withdrawal/infusion mode with volume setting 0.1 milliliter and rate setting 1.0 ml/min.

It was noted that the actual volume of infused bead dispersion per withdrawal/infusion cycle was substantially less than the nominal value of 0.1 milliliter due to the combined mechanical bias of the syringe mounting and of the flexible plastic syringe itself.

The second pulse generator was running in delayed triggered pulse mode with a delay of 0.1 seconds and a pulse width of 0.5 milliseconds.

After approximately one minute of operation an apparent steady state with regards to bead capture rate was reached and a 26 seconds sequence of image pairs was recorded.

After further two minutes the first pulse generator was stopped.

The operation of the bead handling apparatus described above resulted in
a portion of the beads being transported from the bead feeding syringe to the unloading bead container, and in
a sequence of image pairs comprising
80 capture image pairs and
242 non-capture image pairs The following distribution of beads per capture hole was observed:
18 capture holes with no beads captured,
58 capture holes with one bead captured, and
4 capture holes with two beads captured.

The 58 single beads captured in the 26 seconds correspond to a throughput of approximately 8.000 beads per hour.

The problem with more than one bead captured at a capture hole can be overcome by sorting away the more than one captured beads by methods described elsewhere in the present invention and run them through the apparatus a second time.

Example 3

High Focal Depth Imaging of Spatially Encoded Beads

The bead handling apparatus auxiliaries described in example 1 was modified in the following way: One of the 0.8× magnification, 6 mm aperture microscopes was replaced by a 10× magnification, 1.5 mm aperture microscope.

The bead handling apparatus described in example 1 and the modified auxiliaries was operated in the same way as described in example 1 with the exception that only images from the camera equipped with the low aperture optics were recorded.

Figure 15:
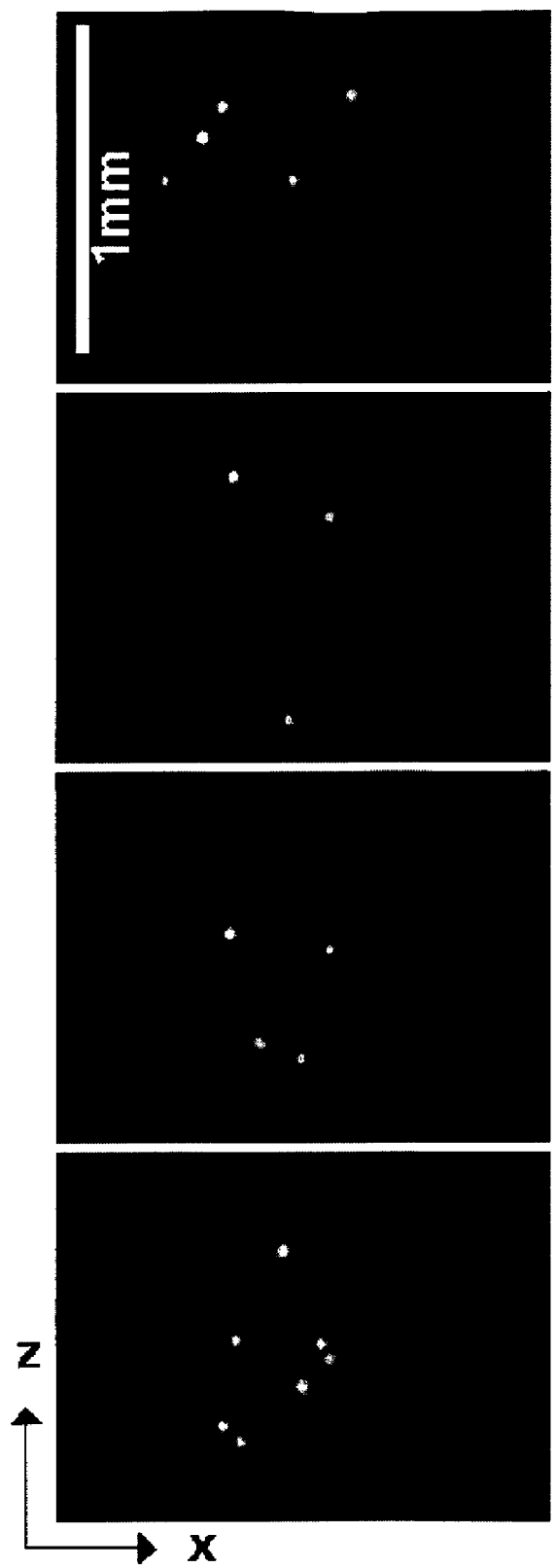
FIG. 15. Demonstration of utility: Images obtained with a 10× magnification, 1.5 mm aperture microscope.

Four images from the resulting image sequence are given in FIG. 15 and show a marked increase in focal depth compared to the images from example 1. It is also clear that the decrease in aperture has led to darker images, as one would expect. Indeed, fluorescence imaging with the use of low aperture optics and exposure times in the millisecond range is a challenging task. However, the dot code clearly appears in the images in FIG. 15. It can be concluded that the use of low aperture optics and the resulting high focal depth image generation are enabled by the combined use of the bead handling apparatus of the present invention that freeze the movement of the encoded beads and image intensifiers that amplify the emitted light from the fluorescent microparticles by a factor of about 10.000.

Example 4

Total Fluorescence Based Bead Sorting

In order to develop novel ligands for use in chromatographic purification of proteins a ligand library is prepared by the following method:

Compound Synthesis 200.000 PEGA-type polymer beads with diameters in the range 0.5-0.7 mm are subjected to a four step solid phase split-process-recombine combinatorial synthesis route involving ten different building blocks per step, whereby approximately 10.000 compounds, here ligands, are generated, each bead carrying one ligand, and each ligand being carried by 20 beads on the average.

In order to evaluate the affinity of the ligands towards a specific protein, the beads are exposed to an aqueous solution of a fluorescence labelled modification of the protein and subsequently weakly adhering fluorescence labelled protein is removed by washing. Now the beads that carry a ligand with high affinity towards the fluorescence labelled protein are strongly fluorescent, whereas beads carrying low affinity ligands are weakly fluorescent or non-fluorescent.

The bead handling apparatus auxiliaries described in example 1 is modified in the following way: The microscopes, the intensifiers, and the CCD cameras are replaced by an optical fibre connected at one end to an imaging window of the measuring section and at the other end to a photo-multiplier tube (PMT) equipped with a fluorescence emission filter for blocking the laser light and transmitting the fluorescence emission and further equipped with an electronic amplifier for amplifying the electronic output from the PMT and an A/D-converter for converting the analogues signal from the amplifier into a digital signal (measuring result).

The bead handling apparatus from example one is equipped with a sorting section at the 10.30 o'clock position comprising
a first cylindrical through-going hole in the guiding plate with a cylindrical high pressure 2 mm inner diameter connecting piece (1103) therein comprising
a first end extending 5 mm above the surface of the guiding plate (408) and connected to the outlet of a sorting valve, such as a 2/2-way mini Flipper Solenoid Valve supplied by bürkert, via a high pressure tube, the state (open/closed) of said valve being controlled by a computer, and the inlet of said valve being connected to a pressurised water source, said pressure being generated by a water pump,
a second end positioned 0.1 mm from the surface of the capture body (416), an interior high pressure volume (1104), a circular 0.5 mm diameter high pressure outlet (1105) near the surface of the capture body and positioned such that the distance between the high pressure outlet and a passing capture hole be at its minimum in the time interval between the steps-wise motion of the capture holes, a second cylindrical through-going hole in the guiding plate with a 3 mm inner diameter cylindrical vacuum connecting piece (1106) therein comprising a first end extending from the surface of the guiding plate (408) connected via a tube to a bead filter, said filter being connected to a vacuum via a tube, said vacuum being generated by a water pump, a second end positioned 0.1 mm from the surface of the capture body, an interior vacuum volume (1101) with a 3 mm inner diameter, a circular 1 mm diameter vacuum outlet (1102) near the surface of the capture body and positioned opposite the high pressure outlet of the high pressure connecting piece, said vacuum outlet connecting the vacuum volume to the guiding channel.

The bead handling apparatus described in example 1 and the modified auxiliaries is operated in the same way as described in example 1 with the exception that instead of imaging the beads in the measuring section their total fluorescence is measured by the photo-multiplier tube. The measuring result is fed to a computer that generates an analysis result, in this case a sorting result, for each bead being measured by the following scheme: if the measuring result is greater than a pre-set value the sorting result=1, whereas, if the measuring result is less than or equal to the value, the sorting result=0.

Each bead, its associated sorting result, and its position on the capture disc from the measuring section and forward is recorded by a computer.

At the sorting section each bead is removed from its capture hole, by briefly (50 milliseconds) opening the sorting valve, and transferred to the second bead filter (309) if its associated sorting result=1, whereas the bead is left on the capture disc if its analysis result=0, At the unloading section all beads that were not removed at the sorting section are removed from the capture disc and transferred to the first bead filter (312), In this way, two fractions of beads are generated, one fraction containing beads with a total fluorescence above the specified value, i.e. a fraction of beads carrying ligands with high affinity towards the fluorescence labelled protein and one fraction containing beads with a total fluorescence below the specified value, i.e. a fraction of beads carrying ligands with low affinity towards the fluorescence labelled protein.

Now, the chemical structure of the ligands carried by the fraction of strongly fluorescent beads can be analysed and determined to some degree of certainty by methods known by those skilled in the art. Prior art instrumentation and methods for total fluorescence based bead sorting exist, however, the performance of the apparatus and method of the present invention to our best knowledge supersedes prior art disclosures in terms of accuracy, i.e., fraction of correctly sorted beads, due to the precise spatial control of beads of the present invention.

The preset value involved in the generation of the sorting result must be sufficiently high for generating only a small fraction of beads with sorting result=1, such as 1% or less, such as 0.1% or less, whereby it is obtained that only beads carrying very high affinity ligands are separated. A proper preset value can be found by a trial and error method: After exposure to fluorescence labelled protein and washing a random fraction of the beads are run through the bead handling apparatus with a random preset value. If the fraction of beads with sorting result=1 is too low the experiment is repeated with a lower preset value, whereas, if the fraction of beads with sorting result=1 is too high the experiment is repeated with a higher preset value. This procedure is repeated until a proper preset value has been found.

The above method can also be used within drug discovery for synthesis and screening of drug candidates. In the case of drug discovery the compounds synthesised on the beads can be drug candidates, and can be screened against a relevant biological compound, such as e.g. an antibody.

The above method can further be used within catalyst development for synthesis and screening of catalyst candidates, in which case the compounds synthesised on the beads can be catalyst candidates, and can be screened against a relevant set of reactants.

Furthermore, the above method or the bead sorting by itself finds use within diagnostics, e.g. for screening biological fluids with regards to the presence of specific DNA or DNA-analogue (e.g. RNA, m-RNA, LNA) sequences. In the case of diagnostics the beads can carry single stranded DNA or DNA-analogue sequences, and can be screened against a biological compound comprising single stranded DNA or DNA-analogue sequences.

Example 5

Combined Bead Identification and Total Fluorescence Bead Sorting

The method for ligand development described in example 4 involves the difficult step of determining the chemical structure of the high affinity ligands. This step is by far the most time consuming, and often leads to ambiguous results. However, the need for this step can be eliminated by keeping track of each bead through its combinatorial synthesis route, i.e. its individual reaction vessel sequence, and after bead sorting identifying the beads carrying high affinity ligands. In this way the chemical structures of the high affinity ligands is derived from the track of its host bead.

The method for compound synthesis described in example 4 is repeated but in this example with spatially encoded PEGA-type beads and with the added steps of fluorescence imaging of all beads entering each reaction vessel in each synthesis step by the method, apparatus, and auxiliaries described in example 2, storing the resulting image pair sequences, each such sequence corresponding to a unique combination of synthesis step number and reaction vessel number, on a storage medium in separate files, each such file being named according to synthesis step number and reaction vessel number, identifying the majority, such as more than 90%, such as more than 99%, of all beads of all resulting image pair sequences by the methods for identification of spatially encoded beads described elsewhere, fluorescence imaging of the high total fluorescence beads by the method, apparatus, and auxiliaries described in example 2, identifying each bead of the high total fluorescence bead fraction resulting from the total fluorescence based sorting procedure, on the basis of its associated fluorescence image pair by the methods for identification of spatially encoded beads described elsewhere, tracking each bead of the high total fluorescence bead fraction resulting from the total fluorescence based sorting procedure through the combinatorial synthesis.

By this method the combinatorial synthesis route of each bead carrying a high affinity ligand is determined, on which basis the chemical structure of its ligand can be derived, whereby the undesired ligand analysis is avoided.

It is preferred that the emission wavelength of the dot-code be sufficiently separate from the wavelength of the protein fluorescence marker, such as e.g. more than 100 nm separate, for avoiding interference between the bead imaging and the total fluorescence measurement.

Example 6

Preparing Spatially Encoded Polymer Beads

Spatially encoded PEGA-type polymer beads are prepared by inverse phase co-polymerisation at 70° C. of acrylamide-end-capped polyethyleneglycol and acrylamide in a 1:1 ratio in 2% (w/w) aqueous sorbitan monolaurate in the presence of 0.6% (w/w) di-methylformamide swelled Oregon green (supplied by Molecular probes) dyed microspheres (TentaGel M30202 supplied by RAPP Polymere). After polymerisation the beads were washed with demineralised water and sieved. The resulting 0.5-0.7 mm diameter fraction is isolated and analysed in the apparatus described in example 1. 80% of the encoded beads comprise from 4 to 10 microparticles.

The invention claimed is:

1. Apparatus for measuring a plurality of optically detectable beads, said apparatus comprising
    a) a vacuum container comprising at least one planar capture body capable of rotating around a central axis, wherein said capture body comprises a plurality of through-going inlets,
    wherein the diameter of each inlet is smaller than the average diameter of the beads to be measured and/or analysed and/or sorted,
    b) a pressure controlling device capable of controlling the pressure in the vacuum container, and
    c) a device for rotating the vacuum container around the axis of the capture body
    d) a device for measuring at least one property of at least one bead
    the apparatus further comprising a capture body support supporting the capture body at a distal end and being connected at a proximal end to a hollow shaft, wherein the hollow shaft is fitted with a shaft opening so that a vacuum can be applied to the interior of the vacuum container, and
    a vacuum container housing comprising an outer cylinder comprising an opening for connecting the shaft hole with the pressure controlling device, and a guiding plate comprising at least one opening allowing the through-going inlets to be accessible to beads to be loaded onto the capture body, said guiding plate being attached to the top part of the outer cylinder, thereby defining in the space between the guiding plate and the capture body a guiding channel for harbouring beads, said guiding plate confining the vacuum container to the interior of the vacuum container housing.

2. The apparatus according to claim 1 wherein the ratio R between a) the average diameter of the beads being manipulated, and b) the diameter of the through-going inlets, R=a/b, is more than 2.

3. The apparatus according to claim 1, wherein the capture body is a planar disc.

4. The apparatus according to claim 3 wherein the support is circular.

5. The apparatus according to claim 1, wherein the distance between the axis of rotation of the capture body and each of the through-going inlets of the capture body is the same for each of the through-going inlets of the capture body.

6. The apparatus according to claim 5, wherein the distance between neighbouring through-going inlets is the same for all pairs of neighbouring through-going inlets.

7. The apparatus according to claim 1, wherein the vacuum container is connected to a device for rotating the vacuum container, operably linked to a momentum transfer split for transferring the momentum from the stepper motor to the vacuum container thereby causing the vacuum container to rotate in a controlled step-wise fashion.

8. The apparatus according to claim 7, wherein the device for rotating the vacuum container is a stepper motor.

9. The apparatus according to claim 1 further comprising an analysing device for analysing results being generated from the measurement of the at least one property of the at least one bead, wherein said analysis enables individual beads to be characterised and/or identified and optionally also sorted.

10. The apparatus according to claim 9 further comprising at least one device for sorting a plurality of beads on the basis of the result generated by the analysing device.

11. A method for sorting at least one bead of a plurality of beads, said method comprising the steps of
    i) providing a plurality of beads each comprising at least one label,
    ii) providing an apparatus for sorting at least one bead according to claim 10,
    iii) contacting at least one bead of the plurality of beads provided in step i) with the vacuum container capture body of the apparatus provided in step ii),
    iv) rotating the capture body to transfer at least one bead from the loading section of the vacuum container to the measuring section of the vacuum container,
    v) using the measuring device of the apparatus for measuring at least one property of at least one bead,
    vi) using the analysing device for analysing data generated by the measuring device for measuring at least one property of at least one bead, and
    vii) sorting the at least one bead of a plurality of beads based on the result of the analysis performed in step vi).

12. A method for sorting at least one bead of a plurality of beads, said method comprising the steps of
    i) providing a plurality of beads each comprising at least one label,
    ii) providing an apparatus for sorting at least one bead according to claim 10,
    iii) contacting at least one bead of the plurality of beads provided in step i) with the vacuum container capture body of the apparatus provided in step ii),
    iv) rotating the capture body to transfer at least one bead from the loading section of the vacuum container to the measuring section of the vacuum container,
    v) using the measuring device of the apparatus for measuring at least one property of at least one bead, and
    vi) using the analysing device for analysing data generated by the measuring device for measuring at least one property of at least one bead,
    vii) identifying at least one bead of a plurality of beads by analysing the data generated by the measuring device for measuring at least one property of at least one bead, and
    viii) sorting the at least one bead of a plurality of beads based on the identification performed in step vii).

13. A method for analysing data generated by measuring at least one property of at least one bead of a plurality of beads, said method comprising the steps of
  i) providing a plurality of beads each comprising at least one label,
  ii) providing an apparatus for analysing at least one property of at least one bead according to claim 9,
  iii) contacting at least one bead of the plurality of beads provided in step i) with the vacuum container capture body of the apparatus provided in step ii),
  iv) rotating the capture body to transfer at least one bead from the loading section of the vacuum container to the measuring section of the vacuum container,
  v) using the measuring device of the apparatus for measuring at least one property of at least one bead, and
  vi) analysing data generated by the measuring device for measuring at least one property of at least one bead.

14. A method for identifying at least one bead of a plurality of beads, said method comprising the steps of
  i) providing a plurality of beads each comprising at least one label,
  ii) providing an apparatus for analysing at least one property of at least one bead according to claim 9,
  iii) contacting at least one bead of the plurality of beads provided in step i) with the vacuum container capture body of the apparatus provided in step),
  iv) rotating the capture body to transfer at least one bead from the loading section of the vacuum container to the measuring section of the vacuum container,
  v) using the measuring device of the apparatus for measuring at least one property of at least one bead, and
  vi) using the analysing device for analysing data generated by the measuring device for measuring at least one property of at least one bead, and
  vii) identifying at least one bead of a plurality of beads by analysing the data generated by the measuring device for measuring at least one property of at least one bead.

15. The apparatus according to claim 1 further comprising a treating device for treating at least one bead optionally having been subjected to measuring or analysing.

16. A method for treating at least one bead of a plurality of beads, said method comprising the steps of
  i) providing a plurality of beads each comprising at least one label,
  ii) providing an apparatus for treating at least one bead according to claim 15,
  iii) contacting at least one bead of the plurality of beads provided in step i) with the vacuum container capture body of the apparatus provided in step ii),
  iv) rotating the capture body to transfer at least one bead from the loading section of the vacuum container to the measuring section of the vacuum container,
  v) using the measuring device of the apparatus for measuring at least one property of at least one bead,
  vi) analysing data generated by the measuring device for measuring at least one property of at least one bead, and
  vii) treating at least one bead of a plurality of beads based on the result of the analysis performed in step vi).

17. A method for treating at least one bead of a plurality of beads, said method comprising the steps of
  i) providing a plurality of beads each comprising at least one label
  ii) providing an apparatus for treating at least one bead according to claim 15,
  iii) contacting at least one bead of the plurality of beads provided in step i) with the vacuum container capture body of the apparatus provided in step ii),
  iv) rotating the capture body to transfer at least one bead from the loading section of the vacuum container to the measuring section of the vacuum container,
  v) using the measuring device of the apparatus for measuring at least one property of at least one bead, and
  vi) using the analysing device for analysing data generated by the measuring device for measuring at least one property of at least one bead,
  vii) identifying at least one bead of a plurality of beads by analysing the data generated by the measuring device for measuring at least one property of at least one bead, and
  viii) treating at least one bead of a plurality of beads based on the identification obtained in step vii).

18. A method for treating at least one bead of a plurality of beads, said method comprising the steps of
  i) providing a plurality of beads each comprising at least one label,
  ii) providing an apparatus for treating at least one bead according to claim 15,
  iii) contacting at least one bead of the plurality of beads provided in step i) with the vacuum container capture body of the apparatus provided in step ii),
  iv) rotating the capture body to transfer at least one bead from the loading section of the vacuum container to the measuring section of the vacuum container,
  v) using the measuring device of the apparatus for measuring at least one property of at least one bead,
  vi) analysing data generated by the measuring device for measuring at least one property of at least one bead,
  vii) sorting the at least one bead of a plurality of beads based on the result of the analysis performed in step vi), and
  viii) treating the at least one bead of a plurality of beads having been sorted in step vii).

19. A method for treating at least one bead of a plurality of beads, said method comprising the steps of
  i) providing a plurality of beads each comprising at least one label,
  ii) providing an apparatus for treating at least one bead according to claim 15,
  iii) contacting at least one bead of the plurality of beads provided in step i) with the vacuum container capture body of the apparatus provided in step ii),
  iv) rotating the capture body to transfer at least one bead from the loading section of the vacuum container to the measuring section of the vacuum container,
  v) using the measuring device of the apparatus for measuring at least one property of at least one bead, and
  vi) using the analysing device for analysing data generated by the measuring device for measuring at least one property of at least one bead,
  vii) identifying at least one bead of a plurality of beads by analysing the data generated by the measuring device for measuring at least one property of at least one bead,
  viii) sorting the at least one bead of a plurality of beads based on the identification performed in step vii), and
  ix) treating the at least one bead of a plurality of beads having been sorted in step viii).

20. A method for measuring at least one property of at least one bead of a plurality of beads, said method comprising the steps of
  i) providing a plurality of beads each comprising at least one label,
  ii) providing an apparatus for measuring at least one property of at least one bead according to claim 1, iii) contacting at least one bead of the plurality of beads provided in step i) with the vacuum container capture body of the apparatus provided in step ii),
iv) rotating the capture body to transfer at least one bead from the loading section of the vacuum container to the measuring section of the vacuum container, and
v) using the measuring device of the apparatus for measuring at least one property of at least one bead.

21. The method of claim 20, wherein the measuring of at least one property of at least one optically detectable bead located in the measuring section of the apparatus comprises the steps of i) activating a source of illumination,
ii) capturing at least one image of the at least one optically detectable bead, and
iii) optionally storing the at least one image of the at least one optically detectable bead.

22. The apparatus according to claim 1, wherein the optically detectable beads are polymer beads.

* * * * *

UNITED STATES PATENT AND TRADEMARK OFFICE
CERTIFICATE OF CORRECTION

| | | |
|---|---|---|
| PATENT NO. | : 7,869,011 B2 | Page 1 of 1 |
| APPLICATION NO. | : 10/583997 | |
| DATED | : January 11, 2011 | |
| INVENTOR(S) | : Soeren Flygenring Christensen et al. | |

It is certified that error appears in the above-identified patent and that said Letters Patent is hereby corrected as shown below:

On the Title Page

Item (73) Assignee, correct the incorrect assignee name and city by deleting "Novo Norkisk A/S, Baysvaerd (DK)" and insert --Novo Nordisk A/S, Bagsvaerd (DK)--.

Signed and Sealed this
Fourth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,869,011 B2 | |
| APPLICATION NO. | : 10/583997 | |
| DATED | : January 11, 2011 | |
| INVENTOR(S) | : Soeren Flygenring Christensen et al. | |

It is certified that error appears in the above-identified patent and that said Letters Patent is hereby corrected as shown below:

This certificate supersedes the Certificate of Correction issued October 4, 2011.
The certificate should be vacated since petition to correct assignee was dismissed.
The Certificate of Correction should not have been issued.

Signed and Sealed this
Sixth Day of December, 2011

David J. Kappos
*Director of the United States Patent and Trademark Office*

UNITED STATES PATENT AND TRADEMARK OFFICE
CERTIFICATE OF CORRECTION

PATENT NO. : 7,869,011 B2
APPLICATION NO. : 10/583997
DATED : January 11, 2011
INVENTOR(S) : Soeren Flygenring Christensen et al.

Page 1 of 1

It is certified that error appears in the above-identified patent and that said Letters Patent is hereby corrected as shown below:

On the title page, Item (73) Assignee, correct the incorrect assignee name and city by deleting "Novo Norkisk A/S, Baysvaerd (DK)" and insert --Novo Nordisk A/S, Bagsvaerd (DK)--.

Signed and Sealed this
Twenty-eighth Day of August, 2012

David J. Kappos
*Director of the United States Patent and Trademark Office*